United States Patent
Hermann et al.

(10) Patent No.: US 11,135,033 B2
(45) Date of Patent: Oct. 5, 2021

(54) TISSUE LOCALIZATION DEVICE AND METHOD OF USE THEREOF

(71) Applicant: HOLOGIC, INC., Marlborough, MA (US)

(72) Inventors: George D. Hermann, Los Altos Hills, CA (US); Jonathan M. Olson, San Jose, CA (US); Michael J. Drews, Palo Alto, CA (US); Gail S. Lebovic, Frisco, TX (US); David B. Willis, Portland, OR (US)

(73) Assignee: HOLOGIC, INC., Marlborough, MA (US)

( * ) Notice: Subject to any disclaimer, the term of this patent is extended or adjusted under 35 U.S.C. 154(b) by 293 days.

(21) Appl. No.: 16/146,815

(22) Filed: Sep. 28, 2018

(65) Prior Publication Data
US 2019/0029773 A1   Jan. 31, 2019

Related U.S. Application Data

(63) Continuation of application No. 15/488,358, filed on Apr. 14, 2017, now Pat. No. 10,524,875.

(60) Provisional application No. 62/448,307, filed on Jan. 19, 2017, provisional application No. 62/322,729, filed on Apr. 14, 2016.

(51) Int. Cl.
*A61B 90/00* (2016.01)
*A61B 17/34* (2006.01)

(52) U.S. Cl.
CPC .......... *A61B 90/39* (2016.02); *A61B 17/3468* (2013.01); *A61B 2017/3409* (2013.01); *A61B 2017/3413* (2013.01); *A61B 2090/3908* (2016.02); *A61B 2090/3925* (2016.02); *A61B 2090/3962* (2016.02); *A61B 2090/3987* (2016.02); *A61B 2090/3991* (2016.02)

(58) Field of Classification Search
None
See application file for complete search history.

(56) References Cited

U.S. PATENT DOCUMENTS

| | | |
|---|---|---|
| 6,327,772 B1 | 12/2001 | Zadno Azizi et al. |
| 6,605,047 B2 | 8/2003 | Zarins et al. |
| 6,679,872 B2 | 1/2004 | Turovskiy et al. |
| 6,706,033 B1 | 3/2004 | Martinez et al. |
| 6,723,085 B2 | 4/2004 | Jang et al. |
| 6,752,767 B2 | 6/2004 | Turovskiy et al. |
| 6,902,564 B2 | 6/2005 | Morgan et al. |
| 7,014,648 B2 | 3/2006 | Ambrisco et al. |

(Continued)

FOREIGN PATENT DOCUMENTS

WO   WO 2017/181136   10/2017

*Primary Examiner* — Amelie R Davis
*Assistant Examiner* — Marjan Saboktakin
(74) *Attorney, Agent, or Firm* — Kacvinsky Daisak Bluni PLLC

(57) ABSTRACT

Tissue localization devices and methods of localizing tissue using tissue localization devices are disclosed. The tissue localization device can comprise a handle comprising a delivery control, a delivery needle extending out from the handle, and a localization element within the delivery needle. The localization element can be deployed out of the delivery needle or retracted back into the delivery needle when the delivery control is translated in a first direction or a second direction, respectively. The localization element can be coupled to a flexible tracking wire.

7 Claims, 48 Drawing Sheets

(56) References Cited

U.S. PATENT DOCUMENTS

| | | |
|---|---|---|
| 7,197,363 B2 | 3/2007 | Prakash et al. |
| 7,322,360 B2 | 1/2008 | Fogarty et al. |
| 7,427,287 B2 | 9/2008 | Turovskiy et al. |
| 7,468,042 B2 | 12/2008 | Turovskiy et al. |
| 7,846,108 B2 | 12/2010 | Turovskiy et al. |
| 7,862,559 B2 | 1/2011 | Prakash et al. |
| 8,035,570 B2 | 10/2011 | Prakash et al. |
| 8,221,418 B2 | 7/2012 | Prakash et al. |
| 8,231,666 B2 | 7/2012 | Kim et al. |
| 8,235,981 B2 | 8/2012 | Prakash et al. |
| 8,262,703 B2 | 9/2012 | Prakash et al. |
| 8,313,486 B2 | 11/2012 | Kim et al. |
| 8,401,668 B2 | 3/2013 | Deem et al. |
| 8,406,894 B2 | 3/2013 | Johnson et al. |
| 8,409,188 B2 | 4/2013 | Kim et al. |
| 8,535,302 B2 | 9/2013 | Ben-Haim et al. |
| 8,657,870 B2 | 2/2014 | Turovskiy et al. |
| 8,663,213 B2 | 3/2014 | Turovskiy et al. |
| 8,672,933 B2 | 3/2014 | Shiu et al. |
| 8,728,067 B2 | 5/2014 | Prakash et al. |
| 8,740,893 B2 | 6/2014 | Shiu et al. |
| 8,808,282 B2 | 8/2014 | Prakash et al. |
| 9,186,216 B2 | 11/2015 | Turovskiy et al. |
| 9,241,763 B2 | 1/2016 | Kim et al. |
| 9,468,499 B2 | 10/2016 | Turovskiy et al. |
| 9,511,210 B2 | 12/2016 | Deem et al. |
| 9,561,096 B2 | 2/2017 | Kim et al. |
| 9,655,539 B2 | 5/2017 | Shachar et al. |
| 9,675,266 B2 | 6/2017 | Afonso et al. |
| 9,713,497 B2 | 7/2017 | Kim et al. |
| 2004/0049224 A1 | 3/2004 | Buehlmann et al. |
| 2004/0168692 A1* | 9/2004 | Fogarty ............... A61B 90/39 128/899 |
| 2009/0149850 A1 | 6/2009 | Turovskiy et al. |
| 2013/0018394 A1 | 1/2013 | Gambale |
| 2015/0174379 A1* | 6/2015 | Bagaoisan ......... A61M 25/0075 604/509 |
| 2016/0346074 A1* | 12/2016 | Tafti .................... A61F 2/01 |
| 2017/0296294 A1 | 10/2017 | Hermann et al. |

* cited by examiner

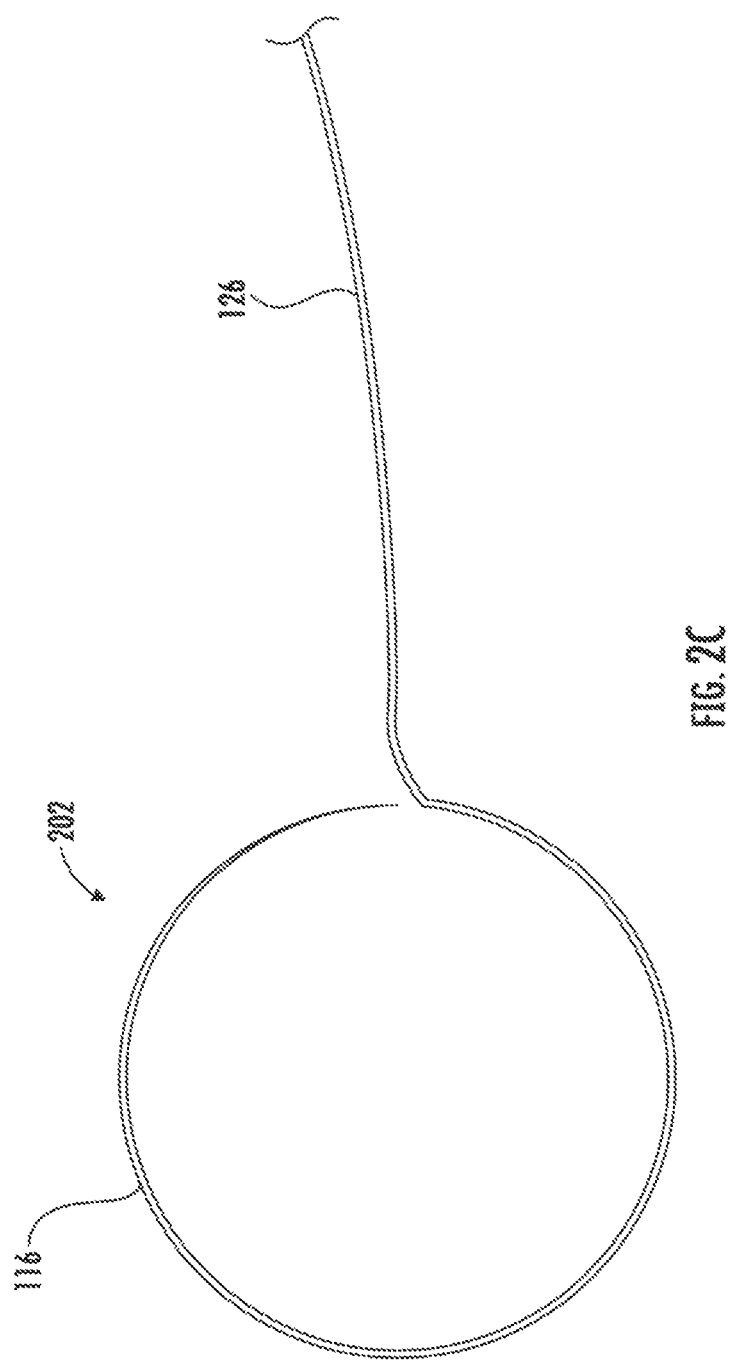

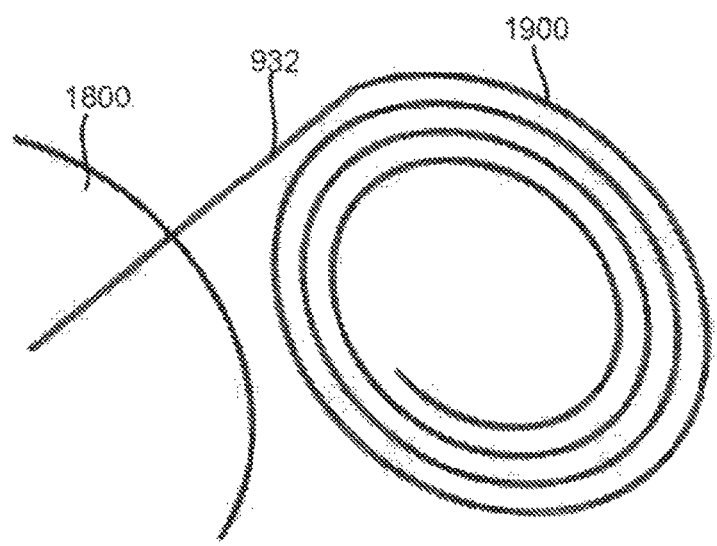
FIG. 19A
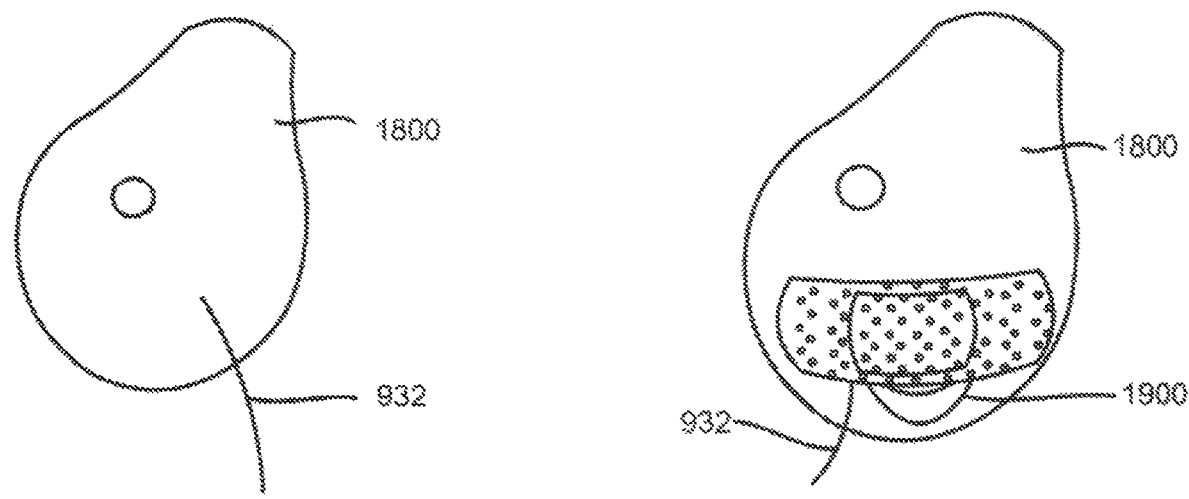
FIG. 19B
FIG. 19C

TISSUE LOCALIZATION DEVICE AND METHOD OF USE THEREOF

CROSS-REFERENCE TO RELATED APPLICATION

This application is a continuation of U.S. patent application Ser. No. 15/488,358, filed on Apr. 14, 2017, which claims the benefit of U.S. Provisional Patent Application No. 62/322,729, filed on Apr. 14, 2016, and U.S. Provisional Patent Application No. 62/448,307, filed on Jan. 19, 2017, which are incorporated herein by reference in their entireties.

FIELD OF TECHNOLOGY

The present disclosure relates generally to the field of tissue localization and, more specifically, to a tissue localizing device for marking or bounding a suspect tissue mass.

BACKGROUND

Despite the advances made in technologies such as medical imaging to assist the physician in the diagnosis and treatment of patients with possible abnormal tissue growth such as cancer, it is still often necessary to physically identify abnormal tissue regions for subsequent surgical removal. One disease for which this approach is a critical tool is breast cancer.

In the detection and treatment of breast cancer, open or excisional biopsies are often advisable when a suspicious tissue mass may need to be removed. In addition, lumpectomy or partial mastectomy may be performed when the tissue mass is cancerous as part of breast conservation therapy (BCT). One technique that is frequently employed to physically identify the abnormal tissue region to be removed is called wire localization. Wire localizations often require a radiologist to manually insert a wire that contains one or more hooks on its distal end into the breast of the patient through a needle and then position the hook region of the wire so that the end of the wire resides within or is adjacent to the suspect tissue requiring surgical removal. The needle is removed and the wire is left in the tissue and the patient is then transferred to the operating room, typically several hours later, to have the suspect or target tissue or lesion removed by a surgeon.

However, such wires are often inaccurately placed, and once placed they are prone to migration, and cannot be easily adjusted once they have exited the needle. Moreover, even if the wire has been properly placed, the surgeon often cannot intraoperatively identify the tip of the wire, which can result in the surgeon removing a larger portion of tissue than is necessary to optimize the chances for cancer-free margins of the tissue specimen that is removed. Also, if the suspect tissue mass is not found at the end of the wire, the surgeon often ends up cutting or removing non-afflicted tissue without removing the lesion. In addition, after placement but before the surgical procedure, the wire protrudes stiffly from the body and can become dislodged or migrate to position remote from the originally demarcated region of identified tissue. While the localization wire resides in the patient awaiting surgery, the wire can be uncomfortable and cannot be adequately secured in a manner that would permit the patient to sleep overnight without discomfort or without a high risk of dislodgement. Because of these risks associated with migration and patient discomfort, the patient must proceed with the surgical removal of the lesion the same day as the placement of the localization wire. In addition, logistical delays between placement of the wire and eventual surgical excision can exceed several hours, leading to additional discomfort and risk of migration.

Another drawback of current localization wires is the need to pass the needle and wire through the lesion leading to potential transmission of cancer cells, sometimes referred to as needle tract seeding.

Therefore, a solution is needed that can accurately and removably place a localization or marking device into a patient to demarcate a region of tissue for subsequent surgical removal. Such a solution should reliably define the border of the tissue to be removed and reduce the risk of inadvertent migration, even over a period of hours or days.

SUMMARY

Tissue localization devices and methods of localizing tissue using tissue localization devices are disclosed. The tissue localization device can include a delivery needle having a needle lumen, a localization element slidably translatable within the needle lumen, and a liner in the needle lumen. The localization element can be detachable from the delivery needle. The liner can be slidably translatable relative to the needle lumen and can be located radially between the needle lumen and at least part of the localization element.

The localization element can have an echogenic surface treatment. The echogenic surface treatment can be a surface roughness, a pattern cut into a surface of the localization element, or combinations thereof.

The tissue localization device can include a handle with a slidable delivery control and a pusher element partially within the needle lumen. The delivery needle can extend from the handle.

The localization element can be detachably held by the pusher element. The localization element can be detachable from the pusher element in response to a translation of the slidable delivery control in a first longitudinal direction. The localization element can be releasable from the liner when a distal end of the pusher element is translated longitudinally beyond the liner.

The slidable delivery control can have a first interface surface and a second interface surface. The handle can have a proximal end and a distal end. The first interface surface can be upwardly concave when viewed from the proximal end to the distal end and the second interface surface can be upwardly concave when viewed from the distal end to the proximal end.

The handle can have a handle dorsal side and a handle ventral side opposite the handle dorsal side. The localization element can be configured to curve in a direction of the handle dorsal side when deployed. The handle can have an elongate slot along the handle dorsal side. The slidable delivery control can be coupled to the pusher element via a fastener extending through the elongate slot.

The pusher element can have or be defined by a delivery port at a distal end of the pusher element. At least part of the localization element can be detachably held within the delivery port when the localization element is within the needle lumen. The pusher element can have a pusher dorsal side, a pusher ventral side, and a pusher distal end. The pusher distal end can be sloped and form an obtuse angle with the pusher ventral side.

The tissue localization device can include a spring coupled to a proximal end of the liner. The spring can be configured to be at least partially compressed when the pusher element is translated toward a distal end of the delivery needle relative to the liner in response to a translation of the slidable delivery control in the first longitudinal direction. The tissue localization device can also have a tracking wire coupled to the localization element. At least a segment of the tracking wire can be configured to be coiled or tied into a loop.

Furthermore, the tissue localization device can include a delivery needle having a needle lumen, a pusher element slidably translatable within the needle lumen, and a localization element having an interlocking framework or interlocking portion. The pusher element can have or be defined by a delivery port. The interlocking framework can be interlockable with the delivery port when at least part of the pusher element resides within the needle lumen. The interlocking framework can be releasable from the delivery port when the delivery port exits the needle lumen.

The interlocking framework of the localization element can include an eyelet frame and a shoulder portion. The eyelet frame can be detachably positioned within the delivery port when the localization element is within the needle lumen.

Furthermore, the tissue localization device can include a handle with a slidable delivery control and a delivery needle extending out from the handle. The delivery needle can have a needle lumen and a pusher element slidably translatable and partially within the needle lumen. The tissue localization device can also include a localization element detachably held by the pusher element when in the needle lumen.

The pusher element can have a pusher dorsal side and a pusher ventral side. The needle lumen can have a lumen dorsal surface defining an upper portion or top half of the needle lumen and a lumen ventral surface defining a lower portion or bottom half of the needle lumen. The pusher element can also have a pusher proximal end and a pusher distal end opposite the pusher proximal end. The pusher distal end can be sloped and form an obtuse angle with the pusher ventral side. The obtuse angle formed by the pusher distal end and the pusher ventral side can be seen when viewed from a lateral side of the tissue localization device. The pusher distal end can also form an acute angle with the pusher dorsal side when viewed from the lateral side of the tissue localization device.

At least part of the localization element can be configured to exit the delivery needle in response to a translation of the slidable delivery control in a first longitudinal direction. The localization element can be configured to retract into the delivery needle in response to a translation of the slidable delivery control in a second longitudinal direction opposite the first longitudinal direction. The localization element can be retracted back into the delivery needle after at least a part of the localization element is deployed out of the delivery needle.

The localization element can be constrained into a first configuration when within the needle lumen. The localization element can transform into a second configuration when deployed out of the delivery needle. The second configuration can be a circular shape. The second configuration can also be a half-circle shape, a crescent shape, a falciform shape, or a sickle-shape. The localization element can have an element distal end with one sharpened element tip. The localization element can also have at least two sharpened element tips. The two sharpened element tips can branch out or diverge at an angle away from one another. The two sharpened element tips can also furcate or branch out. The localization element can have an echogenic surface treatment. The echogenic surface treatment can be a surface roughness, a pattern cut into a surface of the localization element, or combinations thereof.

The localization element can have a curvature plane. The entire localization element can be substantially within the curvature plane. In other variations, at least part of the localization element can be curved in alignment with the curvature plane and another part of the localization element can curve out of the curvature plane. The localization element can curve into a complete or partial helix.

The tissue localization device can also have a liner partially encasing the pusher element. The liner can be positioned in between a portion of the pusher element and the needle lumen. A portion of the localization element can be encased by the pusher element and the liner. The liner can be made from a metallic material a polymer such as a polyether ether ketone (PEEK), or combinations thereof. The liner can be a hollow tube. In other variations, the liner can have a dorsal liner and a ventral liner. The dorsal liner can be positioned in between the pusher dorsal side and the lumen dorsal surface. The ventral liner casing can be positioned in between the pusher ventral side and the lumen ventral surface.

The tissue localization device can include a spring coupled to a proximal end of the liner. The spring can be configured to be at least partially compressed when the pusher element is translated toward a distal end of the delivery needle relative to the liner in response to a translation of the slidable delivery control in the first longitudinal direction.

The tissue localization device can also include a tracking wire coupled to the localization element. The tracking wire can be a stainless steel wire covered by a polymer jacketing. The tracking wire can be a flexible wire capable of being coiled or tied into a loop. At least part of the tracking wire can be covered by a polymer jacketing.

The delivery needle can have a needle dorsal side and a needle ventral side opposite the needle dorsal side. The delivery needle can also have a beveled distal end. The localization element can be configured to exit or be deployed out of the beveled distal end. The beveled distal end can have a rounded edge along a proximal rim of the beveled distal end at a region that can be referred to as a heel. The beveled distal end can also have two lateral sharpened edges converging and meeting at a needle tip. The two lateral sharpened edges can be contiguous with or extend out from the rounded edge.

The delivery needle can have a needle dimple proximal to the rounded edge along the needle dorsal side. The needle dimple can have a dimple length and a dimple width. The needle dimple can be a substantially oval-shaped dimple. The needle dimple can be a concavity extending radially into the needle lumen and obstructing part of the needle lumen along the dimple length.

The pusher element can have a delivery port and the localization element can be detachably held within the delivery port. The delivery port can be a cutout along the pusher dorsal side. The localization element can be deployed out of the delivery needle when the pusher element pushes the localization element in the first longitudinal direction. The localization element can be configured to automatically detach or dislodge from the pusher element and the delivery needle when at least part of the delivery port is translated by the delivery control out of the delivery needle. The localization element can be retracted back into the delivery needle when at least a portion of the localization element is still within the delivery port and the pusher element pulls the localization element in the second longitudinal direction.

The delivery port can have a distal port side, a proximal port side, and a port base. The distal port side can form an acute angle with the port base when viewed from the lateral side of the tissue localization device.

The localization element can include a locator proximal end and a locator distal end opposite the locator proximal end. The locator distal end can include a sharpened locator tip. The locator proximal end can include an eyelet frame surrounding an aperture, a narrow portion, and a shoulder portion. The eyelet frame can be detachably positioned within the delivery port of the pusher element when the movement or translation of the localization element is controlled by the delivery control. The localization element can be deployed out of the delivery needle when the pusher element pushes the shoulder portion of the localization element in the first longitudinal direction. The localization element can be retracted back into the delivery needle when at least a portion of the eyelet frame is still within the delivery port and the pusher element pulls on a side of the eyelet frame, namely an eyelet shoulder, in the second longitudinal direction.

The localization element can be covered by a blue-oxide finish. The blue-oxide finish can reduce friction when the localization element is translated through the needle lumen and makes contact with an inner surface of the needle lumen.

The handle can have a handle distal end, a handle proximal end opposite the handle distal end, a handle dorsal side, a handle ventral side opposite the handle dorsal side, and an elongate slot defined along the handle dorsal side. The handle can also have a handle lumen. At least part of the pusher element can slidably translate within the handle lumen. The delivery control can be coupled to the pusher element via fasteners extending through the elongate slot. In some variations, the tissue localization device can comprise a gear mechanism and the translation of the pusher element can be facilitated by the gear mechanism.

The delivery control can include a first interface surface and a second interface surface. The first interface surface can be upwardly concave when viewed from the proximal end to the distal end and the second interface surface can be upwardly concave when viewed from the distal end to the proximal end. The localization element can be translated in the first longitudinal direction when the first interface surface is pushed in the first longitudinal direction. The localization element can curve in a direction of the handle dorsal side when deployed out of the delivery needle.

The tracking wire can be coupled to the localization element at various points along the length of the localization element. The tracking wire can be coupled to the locator proximal end of the localization element. The tracking wire can be coupled or tied to the eyelet frame of the localization element. The tracking wire can be threaded through the aperture and tied to the eyelet frame. At least part of the tracking wire can be positioned within the delivery port when the eyelet frame is positioned within the delivery port. The tracking wire can be coupled to the localization element at a midpoint along the length of the localization element.

The tracking wire can have a wire distal segment and a wire proximal segment opposite the wire distal segment. At least part of the wire distal segment can be secured to part of another segment of the wire in between the wire distal segment and the wire proximal segment at an attachment site along the wire. The wire distal segment can be secured to part of another segment of the wire by adhesive or spot welding. For example, the attachment site can be a weld site. The segment of the wire in between the wire distal segment and the attachment site can be formed as a loop. A polymer jacketing can cover or ensheath at least part of the tracking wire. The polymer jacketing can also cover or ensheath the attachment site. The tracking wire can comprise or be composed of stainless steel. The polymer jacketing can be a heat-shrink polymer or tube wrapped around the tracking wire.

A method for using a tissue localization device is also disclosed. The method can involve translating a localization element of the tissue localization device in a first longitudinal direction through a needle lumen of a delivery needle of the tissue localization device. The method can also involve deploying a localization element of the tissue localization device out of the delivery needle into tissue and retracting the localization element into the needle lumen after at least part of the localization element is deployed out of the delivery needle. The method can further involve repositioning the tip of the delivery needle and redeploying the localization element out of the delivery needle into the tissue.

The method can also include deploying the localization element out of the delivery needle into a curved configuration having a first curvature plane and redeploying the localization element out of the delivery needle into the curved configuration having a second curvature plane. The method can further involve compressing a spring coupled to a proximal end of a liner partially encasing a pusher element coupled to the slidable delivery control prior to deploying the localization element out of the delivery needle.

The method can also involve advancing a needle tip of the delivery needle into the tissue to an offset from a target tissue site of the tissue and positioning an ultrasound transducer on the tissue. The method can further involve deploying the localization element out of the delivery needle by pushing a slidable delivery control of the tissue localization device in the first longitudinal direction along a handle of the tissue localization device and moving the ultrasound transducer on the tissue while translating the localization element.

A method of localizing tissue using a tissue localization device is also disclosed. The method can involve positioning a delivery needle of the tissue localization device adjacent to or at a target tissue site and holding the handle of the tissue localization device using one hand of a user. The needle tip can be positioned at an offset location adjacent to a target tissue site. The offset location can be separated from the target tissue site by less than a difference between a diameter of the localization element and a diameter of the target tissue site.

The user can include a surgeon, a radiologist, or another health professional. The method can also involve pushing a slidable delivery control of the tissue localization device in a first longitudinal direction using at least one finger of the same hand of the user. The method can involve translating a localization element of the tissue localization device in the first longitudinal direction through a needle lumen of the delivery needle in response to the pushing of the slidable delivery control.

The method can also involve deploying the localization element out of the delivery needle adjacent to or at the target tissue site. At least part of the localization element can curve when deployed. The method can also involve at least partially compressing a spring coupled to a proximal end of a liner partially encasing the pusher element prior to deploying the localization element out of the delivery needle.

The method can further involve retracting the localization element back into the delivery needle after at least part of the localization element is deployed out of the delivery needle. Retracting the localization element can involve holding the handle of the tissue localization device using the one hand of the user and pulling the slidable delivery control in a second longitudinal direction using at least one finger of the same hand of the user. The second longitudinal direction can be opposite the first longitudinal direction.

The method can further involve deploying the localization element out of the delivery needle into a curved configuration having a curvature plane. The localization element can radially surround at least a portion of a suspect tissue mass in the tissue of the patient such that the curvature plane of the localization element intersects at least a portion of the suspect tissue mass. In another variation, the localization element can be deployed adjacent or proximal to the suspect tissue mass such that the curvature plane does not intersect any portion of the suspect tissue mass.

The localization element can be coupled to a flexible tracking wire. At least a segment of the tracking wire can extend out of the tissue of the patient while a distal end of the tracking wire can be coupled to the localization element deployed within the tissue of the patient. The distal end of the tracking wire can swivel or rotate relative to the localization element when the localization element and the tracking wire are deployed out of the delivery needle and the pusher element. The distal end of the tracking wire can swivel or rotate into a deployed alignment. The deployed alignment can be a spatial positioning or alignment which is secant or non-tangent with respect to a curve formed by the deployed localization element. For example, the localization element can be deployed into a circular configuration and the distal end of the tracking wire can be aligned secant or non-tangent to the circular configuration.

The method can further involve retracting a distal tip of the delivery needle away from the target tissue site. Retracting the distal tip of the delivery needle can expose the tracking wire coupled to the localization element.

The method can further involve viewing a position of the localization element in tissue using an ultrasound transducer. The method can also involve moving the ultrasound transducer on a tissue surface proximal to the target tissue site while deploying the localization element.

The method can involve locating a suspect tissue mass in the patient by periodically pulling on the segment of a tracking wire extending outside the body of the patient. The method can further involve palpating or feeling, with at least one finger of a user, an outer tissue layer (e.g., a dermis) above the target tissue site while pulling on the segment of the tracking wire extending outside the body of the patient. The method can further involve locating a suspect tissue mass within the tissue of the patient based on a tension exhibited by the tracking wire being pulled and a movement felt by the at least one finger of the user.

The method can further involve coiling the segment of the tracking wire extending out of the tissue of the patient tracking wire into a loop and adhering (e.g., with Tegaderm™ or other biocompatible adhesives or dressings) or otherwise securing the tracking wire extending outside the body of the patient to the dermis or patient dressing of the patient.

In another variation, a tissue localization device can include a handle having a rotatable delivery control, a delivery needle extending out from the handle, and a localization element configured to be deployed out of the delivery needle when the delivery control is rotated in a first rotational direction. The localization element can be in a first configuration when within the delivery needle. The localization element can transform into a second configuration when deployed out of the delivery needle. A part of the localization element can be detachably held by a distal end of a pusher element configured to longitudinally translate within the delivery needle. The tissue localization device can further include a tracking wire coupled to the localization element.

The localization element can be retracted into the delivery needle when the rotatable delivery control is rotated in a second rotational direction. The rotatable delivery control can include a knob.

The handle can include an orientation arch defined along a handle dorsal side. The orientation arch can have a curvature and the localization element can be configured to curve in a direction matching the curvature of the orientation arch when deployed. The handle can have a handle lumen. The tissue localization device can include a drive pipe within the handle lumen. The drive pipe can be configured to rotate within the handle lumen in response to a rotation of the rotatable delivery control. The drive pipe can have a pipe lumen surrounding a car element.

The car element can be coupled to the pusher element. The car element can be configured to translate longitudinally within the pipe lumen of the drive pipe in response to the rotation of the drive pipe.

The tissue localization device can further include a sound-generating element. The sound-generating element can be configured to produce sound when at least part of the localization element exits or is deployed out of the delivery needle. The sound-generating element can include a spring.

The tissue localization device can also include a tactile feedback-generating element. The tactile feedback-generating element can be configured to produce tactile feedback at least part of the time when the localization element exits or is being deployed out of the delivery needle.

In another variation, a method of localizing tissue using a tissue localization device involves positioning a delivery needle of the tissue localization device adjacent to or at a target tissue site. The method can also involve rotating a rotatable delivery control of the tissue localization device in a first rotational direction and translating a localization element of the tissue localization device in a first longitudinal direction through a needle lumen of the delivery needle in response to the rotation of the rotatable delivery control. Translating the localization element in the first longitudinal direction further involves translating a pusher element within a drive pipe of the tissue localization device.

The method can further involve deploying the localization element out of the delivery needle adjacent to or at the target tissue site in response to the rotation of the rotatable delivery control. The method can also involve retracting a distal tip of the delivery needle away from the target tissue site and exposing a tracking wire coupled to the localization element while retracting the distal tip of the delivery needle.

The method can further involve holding a handle of the tissue localization device using one hand of a user and rotating the rotatable delivery control in the first rotational direction using at least one finger of the same hand of the user.

The method can also involve retracting the localization element into the delivery needle after at least part of the localization element is deployed out of the delivery needle. The localization element can be retracted by holding a handle of the tissue localization device using one hand of a user and rotating the rotatable delivery control in a second rotational direction using at least one finger of the same hand of the user.

The method can further involve creating tactile feedback using a tactile feedback-generating element of the tissue localization device when the localization element is partially deployed out of a distal tip of the delivery needle. The method can also involve generating a sound using a sound-generating element of the tissue localization device when the localization element is partially deployed out of a distal tip of the delivery needle.

In another variation, a method for localizing tissue using a tissue localization device including a delivery needle comprises advancing, using one hand, a needle tip of the delivery needle of the tissue localization device into a tissue at an offset from a target tissue site of the tissue. The method can further involve positioning, using another hand, an ultrasound transducer proximal to the target tissue site on a tissue surface of the tissue. The method can also involve deploying a localization element out of the delivery needle into the tissue. The method can further involve moving the ultrasound transducer on the tissue surface while deploying the localization element.

A tissue localization system is also disclosed. The tissue localization system can include a tissue localization device configured to be held by only one hand of a user and an ultrasound transducer configured to be held by only one hand of a user and moved on a surface of the tissue while the localization element is deployed into the tissue. The tissue localization device can include a handle with a slidable delivery control, a delivery needle extending from the handle, and a pusher element coupled to the slidable delivery control. The tissue localization device of the tissue localization system can also include a localization element detachably held by the pusher element. The pusher element can be configured to deploy at least part of the localization element from the delivery needle into a tissue in response to a translation of the slidable delivery control.

A tracking wire to locate a marked target tissue site is also disclosed. The tracking wire can include a wire having a wire distal segment and a wire proximal segment opposite the wire distal segment. At least part of the wire distal segment can be secured to a part of another segment of the wire in between the wire distal segment and the wire proximal segment at an attachment site along the wire. The segment of the wire in between the wire distal segment and the attachment site can be formed as a loop. The tracking wire can also include a polymer jacketing covering at least part of the wire. The attachment site can be covered by the polymer jacketing.

The wire can be made of stainless steel. At least a segment of the tracking wire can be configured to be deployed into the tissue of a patient. At least a segment of the tracking wire in between the wire distal segment and the wire proximal segment can be configured to be tied into a knot around a portion of a localization element.

A method of preparing a tissue localization assembly is also disclosed. The method can involve threading a wire distal segment of a wire through an aperture of a localization element. The method can also involve securing at least part of the wire distal segment to part of another segment of the wire in between the wire distal segment and the wire proximal segment at an attachment site along the wire. The segment of the wire in between the wire distal segment and the attachment site can form a loop. The method can further involve covering at least part of the wire with a polymer jacketing.

The method can also involve covering the attachment site with the polymer jacketing. The method can further involve inserting a segment of the wire into a lumen of a pusher element of a tissue localization device. The method can also involve positioning at least a part of the localization element coupled to the wire into a delivery port of the pusher element. The method can further involve slidably translating the pusher element into a lumen of a delivery needle of the tissue localization device.

BRIEF DESCRIPTION OF THE DRAWINGS

FIG. 2C is a black-and-white image of the localization element attached to a tracking wire.

FIG. 19A illustrates a segment of a flexible tracking wire extending out from a patient's tissue and coiled to reduce the excess length of the tracking wire.

FIG. 19B illustrates a segment of a flexible tracking wire extending out from breast tissue.

FIG. 19C illustrates a segment of tracking wire coiled and taped to breast tissue.

DETAILED DESCRIPTION

Figure 1A:
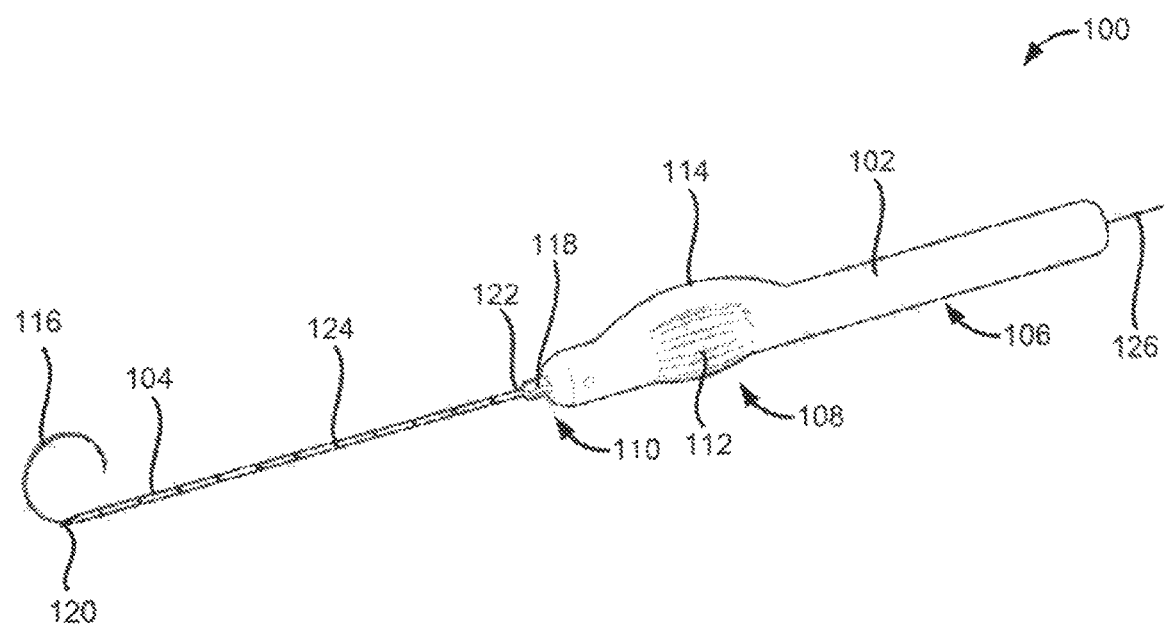
FIG. 1A illustrates a perspective view of a tissue localization device.
Figure 1B:
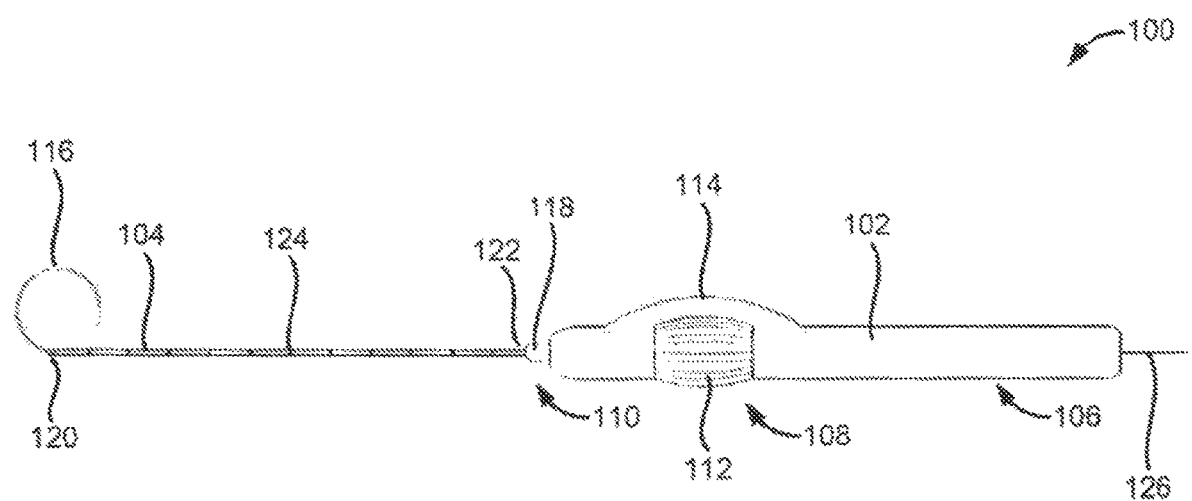
FIG. 1B illustrates a side view of the tissue localization device.
Figure 1C:
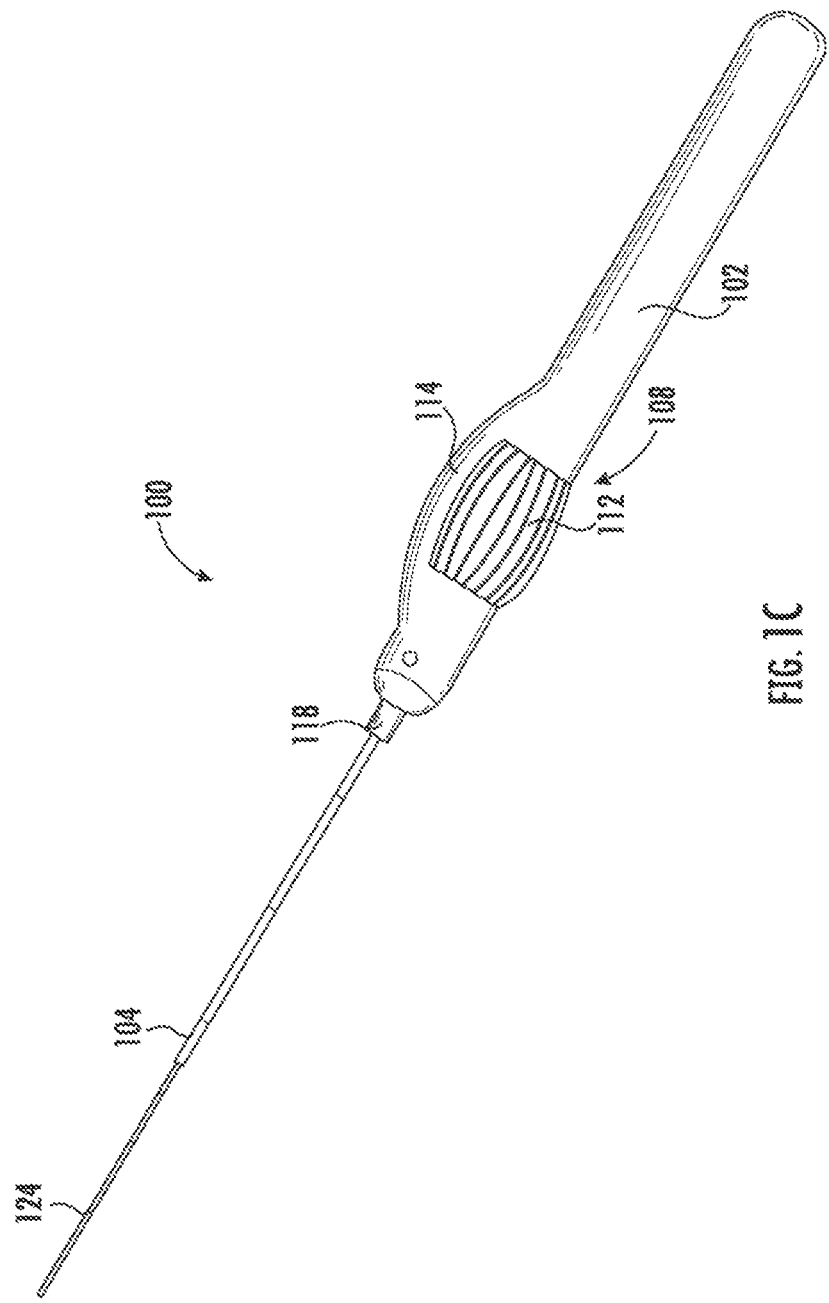
FIG. 1C is a black-and-white image of the tissue localization device.

FIGS. 1A, 1B, and 1C illustrate that a tissue localization device 100 can include a handle 102 coupled to a delivery needle 104. The handle 102 can include a handle grip 106, a knob portion 108, and a handle nose 110. The handle grip 106 can be a portion of the handle 102 configured to be grasped or held by a user such as a surgeon, radiologist or other imaging professional. The handle grip 106 can be sized or shaped for a user to grasp the handle 102 with one hand.

The handle grip 106 can be shaped as a cylinder, a tube, a rod, or combinations thereof. In other variations, the handle grip 106 can be shaped as an elongate ovoid, prism, ellipsoid, cone, or combinations thereof. The handle grip 106 can have finger grooves, holes, indentations, or combinations thereof.

The handle grip 106 can be connected to or contiguous with a knob portion 108. The knob portion 108 can be a portion of the handle 102 housing a knob 112 for controlling the tissue localization device 100. The knob portion 108 can include an orientation arch 114. The orientation arch 114 can be a curved protuberance extending out from a surface of the handle 102. The orientation arch 114 can help a user properly orient the tissue localization device 100 by informing the user of the deployed curvature of a localization element 116. For example, the orientation arch 114 can have a half-oval or bow-shaped curvature denoting a direction and/or plane of curvature of the localization element 116 when deployed.

The knob 112 can be barrel or ellipsoid-shaped component for controlling the deployment or retraction of the localization element 116. The knob 112 can be a separate component attached to the handle 102 at the knob portion 108. The knob 112 can be positioned in proximity to the orientation arch 114. The knob 112 can have longitudinal ridges or grooves. The longitudinal ridges or grooves of the knob 112 can allow a user to more easily rotate the knob 112. The knob 112 can be rotated in a clockwise direction, a counterclockwise direction, or combinations thereof. The knob 112 can freely rotate until the localization element 116 is deployed out of the tissue localization device 100. A user can hold the handle grip 106 of the handle 102 with one hand and use the fingers of the same hand to rotate the knob 112 to control the deployment or retraction of the localization element 116.

The knob portion 108 can be connected to or contiguous with the handle nose 110. The handle nose 110 can be a portion of the handle 102 coupled to or housing a portion of the delivery needle 104. The handle nose 110 can include a nozzle or luer end 118. The luer end 118 can fixedly secure a packaging needle cover tube (not shown) to the handle 102. The luer end 118 can be cross-shaped, conical, rectangular, frustoconical, or combinations thereof.

The handle 102, the knob 112, or combinations thereof can be fabricated from or made of a polymer such as an injection molded polymer. For example, the handle 102, the knob 112, or combinations thereof can be composed of or comprise acrylonitrile butadiene styrene (ABS) plastic, polycarbonate, polypropylene (PP), or combinations thereof. The handle 102 can also be fabricated from or include parts fabricated from glass-filled polymers, metals or metal alloys such as stainless steel, or combinations thereof.

The handle 102 can have a longitudinal dimension of between 100.0 mm and 200.00 mm. For example, the handle 102 can have a longitudinal dimension of approximately 155.0 mm. When the handle grip 106 is shaped as a cylinder, the handle grip 106 can have a diameter between 9.0 mm and 13.0 mm. For example, the handle grip 106 can have a diameter of approximately 11.0 mm.

The delivery needle 104 can include a needle tip 120 and a needle base 122. The needle tip 120 can be an end of the delivery needle 104 for puncturing the skin of a patient and deploying the localization element 116. The delivery needle 104 can have a needle lumen. The needle lumen can be a hollow cavity within the delivery needle 104 for storing or housing the localization element 116, a tracking wire 126, a portion therein, or combinations thereof.

The needle tip 120 can have a beveled or deflected tip or point. The needle tip 120 can also include a blade, a sharpened edge, or a cutting edge. For example, the needle tip 120 can include a hypodermic point bevel, an intradermal point bevel, a deflected point septum, or combinations thereof. The needle tip 120 can also have a bevel angle of between 15 degrees and 45 degrees.

The needle base 122 can be partially housed or secured by the luer end 118, the handle nose 110, other internal handle components, or combinations thereof. The delivery needle 104 can include one or more depth markers 124 in between the needle tip 120 and the needle base 122. The depth markers 124 can be markings, etchings, or surface indentations on the surface of the delivery needle 104 in between the needle tip 120 and the needle base 122. The depth markers 124 can assist a user, such as a surgeon, radiologist or other imaging professional, to insert the delivery needle 104 into the tissue site of the patient. The depth markers 124 can be separated by increments of millimeters, centimeters, inches, or combinations thereof.

The delivery needle 104 can be made of metal, a metal alloy such as stainless steel, or a rigid medical grade polymer. The delivery needle 104 can have a diameter of between 0.5 mm and 1.5 mm. The delivery needle 104 can have a diameter of approximately 1.0 mm.

The delivery needle 104, for example when made from a rigid medical polymer, can include or be covered by a radiopaque material or coating. The radiopaque material or coating can include gold or gold coating, platinum or platinum coating, tungsten or tungsten coating, iridium or iridium coating, tantalum or tantalum coating, barium sulfate, rhodium, or combinations thereof.

The delivery needle can have an echogenic surface such as can be generated by sandblasting or beadblasting on portions of the needle, such as at the distal tip, for example, to enhance visualization of the needle or portions thereof during clinical ultrasound imaging.

FIGS. 1A and 1B illustrate that the localization element 116 can be curved or loop-shaped when deployed. The localization element 116 can be a flexible wire or length of metal, polymer, or combinations thereof. The localization element 116 can take on an arcuate, curvilinear, or looping shape when deployed out of the delivery needle 104. The localization element 116 can penetrate tissue and serve as a boundary or guidance marker for a tissue mass for subsequent removal and/or analysis.

FIGS. 1A and 1B also illustrate that the tissue localization device 100 can include a tracking wire 126. The tracking wire 126 can be coupled or connected to the localization element 116. The tracking wire 126 can be made of metal, a metal alloy such as stainless steel, or a medical grade polymer, a stainless steel cable with polymer jacketing, a polymer thread, a polymer tube, or combinations thereof. The tracking wire 126 can include or be covered by a radiopaque material, for example, for enhanced visualization of the tracking wire 126 when imaged.

The tracking wire 126 can be used to track the deployment or insertion path of the delivery needle 104, the localization element 116, or combinations thereof into the patient. The tracking wire 126, or a portion therein, can be housed within the handle 102 when the localization element 116 is not deployed or not fully deployed. A segment of the tracking wire 126 can also be located outside of the handle 102 when the localization element 116 is not deployed or not fully deployed. For example, a segment of the tracking wire 126 can extend out of an end of the handle 102 proximate to the handle grip 106 when the localization element 116 is not deployed or not fully deployed.

Figure 2A:
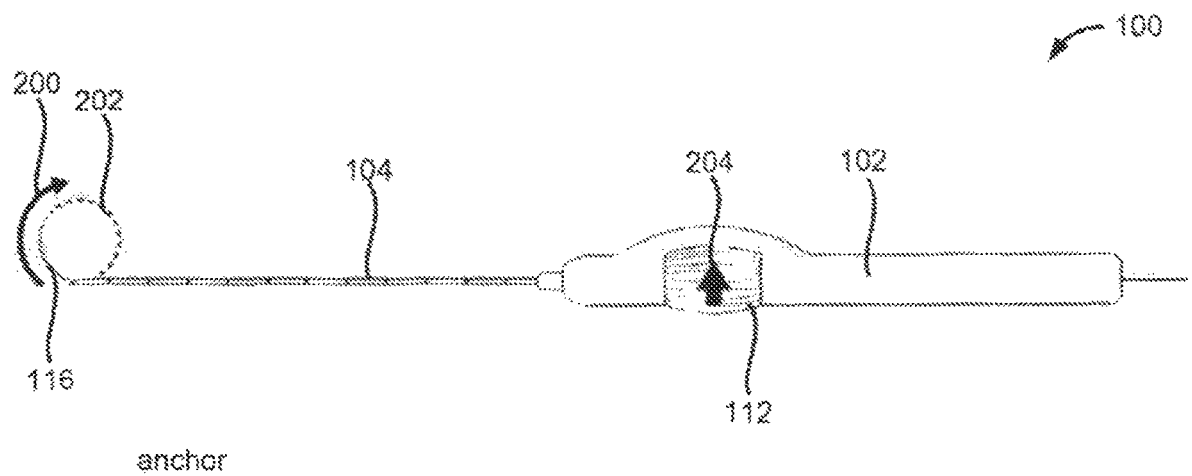
FIG. 2A illustrates deployment of a localization element.

FIG. 2A illustrates that the localization element 116 can have a deployment trajectory 200 when deployed from the delivery needle 104. The deployment trajectory 200 can include a substantially two-dimensional or planar trajectory along a substantially two-dimensional plane. For example, the deployment trajectory 200 can include a substantially two-dimensional trajectory along a plane bisecting a longitudinal axis of the tissue localization device 100. In other variations, the deployment trajectory 200 can include a three-dimensional trajectory.

The localization element 116 can follow its deployment trajectory 200 to achieve a predetermined shape 202. The predetermined shape 202 can include a circular shape, an oval, a spiral shape, or combinations thereof. In other variations, the predetermined shape 202 can include a triangular shape, a rectangular shape, a trapezoidal shape, or combinations thereof. The deployment trajectory 200 can be a trajectory or path mimicking or following such a predetermined shape 202. For example, the localization element 116 can have the predetermined shape 202 of a two-dimensional circle and the localization element 116 can emerge from the delivery needle 104 in a circular trajectory.

For example, the localization element 116 can have predetermined shape 202 of a circle or loop having a diameter of between 10.0 to 40.0 mm. The localization element 116 can have a predetermined shape 202 of a circle or loop having a diameter of approximately 25.0 mm.

FIG. 2A illustrates that the localization element 116 can be deployed from the delivery needle 104 when the knob 112 is turned in a first rotational direction 204. The first rotational direction 204 can include a clockwise rotational direction or a counterclockwise rotational direction when viewed along the longitudinal axis of the tissue localization device 100 from the handle grip 106 to the handle nose 110.

For example, the localization element 116 can exit or emerge out of the needle tip 120 of the delivery needle 104 when the knob 112 is turned in the first rotational direction 204. The localization element 116 can exit or emerge out of the needle tip 120 in a reverse loop trajectory representing the deployment trajectory 200 of the localization element 116. The reverse loop trajectory can be a substantially circular trajectory curving backward toward the needle base 122 of the delivery needle 104. The localization element 116 can initially curve upward or in a direction toward the apex or top of the orientation arch 114 before looping backwards toward the needle base 122. In other variations, the localization element 116 can initially curve downward or in a direction away from the apex or top of the orientation arch 114 before looping backwards toward the needle base 122.

Figure 2B:
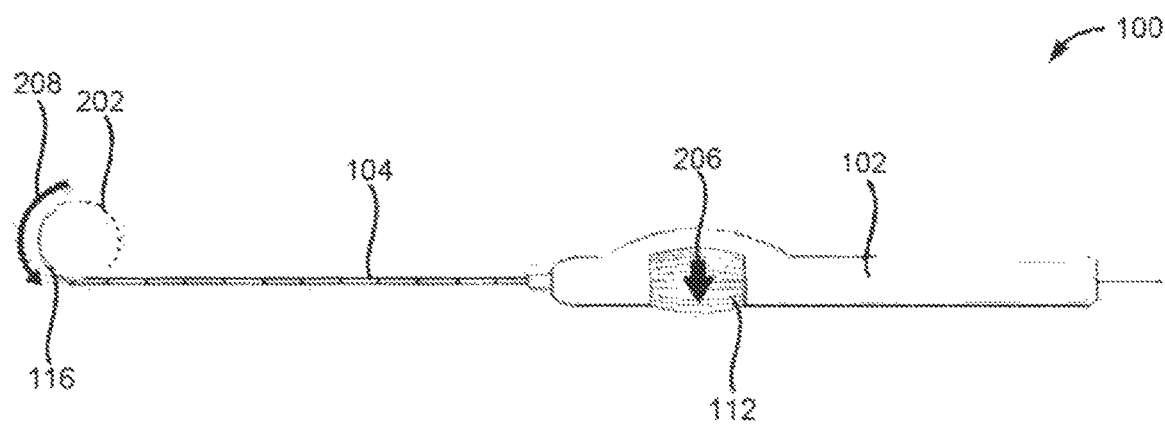
FIG. 2B illustrates retraction of the localization element.

FIG. 2B illustrates that the localization element 116 can be retracted into the delivery needle 104 when the knob 112 is turned in a second rotational direction 206. The second rotational direction 208 can be a different rotational direction than the first rotational direction 204. The second rational direction can include a counterclockwise rotational direction or a clockwise rotational direction when viewed along the longitudinal axis of the tissue localization device 100 from the handle grip 106 to the handle nose 110.

The localization element 116 can have a retraction trajectory 208 when retracting back into the delivery needle 104. The retraction trajectory 208 can be the reverse or opposite of the deployment trajectory 200. For example, when the deployment trajectory 200 is an upward curving loop trajectory as shown in FIG. 2A, the retraction trajectory 208 is a downward curving loop trajectory as shown in FIG. 2B. The retraction trajectory 208 can be a substantially two-dimensional trajectory, a three-dimensional trajectory, or combinations thereof.

The localization element 116 can re-enter or retract back into the needle tip 120 of the delivery needle 104 when the knob 112 is turned in the second rotational direction 208. The localization element 116 can re-enter or retract back into the needle tip 120 by reversing or retracing the deployment trajectory 200 of the localization element 116.

FIG. 2C illustrates that the localization element 116 can be in a circular shape representing the predetermined shape 202. The localization element 116 can have a predetermined shape 202 set by using shape memory techniques, heating techniques, bending techniques, or combinations thereof. The localization element 116 can be composed of or fabricated from spring steel, a nickel-titanium alloy such as Nitinol™, a shape memory polymer, stainless steel, or combinations thereof.

The localization element 116 can include or be covered by a radiopaque material or coating. The radiopaque material or coating can include gold or gold coating, platinum or platinum coating, tungsten or tungsten coating, iridium or iridium coating, tantalum or tantalum coating, barium sulfate, rhodium, hydrophilic and other lubricious coatings, or combinations thereof.

Figure 3A:
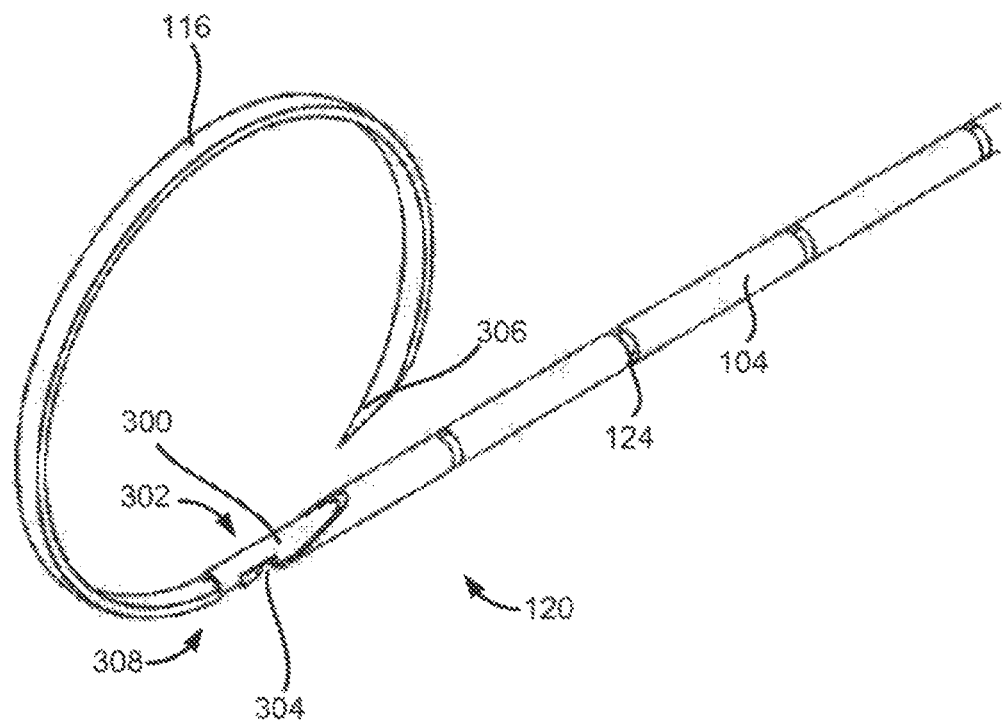
FIG. 3A illustrates a close-up perspective view of a tip of a delivery needle during deployment of the localization element.

FIG. 3A illustrates that the tissue localization device 100 can include a pusher element or pusher element 300. The pusher element 300 can be used by the tissue localization device 100 to deploy the localization element 116. The pusher element 300 can be positioned inside the delivery needle 104 when the localization element 116 resides in the delivery needle 104. The pusher element 300 can slidably move longitudinally within the delivery needle 104. The pusher element 300 can be advanced longitudinally forward or longitudinally backward through the delivery needle 104 when a user turns the knob 112 in the first rotational direction 204 or the second rotational direction 208, respectively. The pusher element 300 can be composed of or fabricated from a polymer, stainless steel, or combinations thereof.

The pusher element 300 can include a pusher tip 302. The pusher tip 302 can be a portion of the pusher element 300 removeably attached to the localization element 116. The pusher tip 302 can have a window 304. The window 304 can be a partial opening or cutaway section along the pusher tip 302.

The localization element 116 can include an element base 308 and an element tip 306. The element base 308 can be a portion of the localization element 116 configured to be removeably attached to the pusher element 300. The element tip 306 can be an end of the localization element 116 distal to the element base 308. The element tip 306 can be configured to pierce or cut through patient tissue. The element tip 306 can have a beveled edge, a sharpened edge, a pointed tip, or combinations thereof.

Figure 3B:
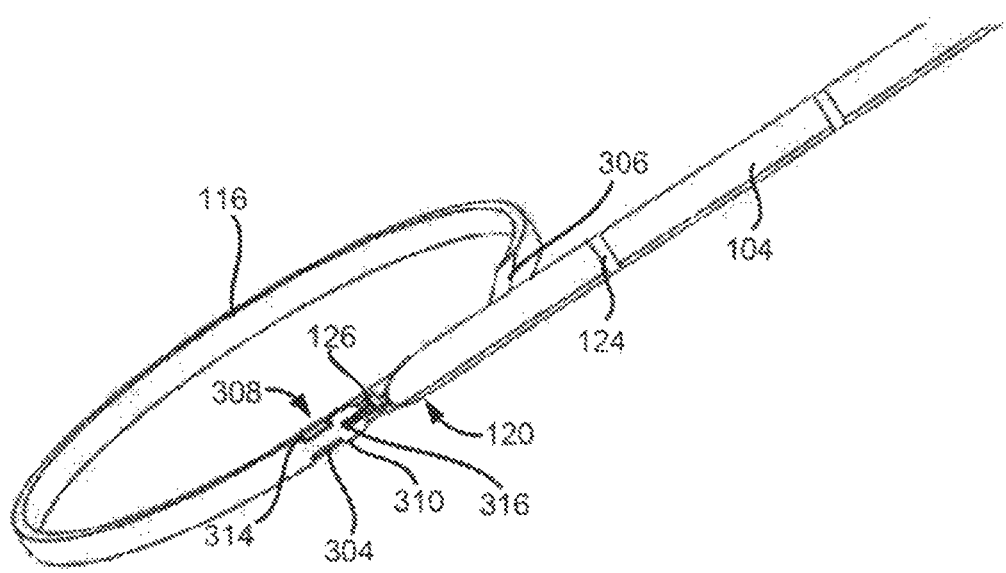
FIG. 3B illustrates a close-up bottom perspective view of the tip of the delivery needle during deployment of the localization element.

FIG. 3B illustrates that the element base 308 of the localization element 116 can include an eyelet frame 310, a narrow portion 312, and a shoulder 314. The eyelet frame 310 can be connected to the shoulder 314 by the narrow portion 312. The eyelet frame 310 can have an eyelet 316. The eyelet 316 can be an opening or bore configured to receive the tracking wire 126. The tracking wire 126 can be threaded through the eyelet 316 and the threaded end can be connected, for example by crimping via a ferrule or tied, to the remainder of the tracking wire 126 using a crimp sleeve, a tie, a knot, an adhesive, a coil, heat shrink polymer jacketing, or combinations thereof.

The eyelet frame 310 can fit within the window 304 of the pusher element 300 to allow the pusher element 300 to engage with the localization element 116. The portion of the pusher element 300 distal to the window 304 can partially surround the narrow portion 312 of the element base 308 when the eyelet frame 310 is within the window 304.

FIG. 3B illustrates that the pusher element 300 can advance the localization element 116 out of the delivery needle 104 by pushing on the shoulder 314 of the localization element 116. The pusher element 300 can also retract or draw the localization element 116 into the delivery needle 104 by pulling on the eyelet frame 310. The pusher element 300 can retract the localization element 116 back into the delivery needle 104 as long as the eyelet frame 310, the narrow portion 312, or combinations thereof do not disengage from the pusher tip 302 of the pusher element 300. The eyelet frame 310 can disengage from the pusher tip 302 when the eyelet frame 310 is displaced out of the window 304 of the pusher element 300. The narrow portion 312 can disengage from the pusher tip 302 when the narrow portion 312 and eyelet frame 310 are no longer surrounded by the distal portion of the pusher element 300. When the localization element resides within the tissue of the patient, the shape memory of the localization element causes the proximal portion of the localization element to pull away from the pusher tip 302 once the narrow portion 312 and eyelet frame 310 are no longer constrained by the pusher element 300.

Figure 3C:
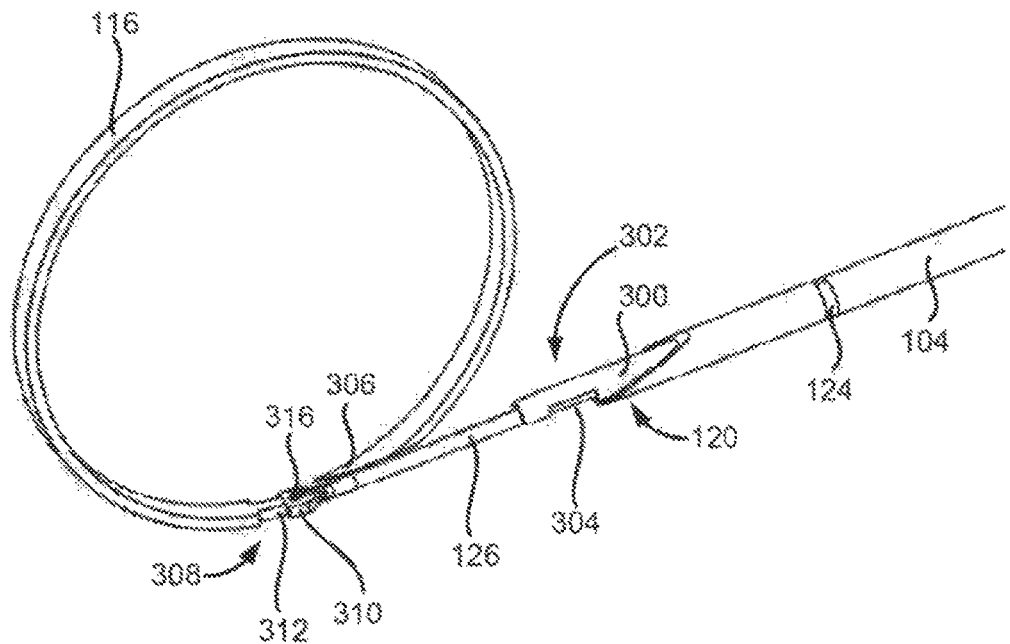
FIG. 3C illustrates a close-up perspective view of a tip of the delivery needle after deployment of the localization element.
Figure 3D:
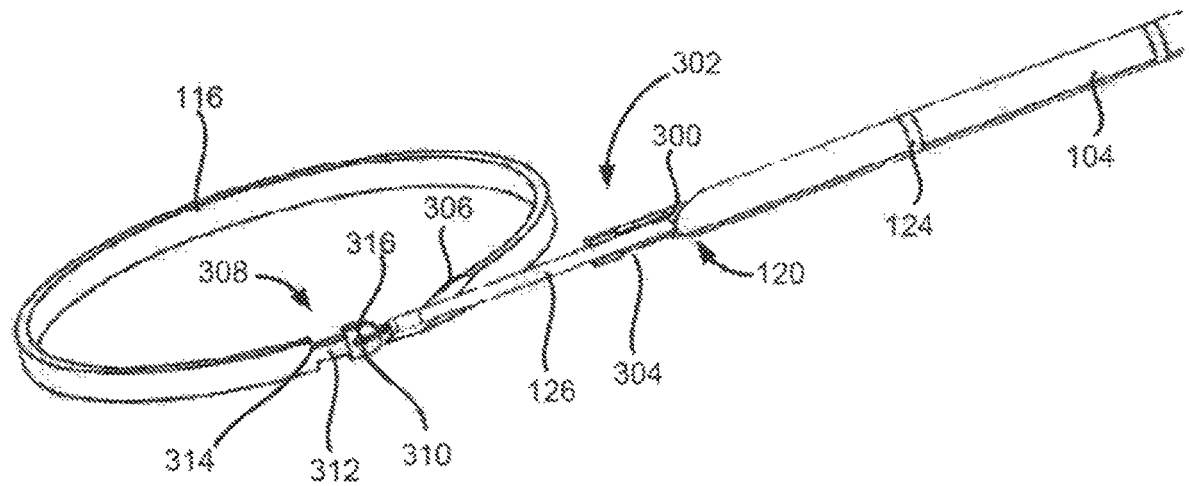
FIG. 3D illustrates a close-up bottom perspective view of the tip of the delivery needle after deployment of the localization element.
Figure 3E:
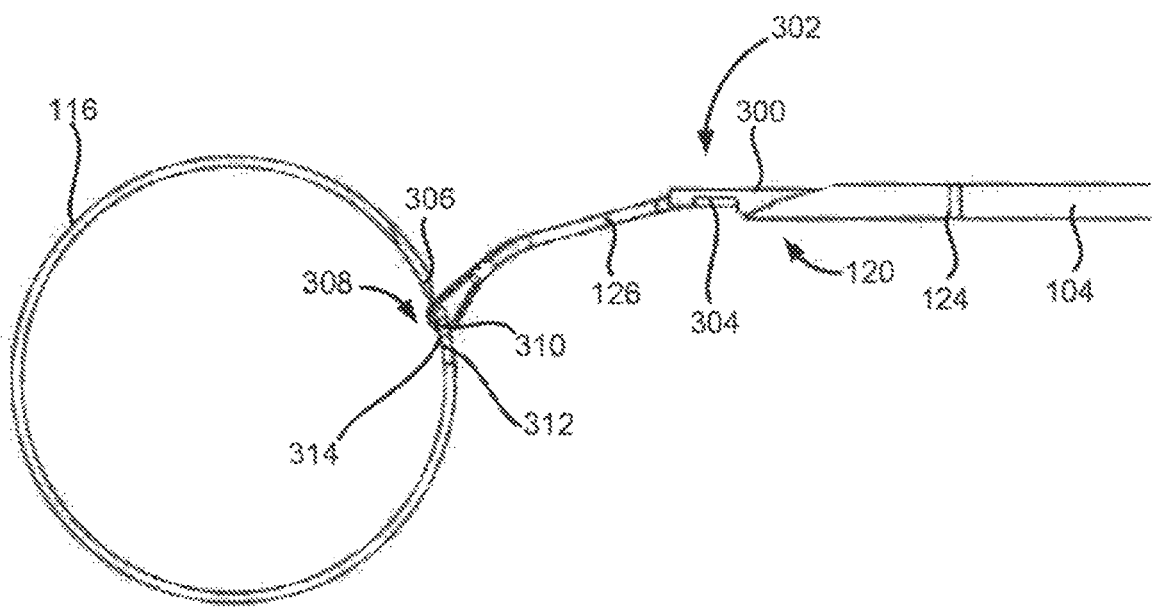
FIG. 3E illustrates a close-up side view of the tracking wire being pulled out of the delivery needle after deployment of the localization element.
Figure 3F:
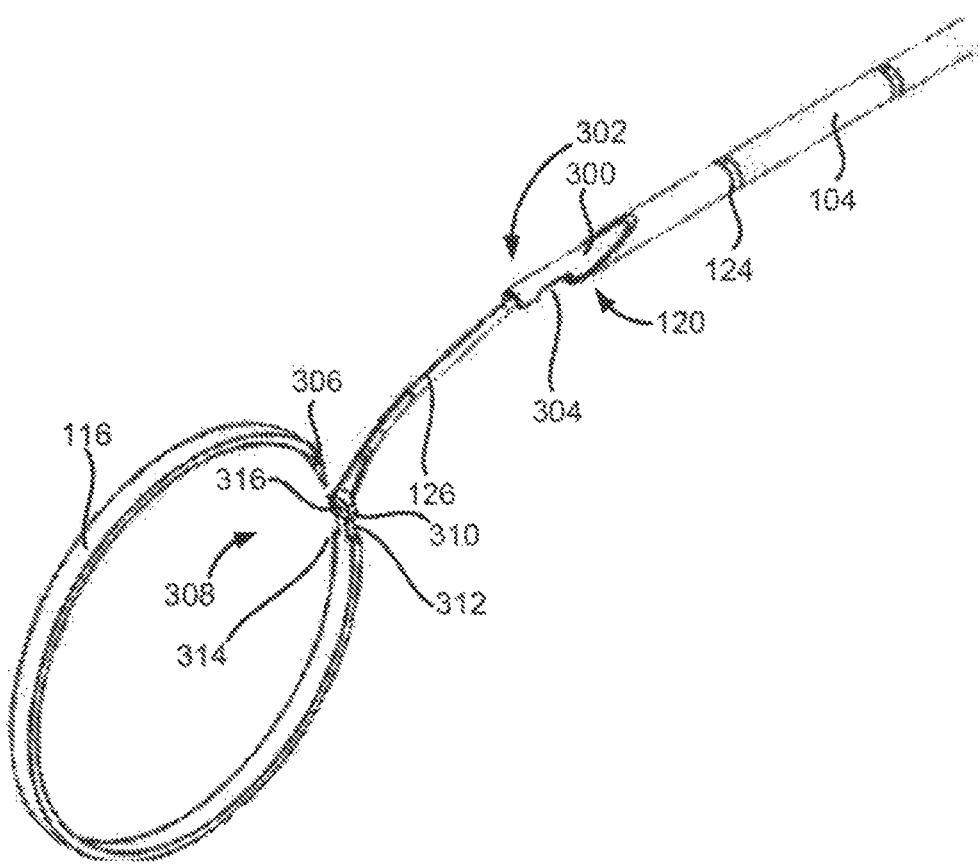
FIG. 3F illustrates a close-up perspective view of the tracking wire being pulled out of the delivery needle after deployment of the localization element.

FIGS. 3C-3F illustrate that the localization element 116 can be deployed when the pusher tip 302 of the pusher element 300 no longer engages with the element base 308. FIGS. 3C and 3D also illustrate that the tracking wire 126 can be pulled through the pusher element 300, the delivery needle 104, or combinations thereof once the localization element 116 is deployed. The tracking wire 126 can be pulled through the pusher element 300, the delivery needle 104, or combinations thereof when the user retracts the delivery needle 104 out of the patient after the localization element 116 is deployed. The entire length of the tracking wire 126 can be pulled through the handle 102, the delivery needle 104, the pusher element 300, or combinations thereof once the user has fully retracted the delivery needle 104 out of the patient.

Figure 4A:
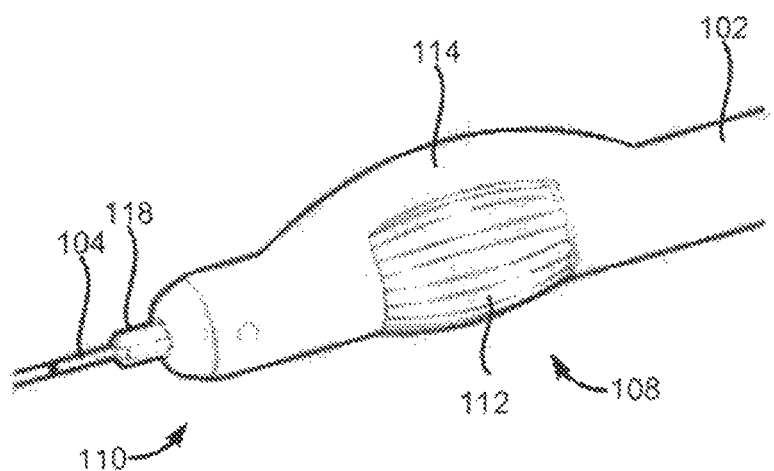
FIG. 4A is a perspective view of a knob and handle of the tissue localization device.

FIG. 4A illustrates that the tissue localization device 100 can be controlled by the knob 112. A user can rotate the knob 112 in the first rotational direction 204 to advance the localization element 116 toward the needle tip 120 or out of the delivery needle 104. A user can also rotate the knob 112 in the second rotational direction 208 to retract the localization element 116 back into the needle tip 120 or further into the delivery needle 104. The localization element 116 can be advanced or retracted when the pusher tip 302 of the pusher element 300 pushes or pulls, respectively, on the element base 308 of the localization element 116.

Figure 4B:
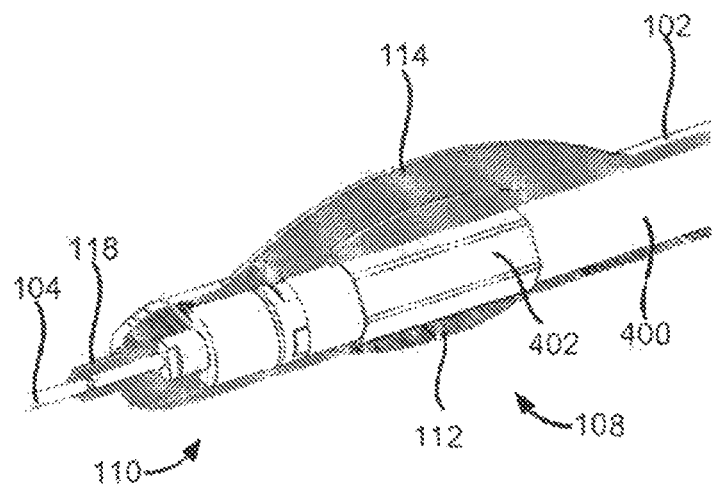
FIG. 4B is a cutaway view illustrating a part of the interior of the tissue localization device.

FIG. 4B illustrates that the tissue localization device 100 can have a drive pipe 400 positioned within the handle 102. The drive pipe 400 can extend from the handle grip 106 to the handle nose 110. The drive pipe 400 can rotate within the handle grip 106. A portion of the drive pipe 400 along the knob portion 108 can be surrounded or defined by an inner barrel 402. The inner barrel 402 can be configured to interact with the knob 112 to allow the knob 112 to rotate the drive pipe 400.

For example, a user can rotate the knob 112 in a first rotational direction 204 to rotate the drive pipe 400 in the same first rotational direction 204. Also, for example, the user can rotate the knob 112 in a second rotational direction 208 to rotate the drive pipe 400 in the same second rotational direction 208.

The drive pipe 400 can be fabricated from or made of a polymer such as an injection molded polymer. For example, the drive pipe 400 can be composed of or comprise acrylonitrile butadiene styrene (ABS) plastic, polycarbonate, polypropylene (PP), or combinations thereof. The drive pipe 400 can also be fabricated from or include parts fabricated from metals or metal alloys such as stainless steel.

Figure 5A:
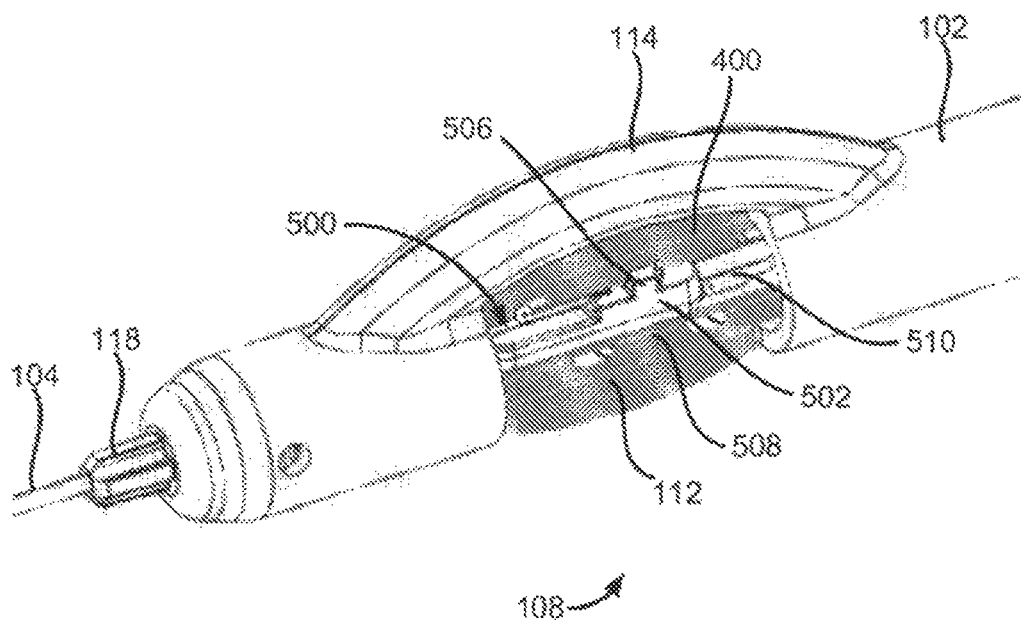
FIG. 5A is a cutaway view illustrating another part of the interior of the tissue localization device.

FIG. 5A illustrates that the drive pipe 400 can have a pipe lumen 500. The pipe lumen 500 can be the interior or inside surface of the drive pipe 400. FIG. 5A also illustrates that the tissue localization device 100 can have a car 502 residing inside the pipe lumen 500. The car 502 can be a component of the tissue localization device 100 configured to maneuver (e.g., push or pull) the pusher element 300. The car 502 can be shaped as an elliptic cylinder having a trivial height dimension. For example, the car 502 can be shaped as an elliptic cylinder having a height dimension of between 1.0 mm and 4.5 mm. In other variations, the car 502 can be shaped as a flattened rectangle, an oval disc, a circular disc, or combinations thereof.

The car 502 can be within a car track 510. The car track 510 can be an elongate channel segment having a surface and walls that support the car 502 as the car 502 slides along the central, longitudinal axis of the handle. The car track 510 can be part of a rod or shaft having a concavity or depression along a longitudinal length of the rod or shaft. The car 502, or a portion therein, can fit within the concavity or depression of the car track 510. The car track 510 can be coupled to the delivery needle 104. In other variations, the car track 510 can be separate from the delivery needle 104. The car track 510 can reside or be disposed in the pipe lumen 500. The car track 510 can remain stationary as the drive pipe 400 rotates.

The pusher element 300 can be attached to the car 502. The pusher element 300 can be fixedly attached to the car 502 via adhesives, interference fit, screws, or combinations thereof. The pusher element 300 can be attached to the car 502 by being threaded or molded through the body of the car 502. The pusher element 300 can be attached to a car front portion 504. The car front portion 504 can be an end or segment of the car 502 proximal to the handle nose 110. The pusher element 300 can be attached to, contiguous with, or extend out from the car front portion 504.

The car 502 can include a car tooth 506. The car tooth 506 can be a projection or protuberance extending out of the car 502. The car tooth 506 can extend out vertically in a direction perpendicular to a longitudinal axis of the tissue localization device 100. The car tooth 506 can also extend out in the direction of the apex or top of the orientation arch 114. The car tooth 506 can be shaped as a cube or a trapezoid. The car tooth 506 can have rounded or beveled edges or corners. In other variations, the car tooth 506 can be ovoid, half-spherical, conical, frustoconical, or combinations thereof.

Figure 5B:
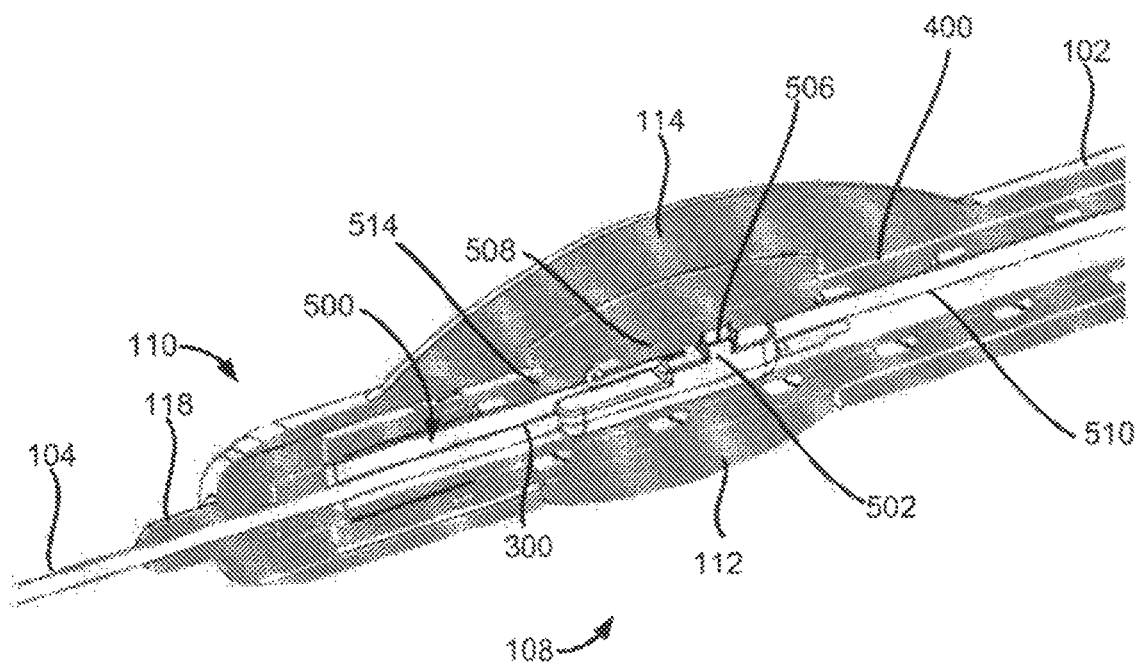
FIG. 5B is a cutaway view illustrating yet another part of the interior of the tissue localization device.

FIGS. 5A and 5B illustrate that the pipe lumen 500 can include a spiral channel that extends radially inward from the surface of the pipe lumen into the inner surface of the drive pipe 400. Solid material between the spiral channels is shown for example as region 508.

As the knob is turned in one rotational direction, it causes the spiral channel to advance the car, thereby advancing the pusher tube, thereby causing the localization element 116 to advance from within the delivery needle 104. When the knob is manually turned in the opposite rotational direction, the process is reversed, causing the localization element 116 to retract within the delivery needle 104.

Figure 5C:
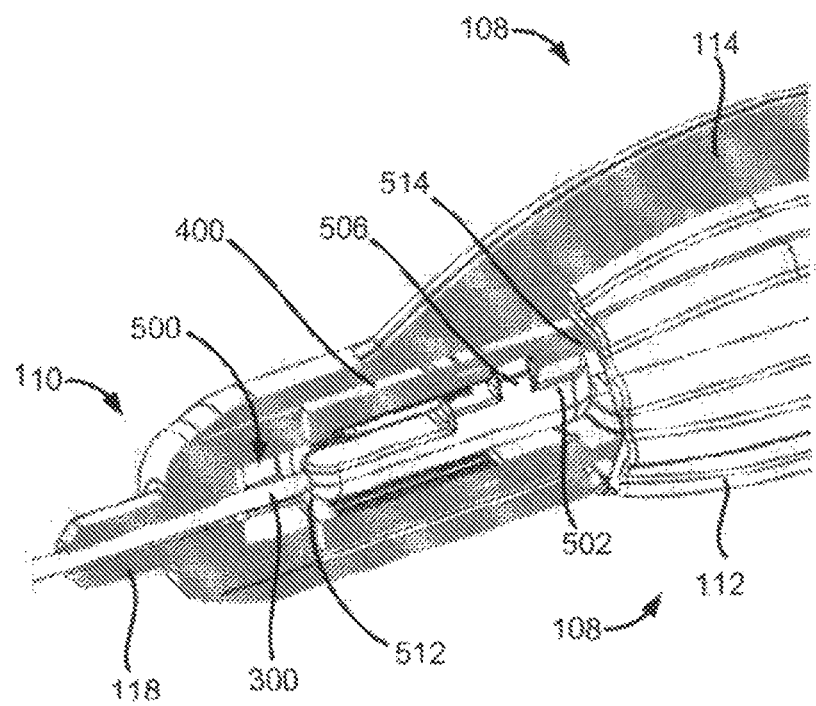
FIG. 5C is a cutaway view illustrating another part of the interior of the tissue localization device.

FIG. 5C illustrates that the car 502 can be propelled by the drive pipe 400 until the car 502 reaches the end of the pipe lumen 500 at the handle nose 110 of the handle 102. The car 502 can come to a stop when the car tooth 506 is passed to an end gear 514. The end gear 514 can be the protruding gear 508 closest to the nozzle end 118. The end gear 514 can be the last protruding gear 508 in the pipe lumen 500 before the end of the pipe lumen 500.

The car 502 can come to a stop or be prevented from moving when the car front portion 504 makes contact with or pushes against a car stop 512. The car stop 512 can be a stationary raised edge or protruding surface feature at the end of the pipe lumen 500 proximal to the luer end 118. In other variations, the car stop 512 can be a separate stationary component of the tissue localization device 100 coupled to the nozzle end 118.

The drive pipe 400, the knob 112, or combinations thereof can be prevented from rotating further in the first rotational direction 204 when the car 502 reaches the car stop 512. The drive pipe 400, the knob 112, or combinations thereof can be prevented from rotating in the first rotational direction 204 when the end gear 514 pushes against the car tooth 506 of the stopped car 502. The car tooth 506 of the stopped car 502 can block the further angular rotation of the end gear 514.

The drive pipe 400 can be rotated in the second rotational direction 208 to push the car 502 away from the car stop 512 and toward the opposite end of the pipe lumen 500. When the drive pipe 400 is rotated in the second rotational direction 208, the end gear 514 can also rotate in the second rotational direction 208 and apply a force to the car tooth 506 in the direction of handle grip 106.

Figure 6A:
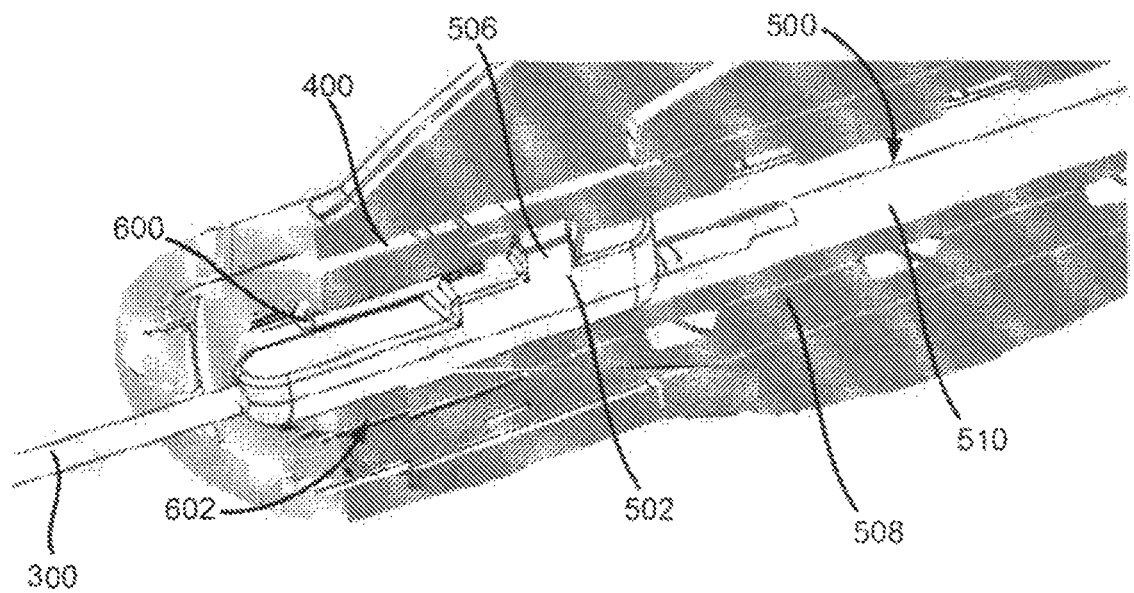
FIG. 6A is a cutaway view illustrating a tactile and/or audible feedback mechanism of the tissue localization device.
Figure 6B:
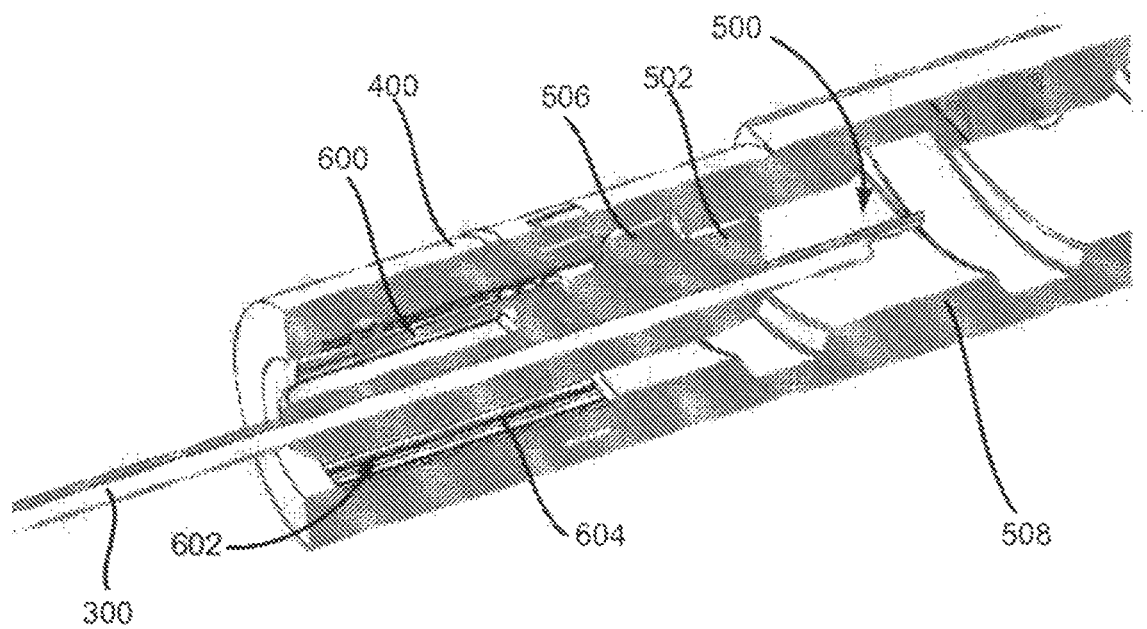
FIG. 6B is another cutaway view illustrating the tactile and/or audible feedback mechanism of the tissue localization device.

FIGS. 6A and 6B illustrate that the tissue localization device 100 can include a rotational alert 600, such as a tactile feedback or sound-generating alert. The rotational alert 600 can be configured to generate an audible and/or tactile signal or indication to a user of the tissue localization device 100 that the localization element 116 is about to deploy and detach and no longer instantly retractable. The signal or indication can include tactile clicking or vibration, audible clicking noises, tapping sensations and/or noises, grinding sensations and/or noises, increased rotational resistance, squealing, scraping, scratching, or combinations thereof. The rotational alert 600 can include a rod, a pin, a hook, a spring, or combinations thereof protruding from the car front portion 504.

The drive pipe 400 can include a grooved section 602. The grooved section 602 can be a portion of the drive pipe 400 having longitudinal grooves 604 around a circumference of the pipe lumen 500. The rotational alert 600 can interact with the longitudinal grooves 604 to generate the audible and/or tactile signal. The rotational alert 600 can interact with the longitudinal grooves 604 when the car 502 enters the grooved section 602. The grooved section 602 can be in the vicinity of the car stop 512. The rotational alert 600 can interact with the longitudinal grooves 604 as the pipe lumen 500 rotates in the first rotational direction 204, the second rotational direction 208, or combinations thereof. The pipe lumen 500 can rotate the longitudinal grooves 604 in the first rotational direction 204, the second rotational direction 208, or combinations thereof. The rotational alert 600 can tap or drag against the longitudinal grooves 604 to generate the detectable audible and/or tactile signal.

The rotational alert 600 can generate the audible and/or tactile signal to inform the user that the car 502 has pushed the pusher tip 302 of the pusher element 300 out of the delivery needle 104. The audible and/or tactile signal can also indicate that the element base 308 of the localization element 116 can soon become dislodged or separated from the pusher tip 302 of the pusher element 300.

The grooved section 602 can be a portion of the drive pipe 400 in the handle nose 110 of the handle 102. The rotational alert 600 can generate the audible and/or tactile signal until the car reaches the car stop 512.

Figure 6C:
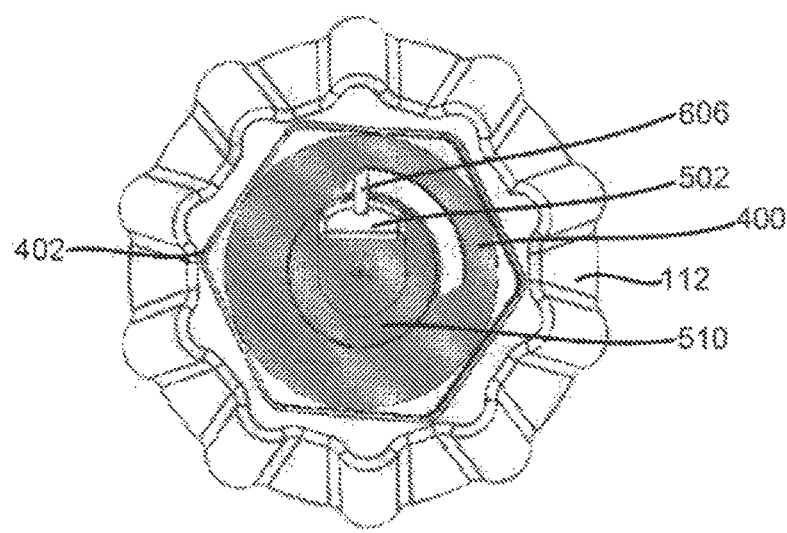
FIG. 6C is a front cutaway view illustrating the tactile and/or audible feedback mechanism of the tissue localization device.
Figure 6D:
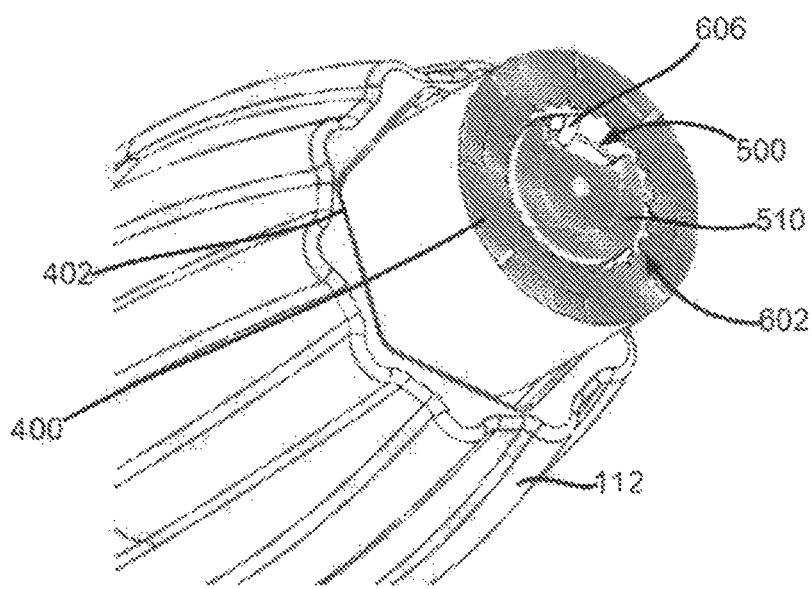
FIG. 6D is a perspective cutaway view illustrating the tactile and/or audible feedback mechanism of the tissue localization device.
Figure 6E:
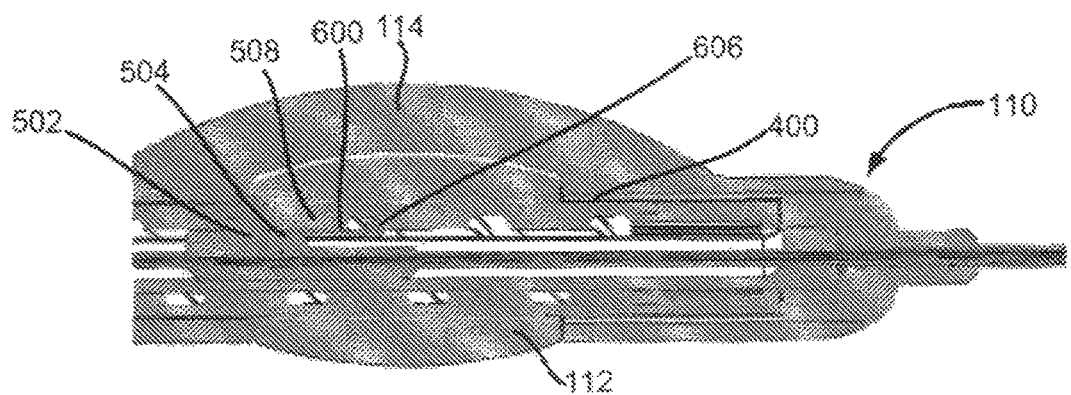
FIG. 6E is a side cross-sectional view illustrating the tactile and/or audible feedback mechanism of the tissue localization device.

FIGS. 6C, 6D, and 6E illustrate that the rotational alert 600 can have a rotational alert tip 606. The rotational alert tip 606 can be an end of the rotational alert 600 distal to the car front portion 504. The rotational alert tip 606 can be a curved or coiled tip of an elongate rod representing the body of the rotational alert 600. FIGS. 6C, 6D, and 6E illustrate that the rotational alert 600, the rotational alert tip 606, or combinations thereof can proceed down the pipe lumen 500 without generating any noticeable audible and/or tactile alert signals or noises as the car 502 is pushed through the pipe lumen 500 toward the handle nose 110.

Figure 6F:
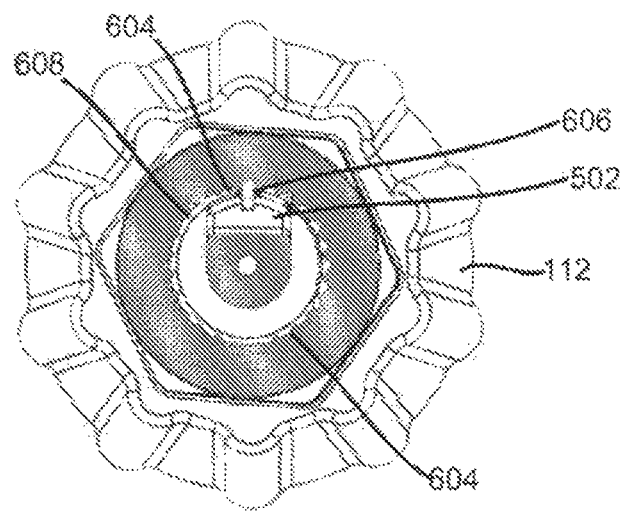
FIG. 6F is a front cutaway view illustrating the tactile and/or audible feedback mechanism of the tissue localization device.
Figure 6G:
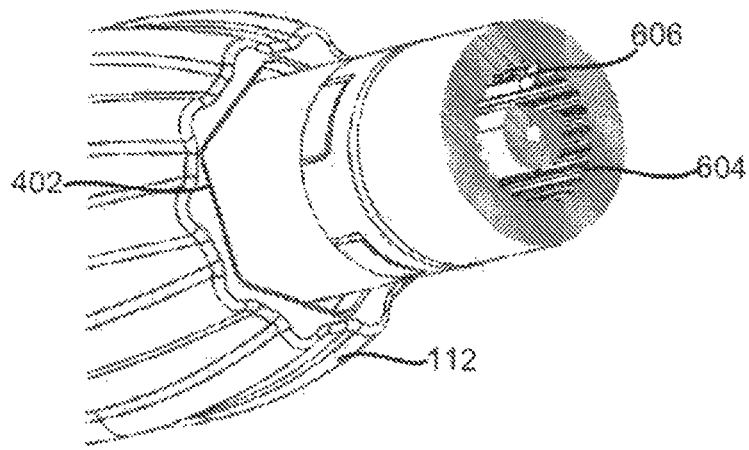
FIG. 6G is a perspective cutaway view illustrating the tactile and/or audible feedback mechanism of the tissue localization device.
Figure 6H:
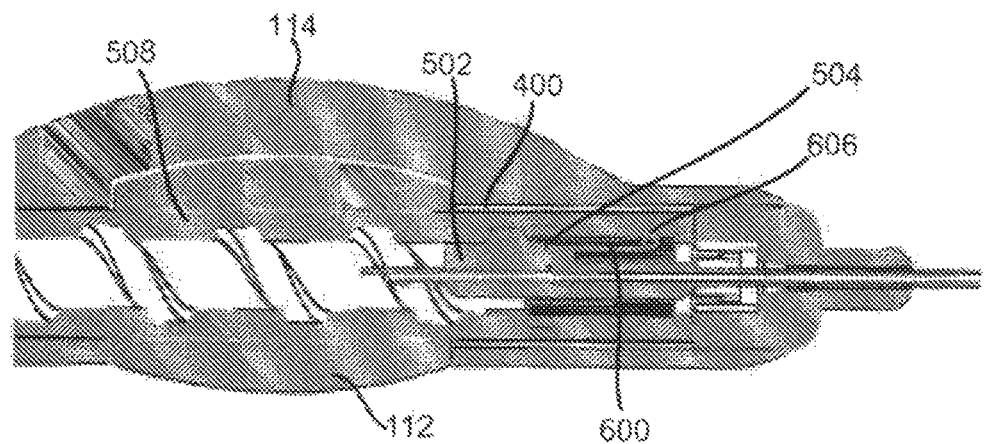
FIG. 6H is a side cross-sectional view illustrating the tactile and/or audible feedback mechanism of the tissue localization device.

FIGS. 6F, 6G, and 6H illustrate that the rotational alert tip 606 can be positioned within a longitudinal groove 604 when the rotational alert 600 enters the grooved section 602 of the drive pipe 400. The grooves section 602 can have longitudinal ridges 608 separated by longitudinal grooves 604. The longitudinal ridges 608 can protrude radially inward toward the center of the pipe lumen 500.

The rotational alert 600 can generate an audible and/or tactile signal or feedback when the drive pipe 400 is rotated in either the first rotational direction 204 or the second rotational direction 208 when the rotational alert tip 606 is in the grooved section 602. The rotational alert 600 can generate the audible and/or tactile signal or feedback as the rotational alert tip 606 makes contact with the longitudinal ridges 608, the longitudinal grooves 604, or combinations thereof as the drive pipe 400 is rotated.

Figure 6I:
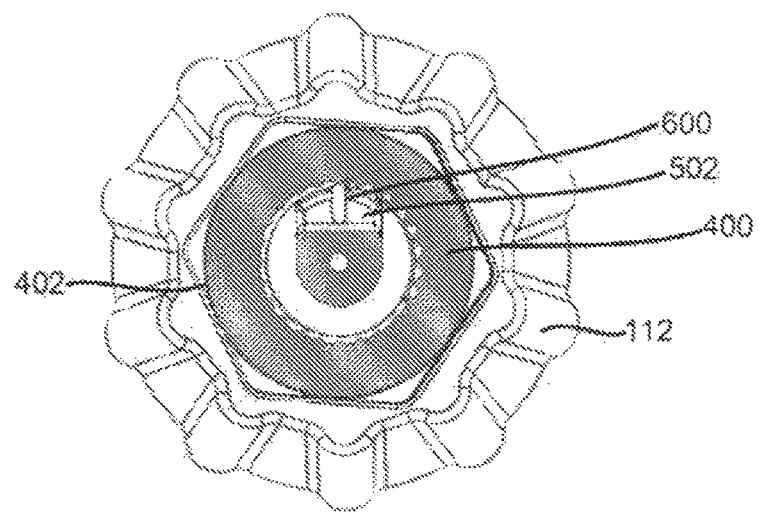
FIG. 6I is a front cutaway view illustrating the tactile and/or audible feedback mechanism of the tissue localization device.
Figure 6J:
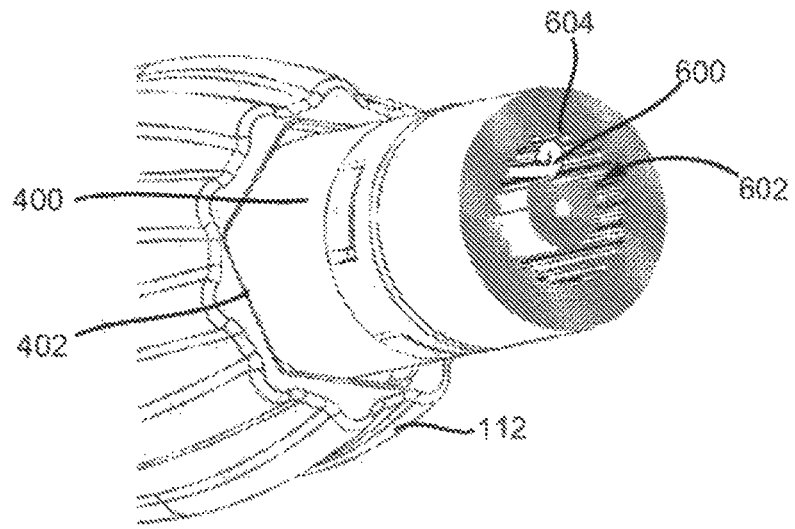
FIG. 6J is a perspective cutaway view illustrating the tactile and/or audible feedback mechanism of the tissue localization device.
Figure 6K:
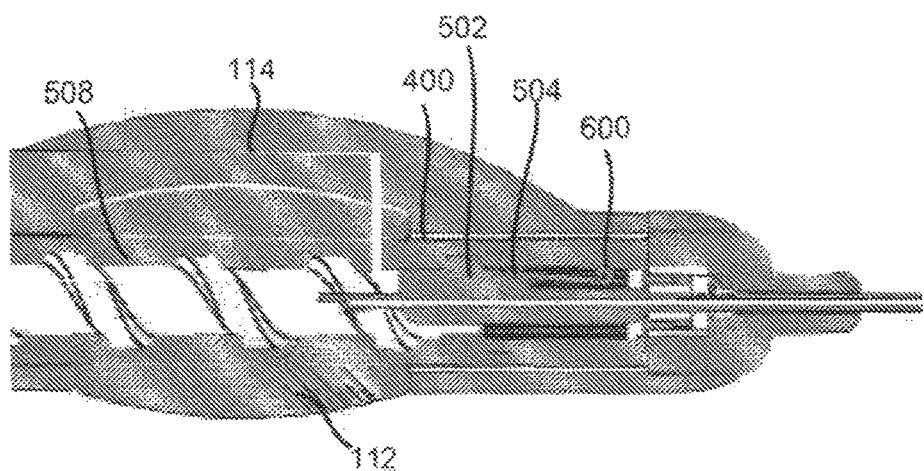
FIG. 6K is a side cross-sectional view illustrating the tactile and/or audible feedback mechanism of the tissue localization device.

FIGS. 6I, 6J, and 6K illustrate that the rotational alert tip 606 can be deflected by the longitudinal ridges 608 when the drive pipe 400 is rotated in either the first rotational direction 204 or the second rotational direction 208. The rotational alert tip 606 can be deflected when the rotational alert 600 is pushed radially inward by the longitudinal ridges 608. For example, when the rotational alert 600 is a rod having a curved or hooked end representing the rotational alert tip 606, the curved or hooked end can be deflected by the longitudinal ridges 608 as the drive pipe 400 is rotated by the knob 112. In this example, the rod and the curved or hooked end can be pushed radially inward when the curved or hooked end is deflected by the longitudinal ridges 608.

Figure 7:
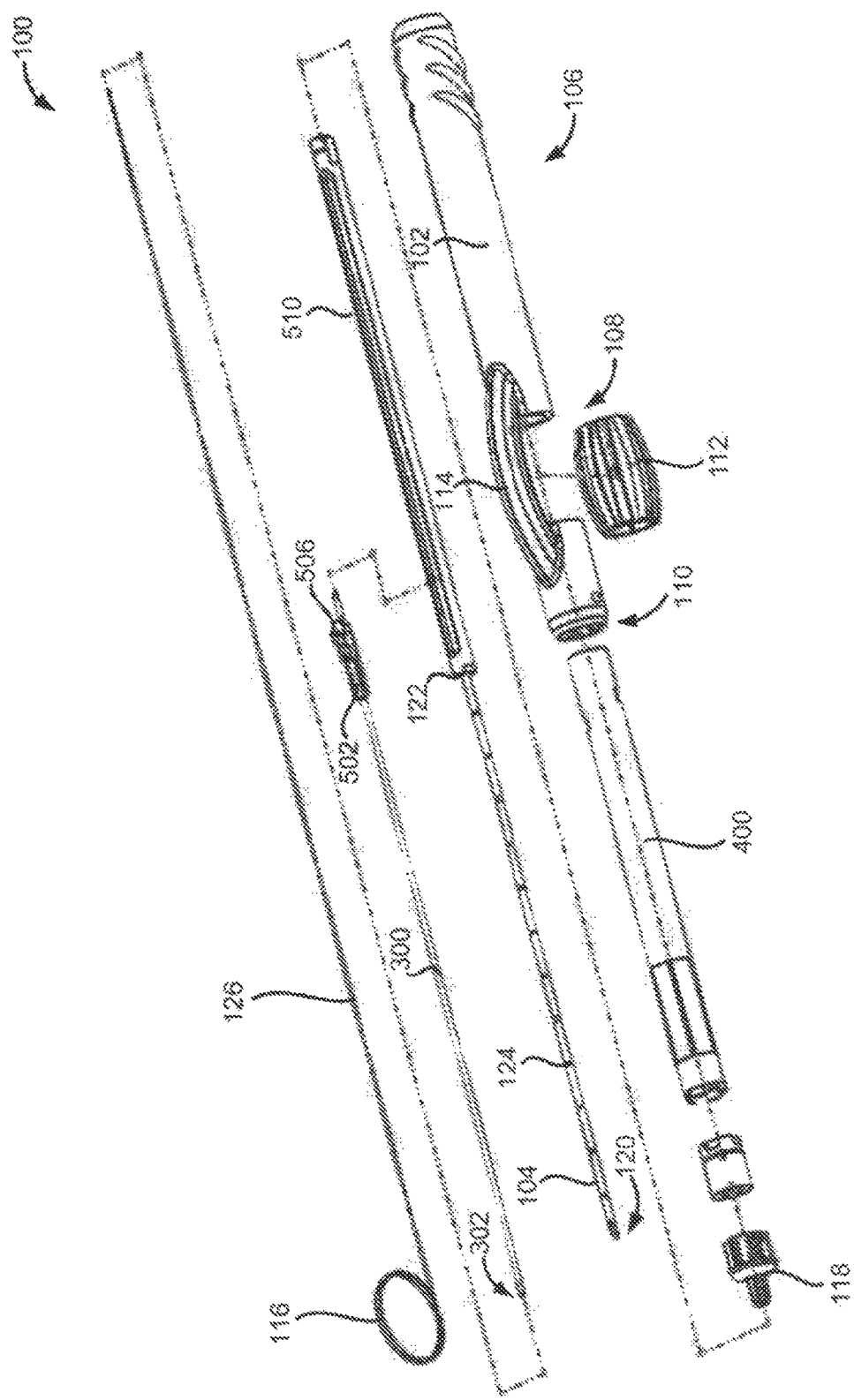
FIG. 7 is an exploded view of the tissue localization device.

FIG. 7 illustrates that the drive pipe 400 can be positioned within the handle 102 when the tissue localization device 100 is in an assembled state. The car track 510 can be coupled to the delivery needle 104 and both the car track 510 and the delivery needle 104 can be positioned within the drive pipe 400 when the tissue localization device 100 is in the assembled state. The car 502 can be fixedly attached to the pusher element 300. The pusher element 300 can be threaded through the delivery needle 104 and can be positioned in the delivery needle 104 when the tissue localization device 100 is in the assembled state. The localization element 116 can be coupled to the tracking wire 126. The tracking wire 126 can be threaded through the pusher element 300 before the pusher element 300 is inserted into the delivery needle 104. The localization element 116 can be removably attached to the pusher tip 302 of the pusher element 300. The localization element 116 can also be pressed into a straightened configuration to be inserted into the delivery needle 104.

Figure 8A:
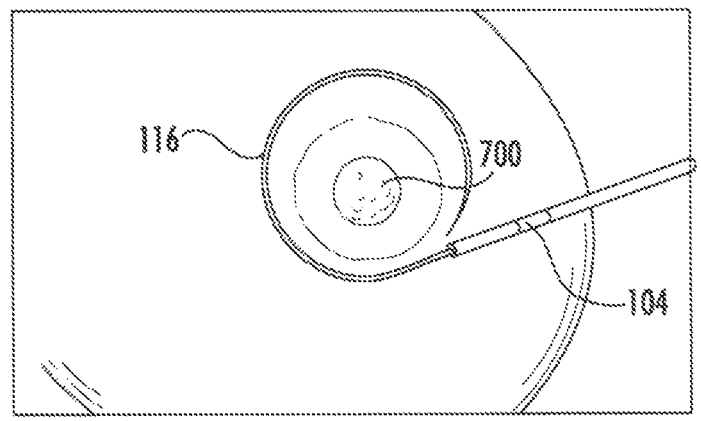
FIG. 8A illustrates a target tissue region, the localization element and the delivery needle inside a patient tissue model.

FIG. 8A illustrates that the localization element 116 can surround a target tissue 700, for example having or being a target tissue mass, when deployed in a patient tissue model. The localization element 116 can cut through the patient's tissue, such as a breast tissue or lung tissue, as the pusher element 300 and the car 502 are pushed longitudinally through the pipe lumen 500. The localization element 116 can curve into the predetermined shape 202 to surround and mark the target tissue 700. The predetermined shape 202 can be a circular shape. The localization element 116 can be deployed from the tissue localization device 100 when the eyelet frame 310 of the localization element 116 is dislodged or otherwise becomes separated from the window 304 of the pusher element 300. In addition, the localization element 116 can be deployed when the narrow portion 312 of the localization element 116, the shoulder 314, or combinations thereof is separated from the pusher tip 302 of the pusher element 300.

The user can complete the deployment of the localization element 116 by retracting the delivery needle 104, the pusher element 300, or combinations thereof completely out of the patient's tissue site. The localization element 116 can become anchored in the implantation site of the patient's tissue as the localization element 116 is separated from the rest of the tissue localization device 100.

Figure 8B:
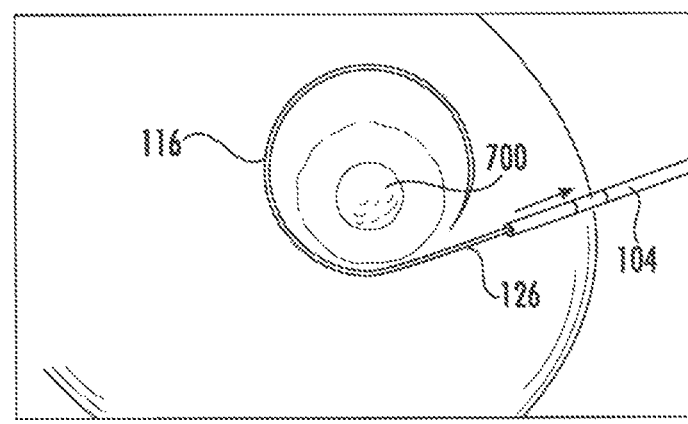
FIG. 8B illustrates the localization element surrounding a target tissue region or mass and the delivery needle exiting the patient tissue model.

FIG. 8B illustrates that the end of the tracking wire 126 coupled to the localization element 116 can remain in the patient's tissue prior to removal of the delivery needle 104 from the tissue site. The tracking wire 126 can serve as a path or trail for informing a surgeon of the path taken by the delivery needle 104 into the patient's appendage. The tracking wire 126 can also serve as a path or trail for indicating the location of the target tissue region delineated by the curved localization element 116.

Figure 8C:
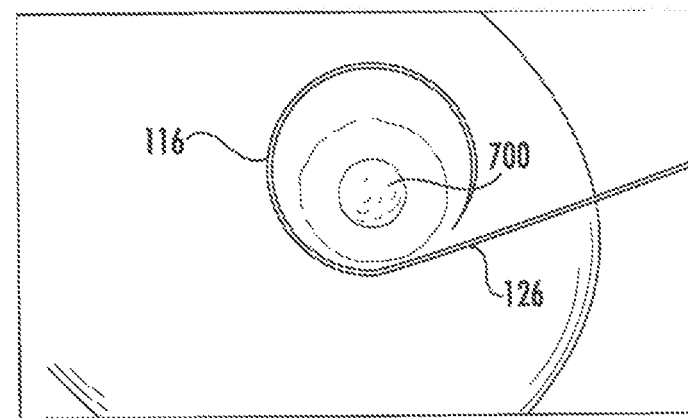
FIG. 8C illustrates the localization element surrounding the target tissue region and a distal end of the tracking wire positioned outside of the patient tissue model.

FIG. 8C illustrates that the end of the tracking wire 126 not attached or coupled to the localization element 116 can emerge from the patient's skin after the delivery needle is removed. This exposed segment of the tracking wire 126 can be allowed to extend from the patient and because the wire 126 is flexible, the wire 126 can comfortably reside on the patient's skin (with or without coiling it) and secured by, for example, adhesive dressing to the patient's skin. For example, the exposed segment of the tracking wire 126 can be taped by surgical tape to the patient's appendage. The exposed segment of the tracking wire 126 can also be coiled, folded, twisted, or cut before or after being taped to the patient's skin or dressing. The flexible nature of the tracking wire 126 enables the patient to be comfortable while the localization element remains in situ, with minimal risk of dislodgement of the localization element. This feature allows for logistic flexibility in planning for the surgical removal of the localized tissue (e.g. place the localization element on one day and remove the tissue specimen and localization element on a subsequent day).

Although not shown in the figures, it is anticipated by this disclosure that multiple localization elements 116 can be used to mark or surround the suspect tissue mass in three dimensions.

Figure 9:
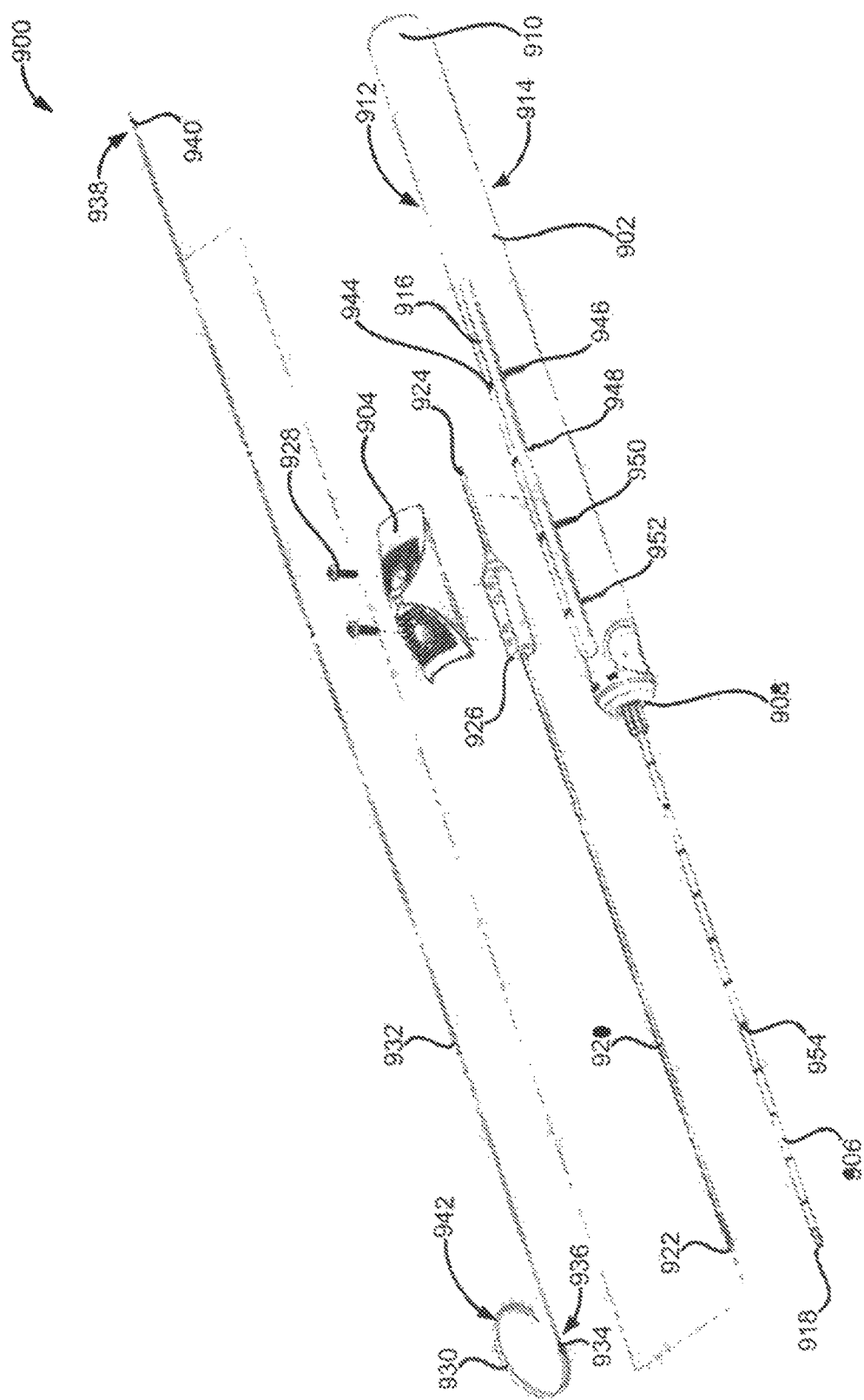
FIG. 9 illustrates an exploded view of another variation of the tissue localization device.

FIG. 9 illustrates that the tissue localization device 900 can have a handle 902 with a slidable delivery control 904 and a delivery needle 906 extending out from the handle 902. The handle 902 can be shaped as a cylinder, a tube, a rod, an elongate ovoid, an ellipsoid, a cone, or combinations thereof. The handle 902 can comprise finger grooves, holes, indentations, or combinations thereof. The handle 902 can be sized or shaped such that a user can grasp the handle 902 with one hand. The handle 902 can comprise or be composed of acrylonitrile butadiene styrene (ABS) plastic, polycarbonate, polypropylene (PP), or other suitable polymers, or combinations thereof. The handle 902 can also comprise components fabricated from metals or metal alloys such as stainless steel.

The handle 902 can have a handle distal end 908, a handle proximal end 910 opposite the handle distal end 908, a handle dorsal side 912, a handle ventral side 914 opposite the handle dorsal side 912, and an elongate slot 916 defined along the handle dorsal side 912.

The handle distal end 908 can include a nozzle or luer end. The luer end can fixedly secure a packaging needle cover (not shown in FIG. 9) to protect the delivery needle 906.

The delivery needle 906 can also have a needle lumen 918 and a pusher element 920 slidably translatable within the needle lumen 918. The delivery needle 906 can comprise or be composed of a metal, metal alloy, or a rigid medical grade polymer. When the delivery needle 906 is made of a polymer, the delivery needle 906 can be covered with a radiopaque material or coating. The pusher element 920 can have a pusher distal end 922 and a pusher proximal end 924 opposite the pusher distal end 922.

The pusher element 920 can have a pusher plug 926 affixed near the pusher proximal end 924. The pusher plug 926 can be affixed to a stationary position along the pusher element 920. The pusher plug 926 can have a number of threaded bores or holes defined along a dorsal surface of the pusher plug 926. The delivery control 904 can be connected to the pusher element 920 via fasteners 928 screwed into the threaded bores or holes of the pusher plug 926. At least a portion of each of the fasteners 928 can extend through the elongate slot 916 when the delivery control 904 is coupled to the pusher element 920. In other variations, the delivery control 904 can be connected to the pusher plug 926 via adhesives, an interference or locking fit, clips, clasps, snap buttons, wire connectors, insert molding, or combinations thereof. The elongate slot 916 can act as a track or guiding lane for the longitudinal translation of the delivery control 904. The delivery control 904 can be pushed toward the handle distal end 908 or pulled toward the handle proximal end 910 to translate the pusher element 920 within the needle lumen 918.

The positioning or orientation of the delivery control 904 relative to the handle 902 can indicate the deployment orientation of the localization element 930 relative to the handle 902. For example, the localization element 930 can deploy toward a side of the tissue localization device 900 on which the delivery control 904 is disposed. Alternatively, the localization element 930 can deploy toward an opposite side of the tissue localization device 900 from the delivery control 904, or the delivery control 904 can have arrows pointing toward a direction of the localization element's deployment.

The tissue localization device 900 can also include a localization element 930 and a flexible tracking wire 932 coupled to the localization element 930. The tracking wire 932 can have a wire distal segment 934 including a wire distal end 936 and a wire proximal segment 938 including a wire proximal end 940.

The localization element 930 can be curled or curved into a deployed configuration 942 when unconstrained by or deployed from the delivery needle 906. The localization element 930 can be pressed or formed into a flat or unfurled configuration when positioned within the needle lumen 918 of the delivery needle 906. The localization element 930 can be initially positioned within the needle lumen 918 when the tissue localization device 900 is in the assembled state. The localization element 930 can slidably translate within the needle lumen 918. As will be discussed in the following sections, the localization element 930 can be detachably held by or can detachably interlock with the pusher element 920 when the localization element 930 is within the needle lumen 918.

FIG. 9 also illustrates that the handle 902 can have a number of deployment stage markers 944. The deployment stage markers 944 can be graphics, etchings, or indents along the outside surface of the handle 902. The deployment stage markers 944 can inform a user of the extent of the deployment of the localization element 930 based on a position of the delivery control 904 relative to the deployment stage markers 944. The deployment stage markers 944 can include a starting marker 946, an initial deployment marker 948, a halfway deployment marker 950, and a deployed marker 952.

The starting marker 946 can be a marker most proximal to the handle proximal end 910. The localization element 930 can be completely within the needle lumen 918 when the delivery control 904 is positioned behind the starting marker 946. The initial deployment marker 948 can be positioned distal to the starting marker 946. At least a portion of the localization element 930 can be located outside of the needle lumen 918 when the delivery control 904 is positioned in between the starting marker 946 and the initial deployment marker 948. The halfway deployment marker 950 can be positioned distal to the initial deployment marker 948. At least half of the length of the localization element 930 can be located outside of the needle lumen 918 when the delivery control 904 is positioned in between the initial deployment marker 948 and the halfway deployment marker 950. The halfway deployment marker 950 can also indicate the point at which the localization element 930 can still be retracted back into the delivery needle 906. The deployed marker 952 can be the marker closest to the handle distal end 908. The localization element 930 can be fully laterally deployed when the delivery control 904 is positioned in between the halfway deployment marker 950 and the deployed marker 952. The deployed marker 952 can also indicate the point at which the localization element 930 can no longer be retracted back into the delivery needle 906.

FIG. 9 also illustrates that the delivery needle 906 can have a number of needle depth markers 954. The needle depth markers 954 can be located in between the needle tip and the needle base. The needle depth markers 954 can be markings, etchings, or surface indentations on the surface of the delivery needle 906. The needle depth markers 954 can assist a user, such as a surgeon, radiologist or other imaging professional, to insert the delivery needle 906 into the tissue of a patient. The needle depth markers 954 can be separated by increments of millimeters, centimeters, inches, or combinations thereof.

Figure 10A:
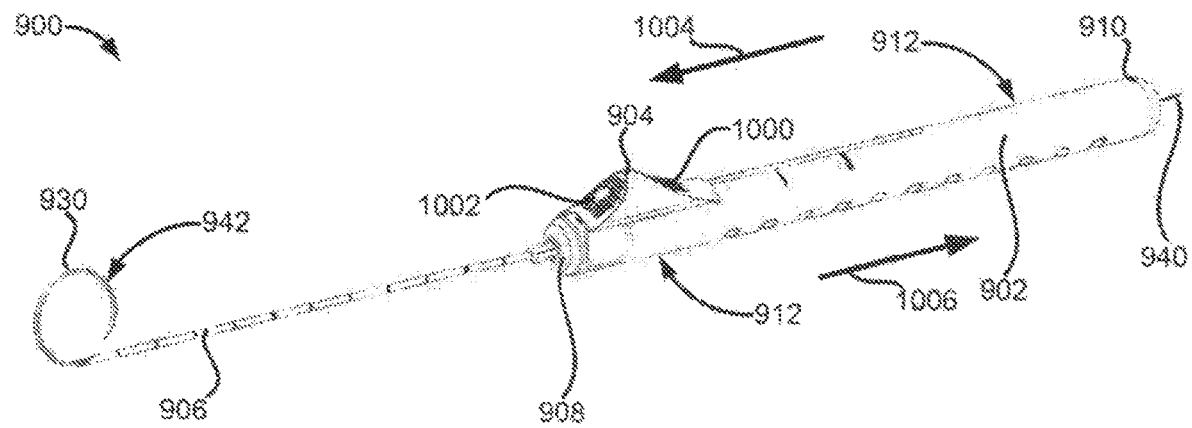
FIGS. 10A and 10B illustrate perspective and side views, respectively, of the assembled tissue localization device of FIG. 9.

FIG. 10A illustrates that the delivery control 904 can include a substantially triangular component having a first interface surface 1000 and a second interface surface 1002. The first interface surface 1000 and the second interface surface 1002 can be sloped or raised. The first interface surface 1000 can be upwardly concave when viewed from the handle proximal end 910 to the handle distal end 908. The second interface surface 1002 can be upwardly concave when viewed from the handle distal end 908 to the handle proximal end 910. In other variations, the first interface surface 1000 and the second interface surface 1002 can be any shape or orientation needed to advance or retract the delivery control 904 with one hand of a user.

A method of operating the tissue localization device 900 can involve a user holding the handle 902 of the tissue localization device 900 using one hand of the user. The method can also involve the user pushing the first interface surface 1000 of the delivery control 904 in a first longitudinal direction 1004 with at least one finger of the same hand holding the handle 902. All references to finger in this disclosure can include one or more digit fingers, a thumb, a part of a finger, or any combinations thereof. The first longitudinal direction 1004 can be a forward direction. For example, the delivery control 904 can be pushed in the first longitudinal direction 1004 from the starting marker 946 to the initial deployment marker 948, the halfway deployment marker 950, or the deployed marker 952. The localization element 930 can be translated through the needle lumen 918 in response to the pushing or withdrawing of the delivery control 904.

In cases where the delivery control 904 is not pushed to the deployed marker 952 or beyond, the method can further involve the user pulling or otherwise applying force to the second interface surface 1002 in the second longitudinal direction 1006. The second longitudinal direction 1006 can be a backward direction opposite the first longitudinal direction 1004. The localization element 930 can be retracted back into the delivery needle 906 or further into the delivery needle 906 in response to the pulling of the delivery control 904.

The user can pull or otherwise apply force to the second interface surface 1002 with at least one finger of the same hand holding the handle 902. In this manner, the tissue localization device 900 can be operated entirely with one hand of the user. This feature is important because, in many cases, the other hand of the user is simultaneously being used to position an ultrasound transducer, thereby enabling the user to position the delivery needle 906 and control the deployment and retraction of the localization element 930 via the handle 902 under simultaneous ultrasound guidance.

Figure 10B:
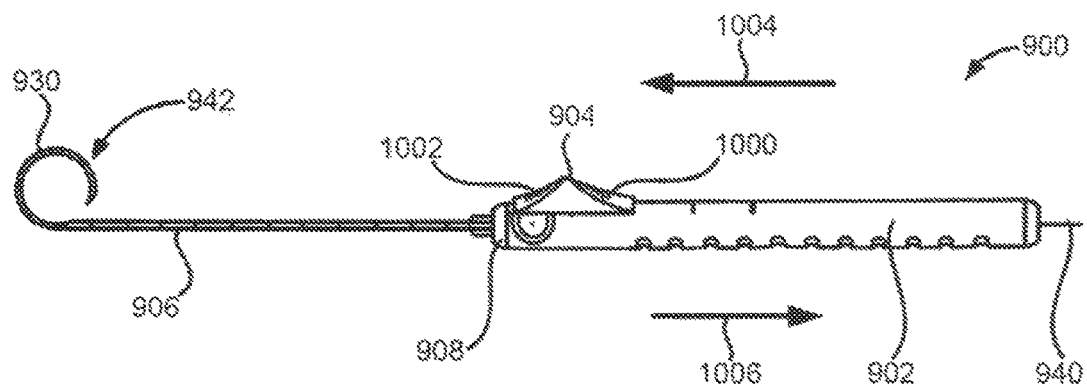

FIG. 10B illustrates that the localization element 930 can be curled into a deployed configuration 942 when the delivery control 904 is translated to the deployed marker 952. FIGS. 10A and 10B also illustrate that at least a segment of the tracking wire 932, such as the wire proximal end 940, can extend out of the handle proximal end 910 when the delivery control 904 is translated to the deployed marker 952. More of the tracking wire 932 can extend out of the handle proximal end 910 as the delivery control 904 is pulled in the second longitudinal direction 1006 toward the handle proximal end 910. The tracking wire 932 can be housed within a lumen of the pusher element 920 when the localization element 930 is detachably held by or detachably interlocks with the pusher element 920.

Figure 10C:
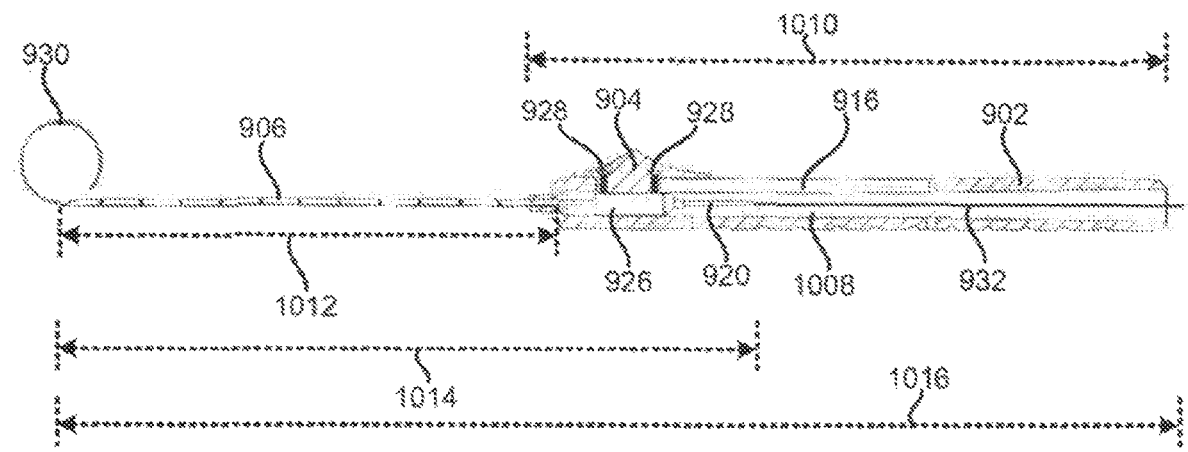
FIGS. 10C and 10D illustrate side and perspective cutaway views, respectively, of the assembled tissue localization device of FIG. 9.

FIG. 10C illustrates that the handle 902 can have a handle lumen 1008. The pusher plug 926 and at least a segment of the pusher element 920 can be housed within the handle lumen 1008. The pusher plug 926 and the pusher element 920 can also translate longitudinally within the handle lumen 1008.

FIG. 10C also illustrates that the handle 902 can have a handle length 1010. For example, the handle length 1010 can be between approximately 12.0 cm and 20.0 cm. The handle length 1010 can be approximately 16.0 cm. FIG. 10C further illustrates that the delivery needle 906 can have a needle length 1012. For example, the needle length 1012 can be between approximately 10.0 cm and 15.0 cm. The needle length 1012 can be approximately 12.0 cm. FIG. 10C also illustrates that the pusher element 920 can have a pusher length 1014. For example, the pusher length 1014 can be between approximately 16.0 cm to 20.0 cm. The pusher length 1014 can be approximately 17.5 cm. FIG. 10C further illustrates that the tracking wire 932 can have a wire length 1016. For example, the wire length 1016 can be between approximately 20.0 cm and 30.0 cm. The wire length 1016 can also be greater than 30.0 cm depending on the location of a target tissue site.

Figure 10D:
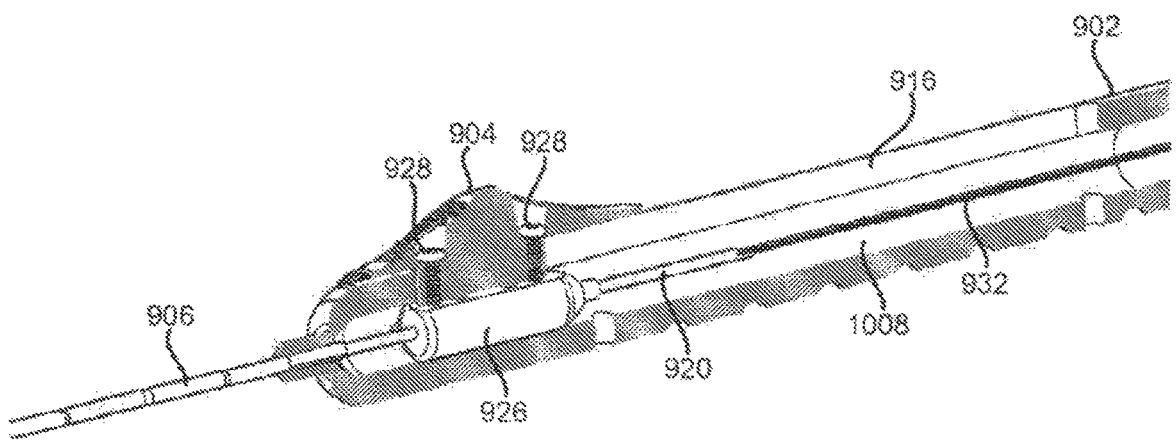

FIG. 10D illustrates that the fasteners 928 can extend into a portion of the delivery control 904 to connect the delivery control 904 to the pusher plug 926 and the pusher element 920. FIG. 10D also illustrates that the elongate slot 916 can provide clearance for the fasteners 928 as the delivery control 904, the pusher plug 926, and the pusher element 920 translate longitudinally in the first longitudinal direction 1004 or the second longitudinal direction 1006. FIG. 10D further illustrates that connecting the delivery control 904 to the pusher element 920 via the pusher plug 926 prevents the pusher element 920 from being translated (e.g., pushed or pulled) entirely out of the handle lumen 1008 or the needle lumen 918. In some variations, the tissue localization device 900 can comprise a gear mechanism and the translation of the pusher element 920 can be facilitated by the gear mechanism.

Figure 11A:
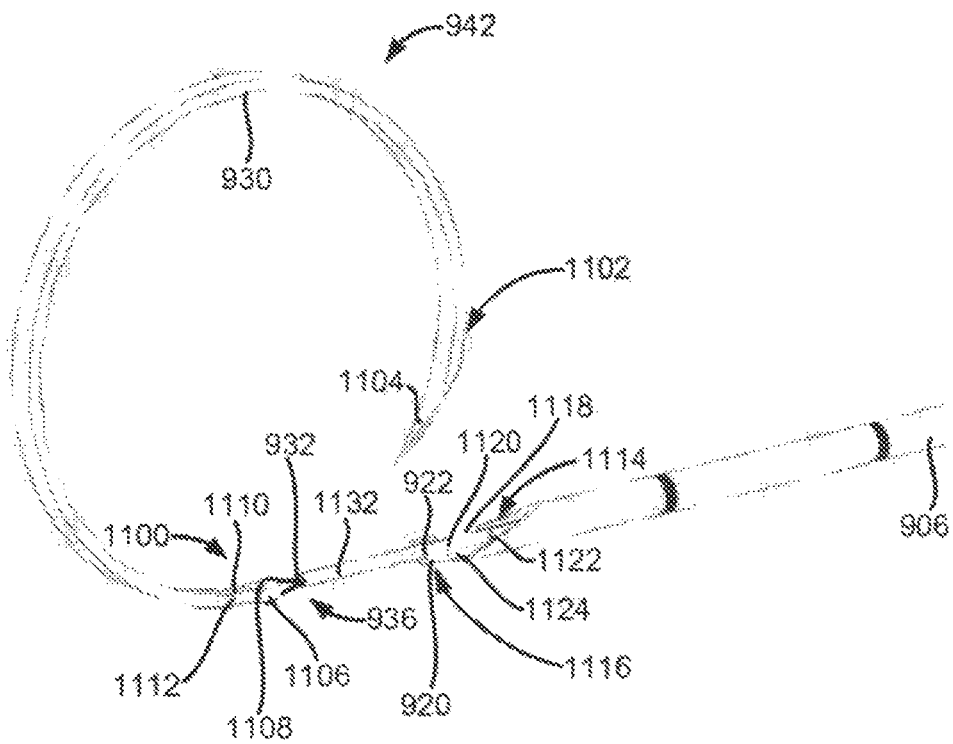
FIGS. 11A and 11B illustrate top and bottom perspective views, respectively, of a localization element detached from a pusher element.
Figure 11B:
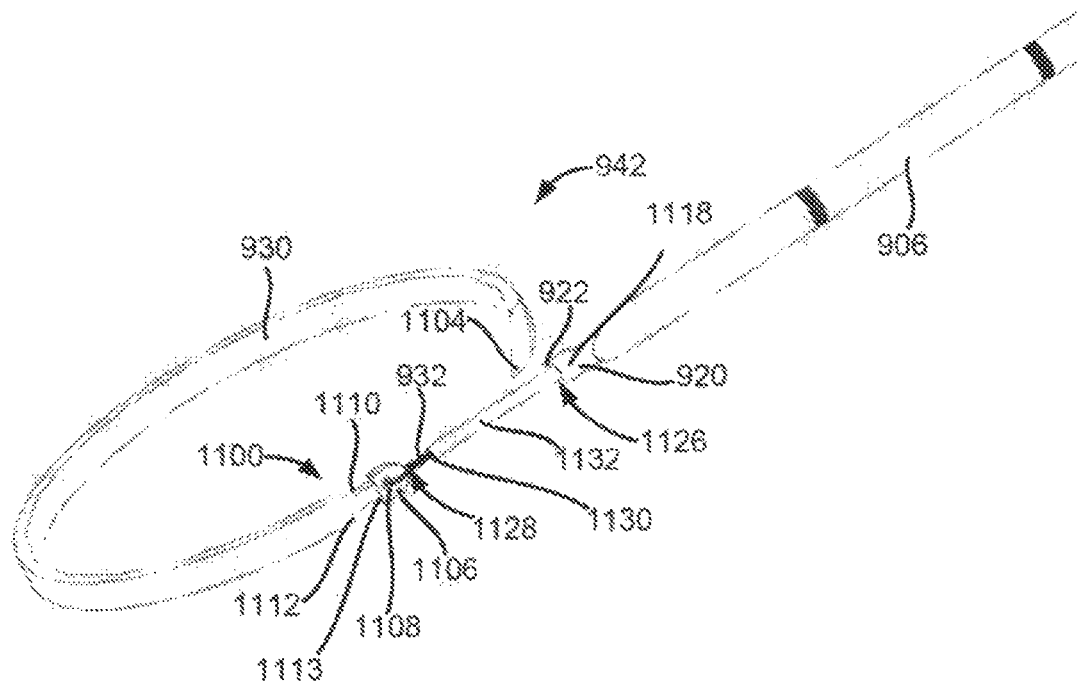

FIGS. 11A and 11B illustrate that the localization element 930 can have a locator proximal end 1100 and a locator distal end 1102. The locator distal end 1102 can have a sharpened locator tip 1104 for piercing through tissue. The locator proximal end 1100 can include an eyelet frame 1106 surrounding an aperture 1108, a narrow portion 1110, and a shoulder portion 1112. The eyelet frame 1106 can be connected to the shoulder portion 1112 by the narrow portion 1110. The aperture 1108 can be positioned substantially in the middle of the eyelet frame 1106. The aperture 1108 can be an opening, hole, or bore configured to receive the tracking wire 932.

FIGS. 11A and 11B also illustrate that the pusher element 920 can have a pusher dorsal side 1114 and a pusher ventral side 1116 opposite the pusher dorsal side 1114. A delivery port 1118 can be defined along the pusher dorsal side 1114 proximal to the pusher distal end 922. The delivery port 1118 can be a cutout along the pusher dorsal side 1114. The eyelet frame 1106 of the localization element 930 can be detachably positioned within the delivery port 1118 of the pusher element 920 when the localization element 930 is within the needle lumen 918. The eyelet frame 1106, shoulder portion 1112, and narrow portion 1110 of the localization element 930 are collectively referred to herein as an interlocking framework, which allows the localization element 930 to releasably interlock with the pusher element 920. The movement or translation of the localization element 930 can be controlled by the delivery control 904 when the interlocking framework is positioned within or interlocked with the delivery port 1118. In particular, the interlocking of the localization element 930 and the pusher element 920 by the interlocking framework allows longitudinal translation of the delivery control 904 to slide the localization element 930 in both a distal and proximal direction within the delivery needle 906, both pushing the localization element 930 out of the delivery needle 906 and retracting it into the delivery needle 906.

The localization element 930 can be deployed out of the delivery needle 906 when the pusher distal end 922 pushes the shoulder portion 1112 of the localization element 930 in the first longitudinal direction 1004 out of the delivery needle 906. The interlocking framework of the localization element 930 can release from the delivery port 1118 of the pusher element 920 when the delivery port 1118 exits the lumen of the delivery needle 906. The localization element 930 can curl into a substantially circular deployed configuration 942 when deployed. The localization element 930 can curl or curve in a direction of the handle dorsal side 912 when deployed out of the delivery needle 906.

The localization element 930 can comprise or be composed of a metal, a metal alloy, a polymer, or combinations thereof. In some variations, the localization element 930 can comprise or be composed of a shape-memory material. For example, the localization element 930 can comprise or be composed of a shape memory metal alloy such as Nitinol™. The localization element 930 can penetrate tissue and serve as a boundary or guidance marker for a tissue mass for subsequent removal and/or analysis.

The localization element 930 can be processed or finished so as to reduce the sliding friction between the localization element 930 and the inner surface of the needle lumen 918. For example, the localization element 930 can be electropolished or mechanically polished. The localization element 930 can also be covered by a blue-oxide finish. The localization element 930 can be covered by the blue-oxide finish by heat treating the localization element 930 in a salt bath.

The localization element 930 can be a flexible length of metal or wire, a flexible length of polymer, a flexible length of shape-memory material, or combinations thereof. The localization element 930 can take on an arcuate, curvilinear, or looping shape when deployed out of the delivery needle 906.

The pusher distal end 922 can be sloped and form an obtuse angle with the pusher ventral side 1116. The obtuse angle formed by the pusher distal end 922 and the pusher ventral side 1116 can be seen when viewed from a lateral side of the tissue localization device 900. The sloped design of the pusher distal end 922 can allow the pusher element 920 to more effectively push the shoulder portion 1112 of the localization element 930 in the first longitudinal direction 1004 without the shoulder portion 1112 curling upwards toward the top of the needle lumen 918. This can reduce sliding friction between the localization element 930 and the needle 918 as the localization element 930 is translated through the needle lumen 918. The pusher distal end 922 can also form an acute angle with the pusher dorsal side 1114 when viewed from the lateral side of the tissue localization device 900.

As previously discussed, the movement or translation of the localization element 930 can be controlled by the delivery control 904 when the eyelet frame 1106 is positioned within the delivery port 1118. The delivery port 1118 can have a distal port side 1120, a proximal port side 1122, and a port base 1124. The distal port side 1120 can form an acute angle with the port base 1124 when viewed from the lateral side of the tissue localization device 900.

The localization element 930 can be retracted back into the delivery needle 906 even after at least a portion of the localization element 930, such as the locator distal end 1102, has exited the needle lumen 918. The localization element 930 can be retracted back into the delivery needle 906 when the distal port side 1120 of the pusher element 920 pulls on an eyelet shoulder 1113 in the second longitudinal direction 1006. The pusher element 920 can be pulled in the second longitudinal direction 1006, for example, when a user applies a force to the second interface surface 1002 of the delivery control 904 in the second longitudinal direction 1006.

The pusher element 920 can have a pusher lumen 1126. The narrow portion 1110 of the localization element 930 can be positioned within a segment of the pusher lumen 1126 when the eyelet frame 1106 is positioned within the delivery port 1118.

FIGS. 11A and 11B also illustrate that the tracking wire 932 can be coupled to the locator proximal end 1100 of the localization element 930. The tracking wire 932 can be coupled or tied to the eyelet frame 1106 of the localization element 930. The wire distal end 936 of the tracking wire 932 can be threaded through the aperture 1108 such that a loop 1128 forms around the eyelet frame 1106. The wire distal end 936 can then be secured to another segment of the tracking wire 932 at an attachment site 1130. For example, the wire distal end 936 can be secured to an attachment site 1130 along the wire distal segment 934. More specifically, the wire distal end 936 can be welded or adhered with adhesive to another segment of the tracking wire 932 at a site serving as the attachment site 1130. In other variations, the wire distal end 936 can be tied to another segment of the tracking wire 932 or crimped to another segment of the tracking wire 932 using a ferrule.

The tracking wire 932 can comprise or be composed of a metal or metal alloy such as stainless steel. The tracking wire 932 can comprise or be composed of a cable for flexibility, tensile strength, and low-profile. For example, the cable can be a 19-filament metal wire cable. In other variations, the tracking wire 932 can comprise or be composed of a braided cable such as a high-tensile strength braided suture used in such applications as orthopedic surgery.

A polymer jacketing 1132 can cover or ensheath at least part of the tracking wire 932. The polymer jacketing 1132 can also cover or ensheath the attachment site 1130. The polymer jacketing 1132 can be a heat-shrink polymer or tube wrapped around the tracking wire 932. At least part of the tracking wire 932 can be positioned within the pusher lumen 1126, the needle lumen 918, and the handle lumen 1008 when the localization element 930 is detachably held by or detachably interlocks with the pusher element 920. By jacketing the side-by-side portions of the tracking wire 932, the tracking wire 932 behaves as one filament, making it easier for the clinician to handle the tracking wire 932 for example during coiling or subsequently during surgical specimen removal.

Once the localization element 930 has detached from the pusher element 920, the tracking wire 932 can exit the pusher lumen 1126 and the needle lumen 918 as the delivery needle 906 is retracted away from the deployed localization element 930. For example, the localization element 930 can be deployed out of the delivery needle 906 within the tissue of a patient. In this example, an operator of the tissue localization device 900 can slowly retract the delivery needle 906 out of the tissue of the patient. As the delivery needle 906 is retracted out of the patient, more of the tracking wire 932 can be exposed. As will discussed in the following sections, at least a segment of the tracking wire 932 can remain within the tissue of the patient after the delivery needle 906 is removed from the patient.

Figure 11C:
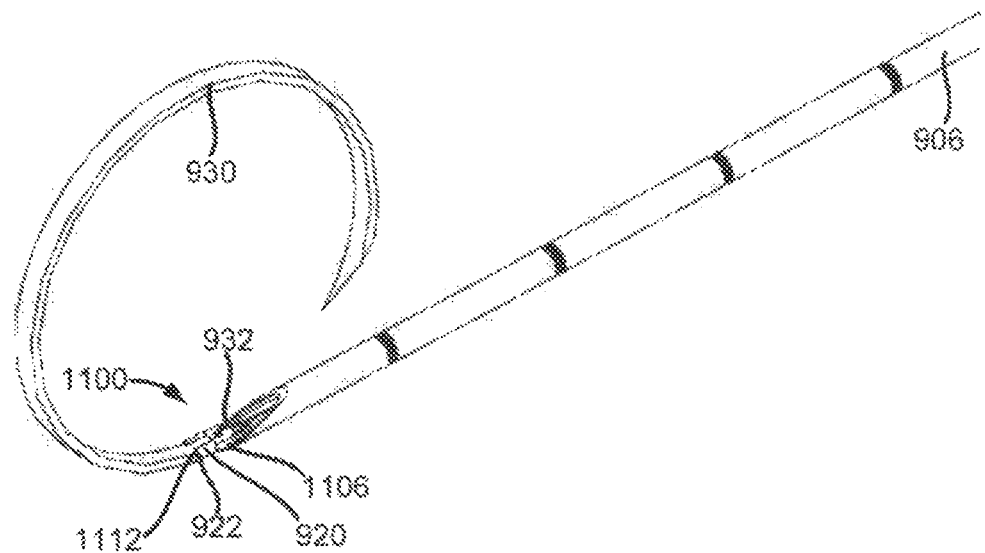
FIGS. 11C and 11D illustrate top and bottom perspective views, respectively, of a localization element detachably held by a pusher element.
Figure 11D:
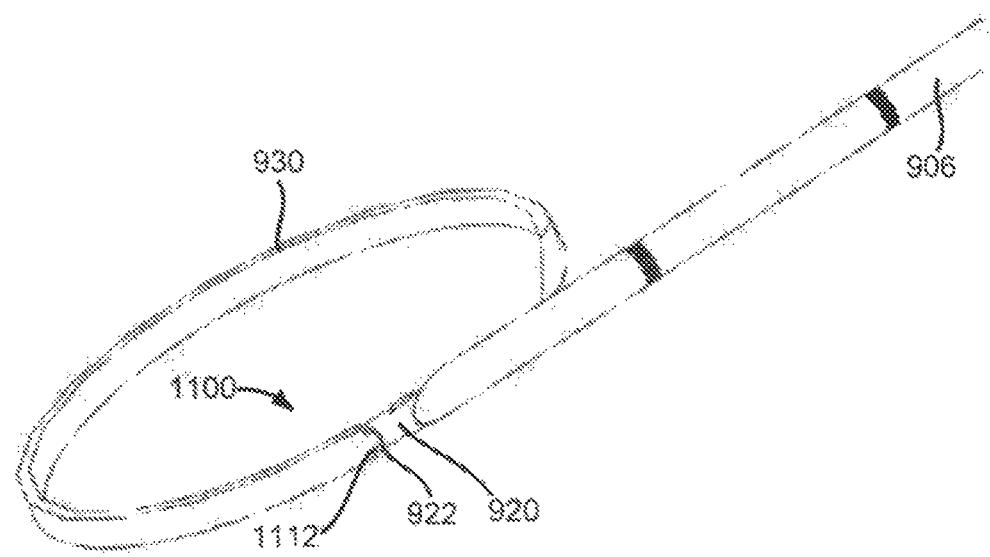

FIGS. 11C and 11D illustrate that the movement or translation of the localization element 930 can be controlled by the delivery control 904 when the eyelet frame 1106 is positioned within the delivery port 1118. The localization element 930 can automatically detach or be dislodged from the pusher element 920 and the delivery needle 906 when at least part of the eyelet frame 1106 held by the delivery port 1118 is translated by the delivery control 904 out of the delivery needle 906. For example, the localization element 930 can automatically separate, detach, or dislodge from the pusher element 920 when the eyelet frame 1106 is pushed out of the needle lumen 918 and the localization element 930 no longer constrained by the interior surface of the needle lumen 918. The localization element 930 can be considered detached from the pusher element 920 when the eyelet frame 1106 is no longer positioned within the delivery port 1118. The rotational orientation of the pusher element 920 as shown in FIG. 11D can improve automatic detachment of the localization element 930 from the pusher element 920. This orientation facilitates the localization element 930 to move freely away from the pusher element 920 due to the inherent direction of motion imparted by the shape memory of the localization element. This orientation allows for automatic separation from the interlocking connection between the pusher element 920 and localization element 930 once the interlocking framework of the localization element 930 is no longer constrained by the bore of the delivery needle 906.

The localization element 930 can be retracted back into the delivery needle 906 when at least a portion of the eyelet frame 1106 is still positioned within the delivery port 1118.

Figure 11E:
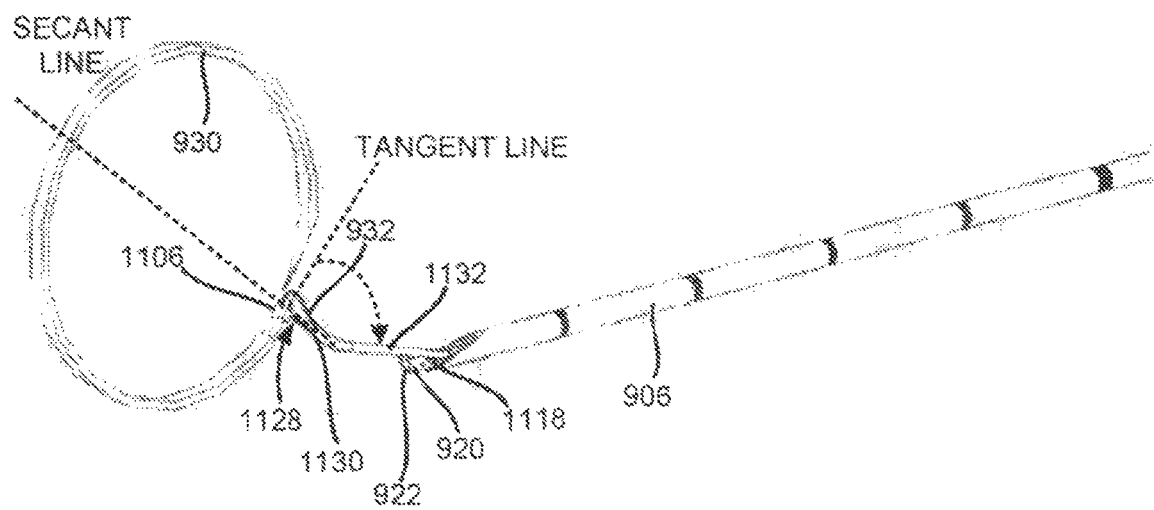
FIGS. 11E and 11F illustrate top and bottom perspective views, respectively, of a tracking wire rotated relative to a localization element when the localization element is detached from a pusher element.
Figure 11F:
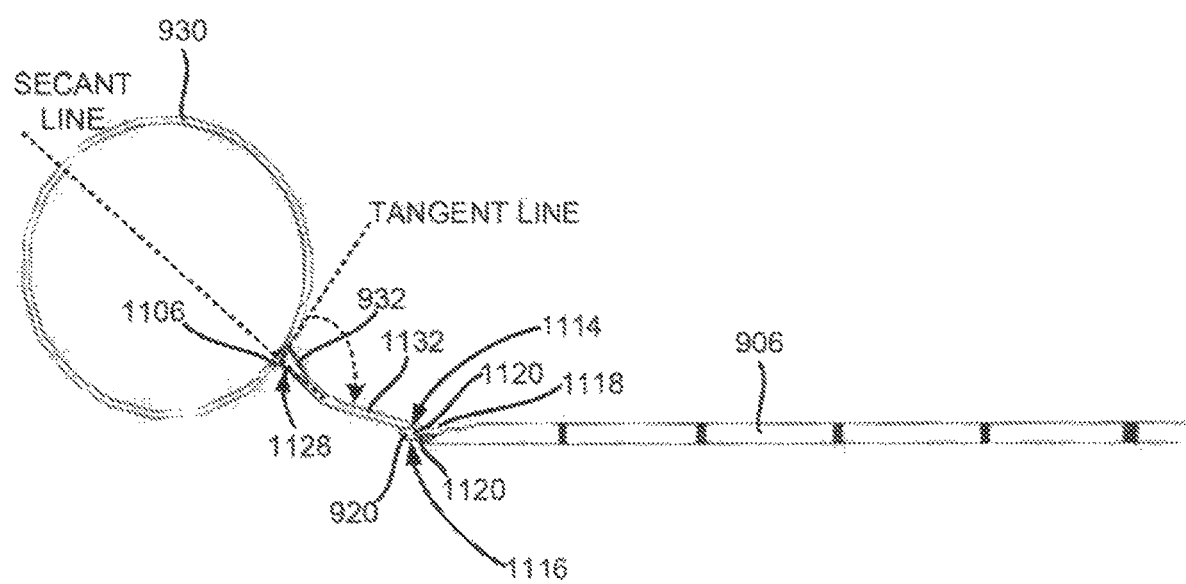

FIGS. 11E and 11F illustrate that the tracking wire 932 coupled to the locator proximal end 1100 can swivel or rotate relative to the localization element 930 when the localization element 930 is detached from the rest of the tissue localization device 900. For example, the loop 1128 formed by the wire distal segment 934 can swivel or rotate relative to the eyelet frame 1106.

FIGS. 11E and 11F illustrate that the spatial alignment of the tracking wire 932 can initially be positioned essentially tangential to a curvature of the deployed localization element 930. For example, the localization element 930 can curl into a circular shape when in the deployed configuration 942 and the tracking wire 932 can initially be aligned tangent to the circular-shaped localization element 930. FIGS. 11E and 11F also illustrate that the loop 1128 formed by the tracking wire 932 can subsequently swivel or rotate with respect to the eyelet frame 1106 typically due to movement of the proximal end of the localization element 930 as it becomes unconstrained by the needle lumen 918. Once the loop 1128 swivels or rotates, the spatial alignment of the tracking wire 932 relative to the localization element 930 can change. For example, at least a segment of the tracking wire 932 can be aligned as a secant or in a non-tangential orientation relative to the circular-shaped localization element 930 once the loop 1128 formed by the wire distal segment 934 swivels or rotates.

The tracking wire 932 can automatically change its spatial alignment relative to the localization element 930 once the localization element 930 is detached from the rest of the delivery system of the tissue localization device 900. For example, when the tracking wire 932 is aligned tangential to the curled localization element 930, the localization element 930 can be more susceptible to inadvertent displacement within the tissue of the patient when the tracking wire 932 is pulled or when the patient moves. Changing the spatial alignment of the tracking wire 932 relative to the localization element 930 can make the deployed localization element 930 more difficult to displace within the tissue of the patient by pulling on the tracking wire 932 or when the patient moves. In addition, changing the alignment of the tracking wire 932 relative to the localization element 930 from a tangential alignment to a secant or non-tangential alignment can reduce the risk that the localization element 930 inadvertently retracts out of the tissue of the patient when the tracking wire 932 is being pulled by the patient or a health professional or when a patient moves.

Figure 12:
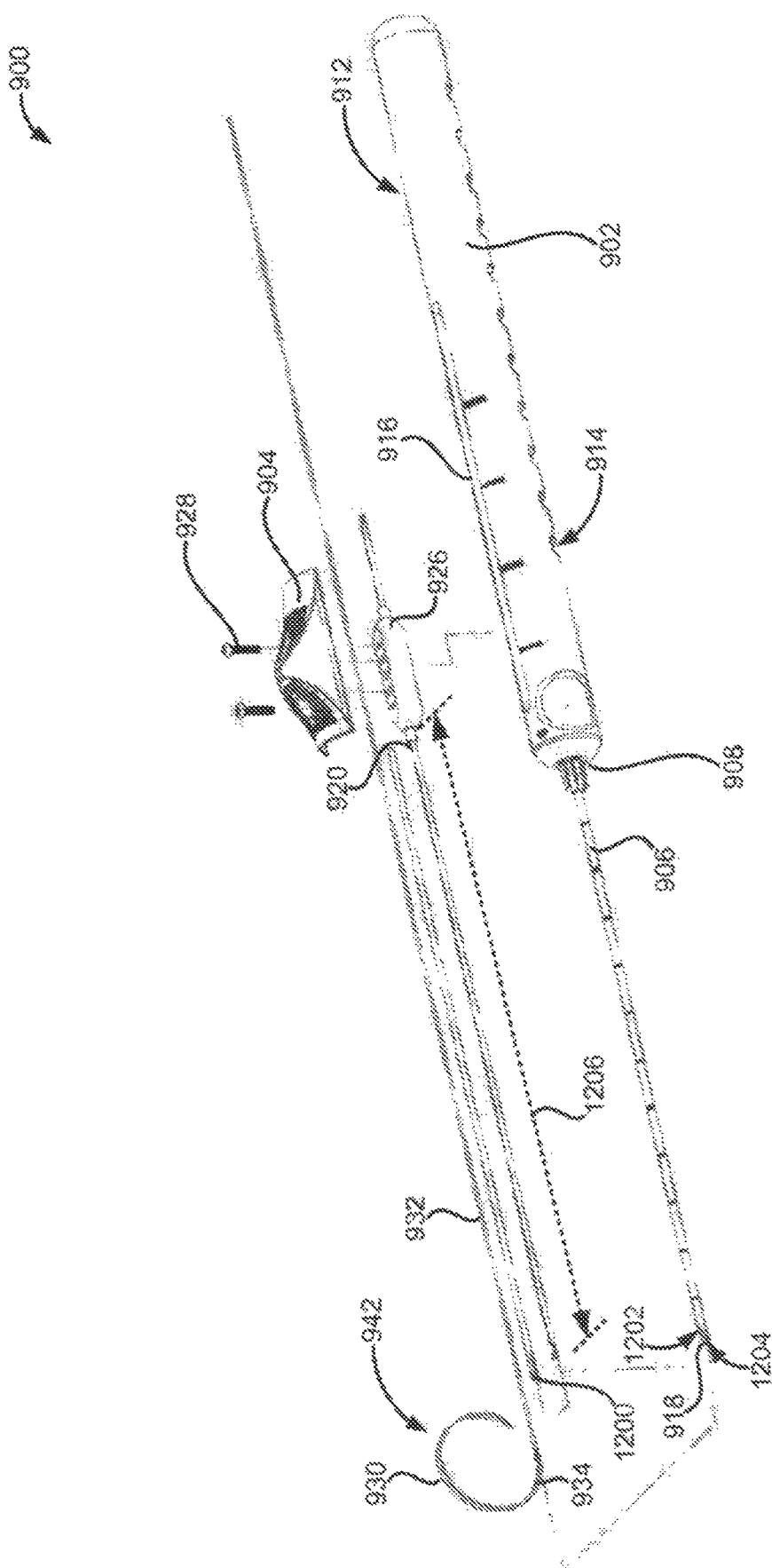
FIG. 12 illustrates an exploded view of another variation of the tissue localization device.

FIG. 12 illustrates that the tissue localization device 900 can include a polymer liner 1200. The polymer liner 1200 can radially ensheath or surround at least a portion of the pusher element 920, and can be slidably translatable in the delivery needle 906. The polymer liner 1200 can prevent metal-on-metal contact between the outer surface of the pusher element 920 and at least a portion of the localization element 930 as well as the surface of the needle lumen 918 as the pusher element 920 is translated through the needle lumen 918. The liner 1200 can also move along with the pusher element 920 as the pusher element travels through the delivery needle lumen thereby preventing metal from sliding against metal for the portion of the localization element 930 that is ensheathed by the liner 1200. The polymer liner 1200 can be interposed or pressed between an outer surface of the pusher element 920 and the surface of the needle lumen 918 or a portion of the localization element 930 or tracking wire 932 and the surface of the needle lumen 918 in order to reduce the static and/or dynamic frictional forces acted upon by the pusher element 920, the localization element 930 or tracking wire 932 as the pusher element 920 travels through the needle lumen 918.

The needle lumen 918 can have a lumen dorsal surface 1202 and a lumen ventral surface 1204. The lumen dorsal surface 1202 can refer to an upper portion or top half of the needle lumen 918. The lumen ventral surface 1204 can refer to a lower portion or bottom half of the needle lumen 918. The polymer liner 1200 can completely encircle or surround the pusher element 920 such that no contact is made between the external surface of the pusher element 920 and the needle lumen 918 as the pusher element 920 is translated longitudinally through the needle lumen 918. In another variation, the polymer liner 1200 can cover the pusher dorsal side 1114 and prevent the pusher dorsal side 1114 from contacting the lumen dorsal surface 1202 as the pusher element 920 is translated longitudinally through the needle lumen 918. The polymer liner 1200 can cover the pusher ventral side 1116 and prevent the pusher ventral side 1116 from contacting the lumen ventral surface 1204 as the pusher element 920 is translated longitudinally through the needle lumen 918.

The polymer liner 1200 can comprise or be fabricated from polyether ether ketone (PEEK). In other variations, the polymer liner 1200 can comprise or be fabricated from any polymer or polymer blend (e.g., a fluoropolymer) capable of facilitating the longitudinal translation of the pusher element 920 through the needle lumen 918.

The polymer liner 1200 can have a liner length 1206 substantially equivalent to the needle length 1012. In other variations, the needle length 1012 can be greater than the liner length 1206.

Figure 13A:
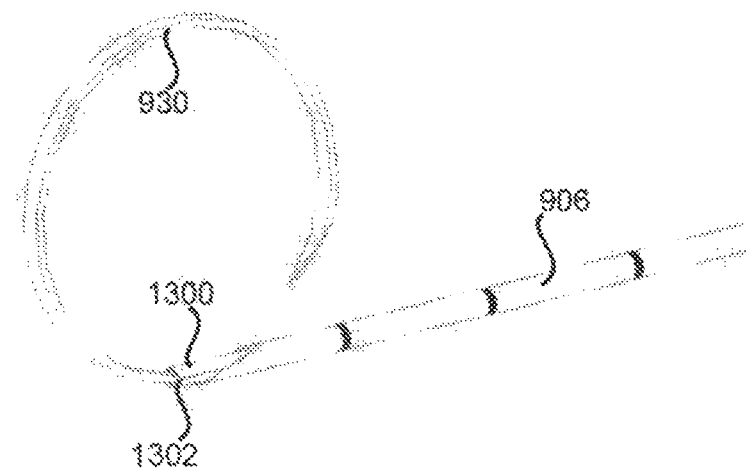
FIG. 13A illustrates a perspective view of a localization element deployed out of a delivery needle by a pusher element covered by a polymer liner.
Figure 13B:
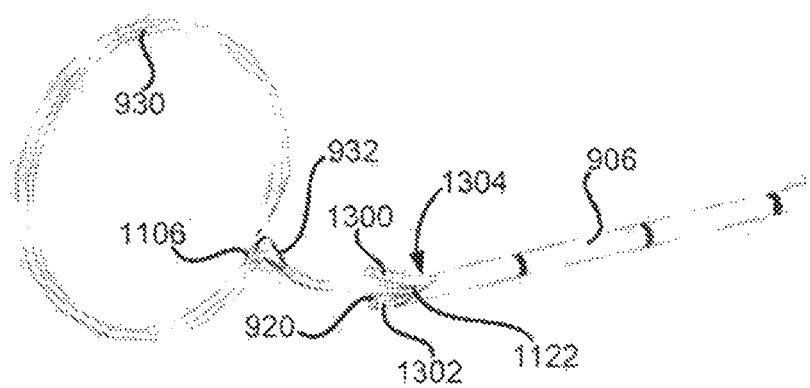
FIGS. 13B and 13C illustrate perspective and side views, respectively, of a localization element detached from a pusher element partially separated from a polymer liner.
Figure 13C:
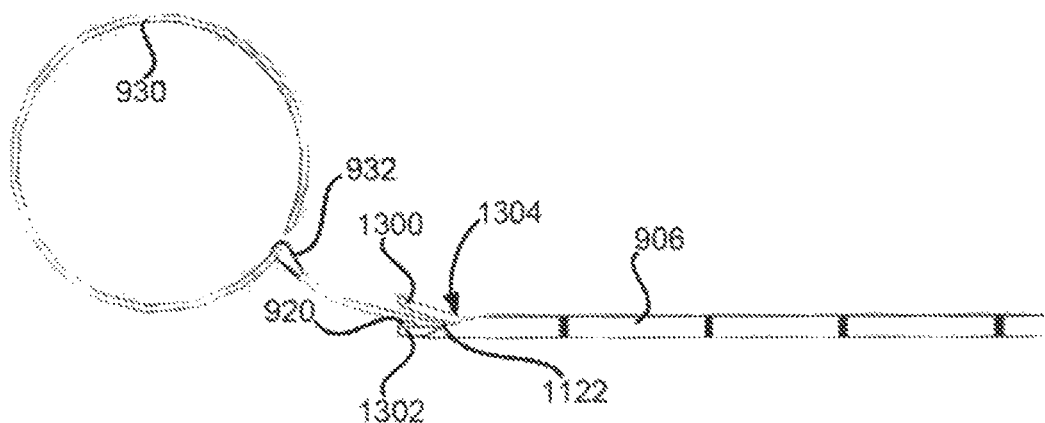

FIGS. 13A to 13C illustrate that the polymer liner 1200 can include a dorsal liner 1300 and a ventral liner 1302. The dorsal liner 1300 and the ventral liner 1302 can combine to radially ensheath or surround the pusher element 920. The polymer liner 1200 can have a liner distal segment 1304. The liner distal segment 1304 can extend from the pusher distal end 922 to the proximal port side 1122.

FIG. 13B illustrates that the dorsal liner 1300 can separate from the ventral liner 1302 when the liner distal segment 1304 is pushed or deployed out of the needle lumen 918. The dorsal liner 1300 can separate from the ventral liner 1302 by curling away from the ventral liner 1302. The dorsal liner 1300 can separate from the ventral liner 1302 when the localization element 930 detaches from the pusher element 920. For example, because of the force acted upon the liner by the shape memory of the localization element, the eyelet frame 1106 can separate the dorsal liner 1300 from the ventral liner 1302 at the liner distal segment 1304 as the eyelet frame 1106 detaches or is physically displaced from the delivery port 1118.

The dorsal liner 1300 can act as an additional safeguard against the inadvertent detachment of the localization element 930 from the pusher element 920 when the localization element 930 is being translated through the needle lumen 918. For example, the dorsal liner 1300 along with the port base 1124 of the pusher element 920 can act as an additional layer of material to hold the eyelet frame 1106 within the delivery port 1118 when the localization element 930 is within the needle lumen 918 or in motion through the needle lumen 918.

The polymer liner 1200 including the dorsal liner 1300 and the ventral liner 1302 can be, attached, in part, to the pusher element 920. For example, the polymer liner 1200 can be attached to the pusher element 920 by UV cured adhesives. The polymer liner 1200 can be mechanically fitted to the pusher element 920 by methods such as crimping within the pusher plug 926.

The dorsal liner 1300 can once again join with the ventral liner 1302 to radially ensheath or surround the pusher element 920 when the pusher element 920 is translated in the second longitudinal direction 1006 back into the needle lumen 918. For example, the dorsal liner 1300 can once again join with the ventral liner 1302 when the localization element 930, along with the pusher element 920, is retracted back into the needle lumen 918. Also, for example, the dorsal liner 1300 can again join with the ventral liner 1302 when the localization element 930 is completely deployed out of the delivery needle 906 and the empty pusher element 920 is retracted back into the needle lumen 918.

Figure 14A:
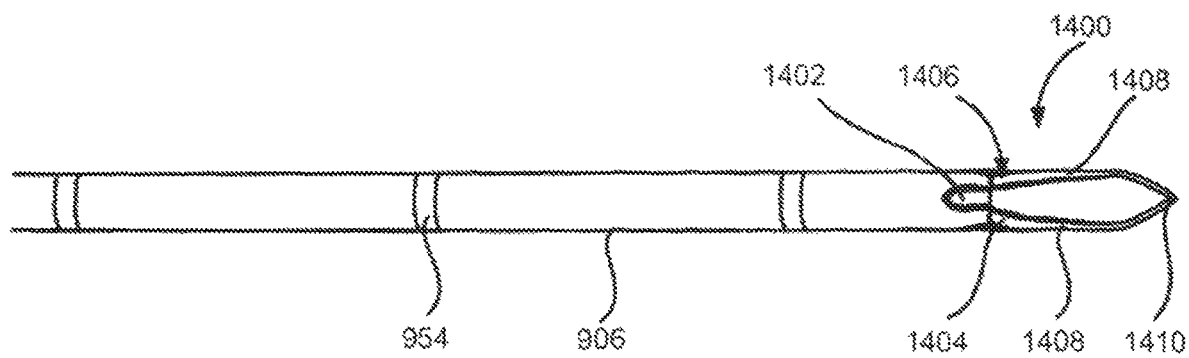
FIGS. 14A and 14B illustrate a variation of a delivery needle having a needle dimple.
Figure 14B:
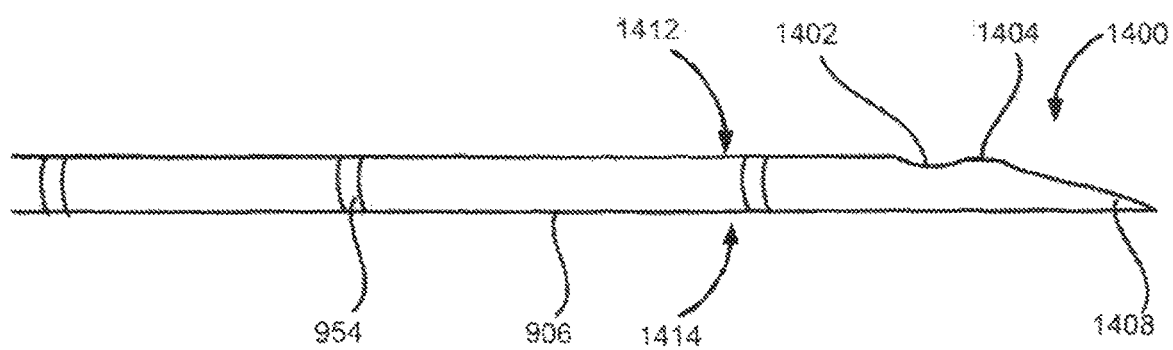

FIGS. 14A and 14B illustrate that the delivery needle 906 can have a beveled distal end 1400 and a needle dimple 1402. The beveled distal end 1400 can be defined by a rounded edge 1404 along a proximal rim 1406 of the beveled distal end 1400 and two lateral sharpened edges 1408 converging into a needle tip 1410.

The rounded edge 1404 can be positioned proximal to the two lateral sharpened edges 1408 and the needle tip 1410. The two lateral sharpened edges 1408 and the needle tip 1410 can be configured to pierce through the dermis and into the underlying tissue of the patient. The proximal rim 1406 of the beveled distal end 1400 can be the portion of the beveled distal end 1400 not included as part of the two lateral sharpened edges 1408 and the needle tip 1401. The rounded edge 1404 can be a surface feature of the proximal rim 1406 formed by smoothing or rounding out the edges of the proximal rim 1406. The rounded edge 1404 can have a radius. The rounded edge 1404 can reduce the mechanical trauma to the localization element 930 caused by an otherwise sharp-edged beveled distal end 1400.

The delivery needle 906 can have a needle dorsal side 1412 and a needle ventral side 1414 opposite the needle dorsal side 1412. The needle dimple 1402 can be a concavity, divot, or flattened region along the needle dorsal side 1412. The needle dimple 1402 can be shaped as a half-ellipsoid. In other variations, the needle dimple 1402 can be oval or oblong-shaped. The needle dimple 1402 can be proximal to the rounded edge 1404 of the beveled distal end 1400.

Figure 14C:
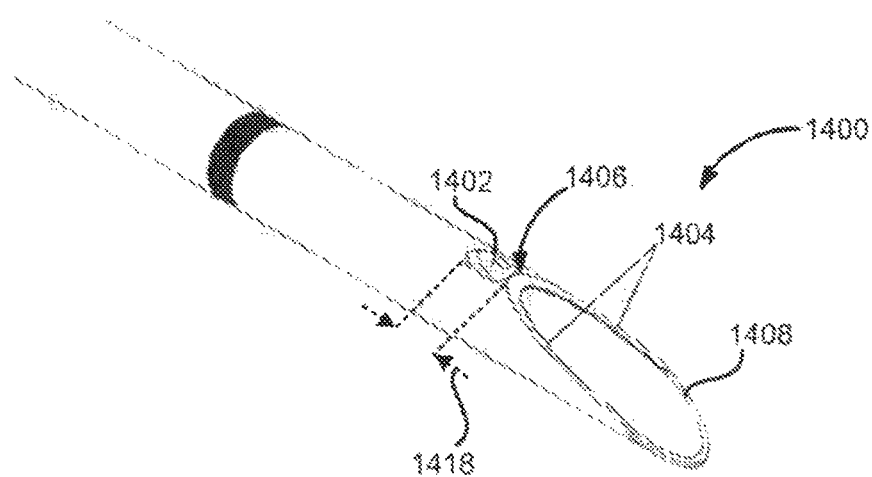
FIG. 14C illustrates a close-up of a beveled distal end of a variation of a delivery needle.

FIG. 14C illustrates that the needle dimple 1402 can have a dimple length 1418. For example, the dimple length 1418 can be between approximately 0.5 mm and 1.5 mm.

Figure 14D:
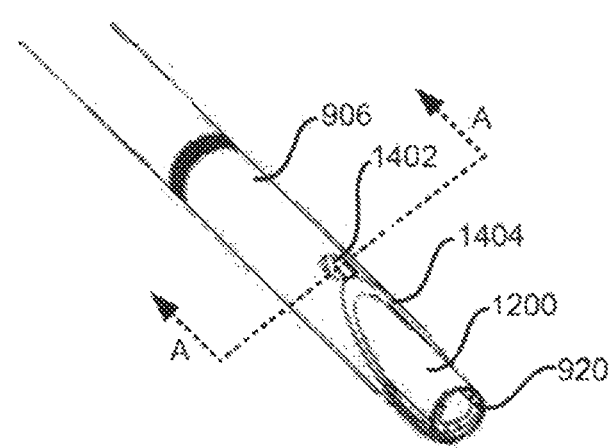
FIG. 14D illustrates a close-up of a variation of a pusher element covered by a polymer liner extending out of the beveled distal end.

FIG. 14D illustrates that the pusher element 920 covered by the polymer liner 1200 can translate longitudinally out of the beveled distal end 1400 having the needle dimple 1402.

The pusher element 920 can be an elongate half-cylinder having a hollow interior. The needle dimple 1402 can allow the pusher element 920 to more easily exit the beveled distal end 1400 of the delivery needle 906.

Figure 14E:
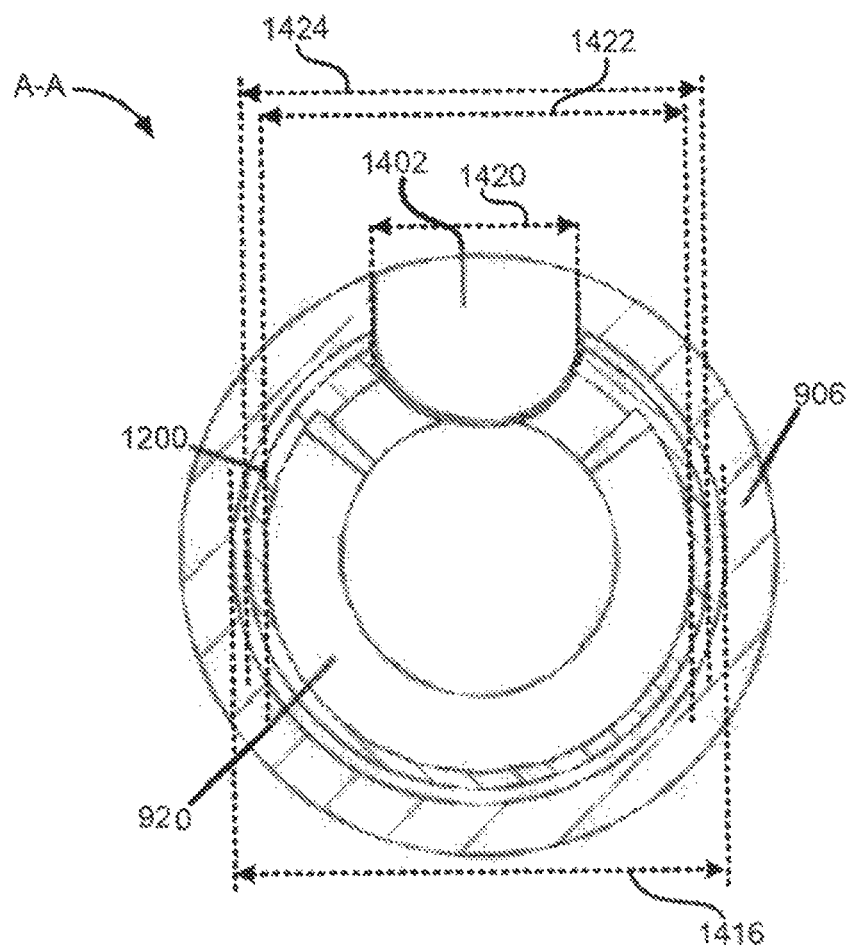
FIG. 14E illustrates a cross-section of the delivery needle enclosing the pusher element covered by the polymer liner along line A-A shown in FIG. 14D.

FIG. 14E illustrates that the needle lumen 918 can have a lumen diameter 1416. For example, the lumen diameter 1416 can be between approximately 0.8 mm and 1.3 mm. FIG. 14E also illustrates that the needle dimple 1402 can have a dimple width 1420. The dimple width 1420 can be between approximately 0.5 mm and 1.1 mm. The dimple width 1420 can be less than the lumen diameter 1416 such that the pusher element 920 can translate past the section of the delivery needle 906 defined by the needle dimple 1402 without being obstructed by the needle dimple 1402.

When the dimple width 1420 is less than the lumen diameter 1416, the lateral sides of the pusher element 920 can be unobstructed by the needle dimple 1402 as the pusher element 902 moves through the needle lumen 918. The needle dimple 1402 can allow the localization element 930 to more easily exit the beveled distal end 1400 of the delivery needle 906. For example, the needle dimple 1402 can reduce the likelihood of the eyelet frame 1106 from being inadvertently detached from the delivery port 1118 when the localization element 930 is being deployed out of the delivery needle 906.

For example, the indentation of the needle dimple 1402 on the needle lumen 918 of the delivery needle 906 causes the localization element 930 to be pushed away from the beveled distal end 1400 of the delivery needle 906 as it is retracted or advanced. This reduces the friction and/or abrasion of the localization element 930 against the beveled distal end 1400 of the delivery needle 906.

The needle dimple 1402 can allow the localization element 930 to be retracted into or deployed out of the beveled distal end 1400 of the delivery needle 906 when at least part of the localization element 930 has been deployed out of the delivery needle 906. As another example, the needle dimple 1402 can ensure the delivery port 1118 holds the eyelet frame 1106 by pushing the eyelet frame 1106 further into the delivery port 1118 when the pusher element 920 is being retracted into the needle lumen 918.

FIG. 14E also illustrates that the polymer liner 1200 can have a liner inner diameter 1422 and a liner outer diameter 1424. The liner inner diameter 1422 can be between approximately 0.90 mm and 1.10 mm. For example, the liner inner diameter 1422 can be approximately 1.10 mm. The liner outer diameter 1424 can be between approximately 1.00 mm and 1.20 mm. For example, the liner outer diameter 1424 can be approximately 1.14 mm.

Figure 15A:
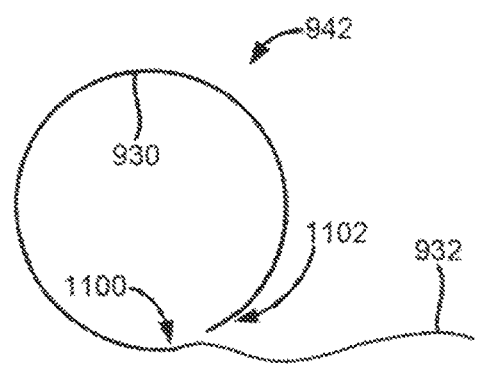
FIG. 15A illustrates a tracking wire coupled to an end of a variation of a localization element.

FIG. 15A illustrates that the tracking wire 932 can be coupled to the localization element 930 at the locator proximal end 1100. For example, the tracking wire 932 can be looped around the eyelet frame 1106 of the localization element 930. As shown in FIG. 15A, the localization element 930 can have a substantially circular deployed configuration 942. The deployed configuration 942 can be a predetermined shape or configuration of the localization element 930. For example, the deployed configuration 942 can be a shape memory configuration obtained by heat setting the localization element 930 during its manufacturing process. The localization element 930 can automatically transform into its deployed configuration 942 when deployed or detached from the rest of the tissue localization device 900.

Figure 15B:
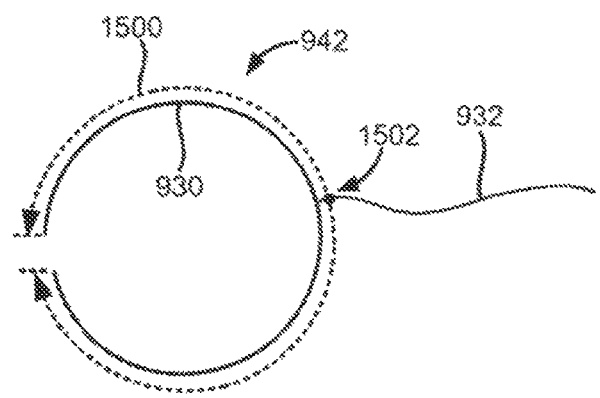
FIG. 15B illustrates a tracking wire coupled to a midpoint along a length of a variation of a localization element.

FIG. 15B illustrates that the localization element 930 can have a locator length 1500. For example, when the localization element 930 is formed into a substantially circular deployed configuration 942, the locator length 1500 can be a perimeter length. FIG. 15B illustrates that the tracking wire 932 can be coupled to the localization element 930 at a midpoint 1502 along the locator length 1500. For example, the localization element 930 can have an aperture or notch defined at the midpoint 1502 and the tracking wire 932 can be looped through the aperture or notch and tied to the localization element 930 at the midpoint 1502.

The tracking wire 932 can be coupled to the localization element 930 at a point in between the midpoint 1502 and the locator proximal end 1100 or in between the midpoint 1502 and the locator distal end 1102. The tracking wire 932 can be coupled to the midpoint 1502 or another point along the length of the localization element 930 other than the locator proximal end 1100 to prevent the tracking wire 932 from inadvertently displacing or retracting the localization element 930 when the localization element 930 is deployed within the tissue of a patient. For example, the tracking wire 932 can inadvertently displace or retract the localization element 930 when a user pulls on the tracking wire 932 or the patient moves after the localization element 930 is deployed within the tissue of the patient.

Figure 15C:
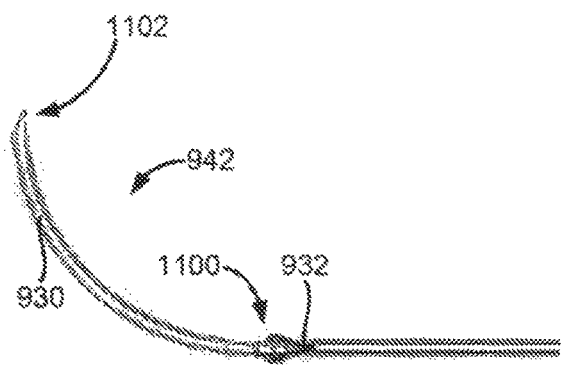
FIG. 15C illustrates a side view of a tracking wire coupled to an end of a variation of a localization element.
Figure 15D:
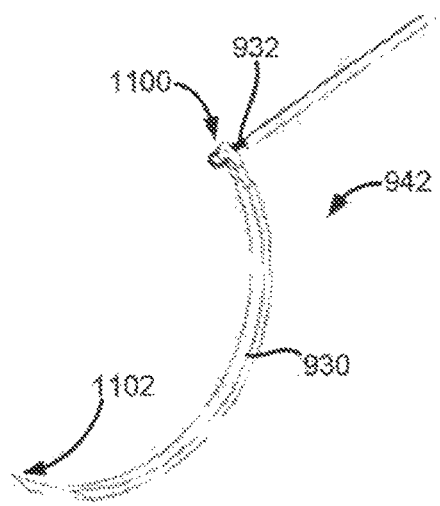
FIG. 15D illustrates a perspective view of a tracking wire coupled to an end of a variation of a localization element.

FIGS. 15C and 15D illustrate that the localization element 930 having a sickle or falciform-shaped deployed configuration 942. The sickle or falciform shape can be a partial circular shape or crescent shape. As shown in FIG. 15C, the tracking wire 932 can be coupled to the sickle or falciform-shaped localization element 930 at the locator proximal end 1100.

Figure 15E:
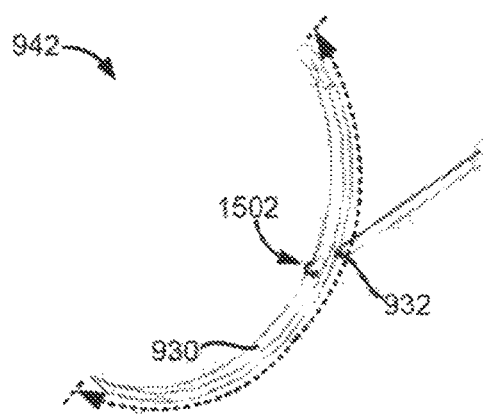
FIG. 15E illustrates a tracking wire coupled to a midpoint along a length of a variation of a localization element.

FIG. 15E illustrates that the tracking wire 932 can be coupled to the localization element 930 having the sickle or falciform-shaped deployed configuration 942 at a midpoint 1502 along the curved locator length 1500 of the localization element 930. The different deployed shapes of the localization element 930 can allow the tissue localization device 900 to localize or demarcate tissue masses of different sizes and shapes.

Figure 15F:
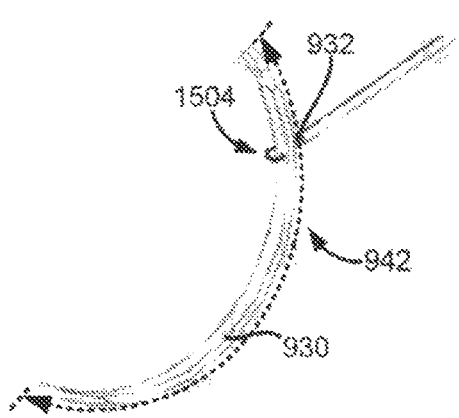
FIG. 15F illustrates a tracking wire coupled to a point in between a midpoint and an end of a variation of a localization element.

FIG. 15F illustrates that the tracking wire 932 can be coupled to the localization element 930 at an attachment point 1504 along the locator length 1500 in between the midpoint 1502 and the locator proximal end 1100. For example, the attachment point 1504 can be located at a point one-quarter the locator length 1500. The localization element 930 can have an aperture or notch defined at the attachment point 1504 and the tracking wire 932 can be looped through the aperture or notch and tied to the localization element 930 at the attachment point 1504.

Figure 16:
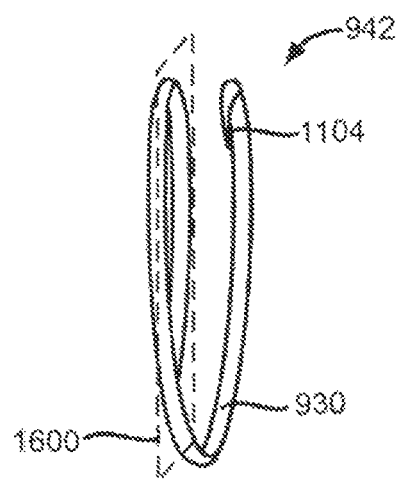
FIG. 16 illustrates a variation of a localization element in a partial helical configuration.

FIG. 16 illustrates that the localization element 930 can have a curvature plane 1600 when in the deployed configuration 942. The curvature plane 1600 can be a two dimensional plane used to orient the localization element 930. For example, in the variations of the localization element 930 shown in FIGS. 11A to 11F, the entire localization element 930 can be curved substantially in alignment with the curvature plane 1600. FIG. 16 illustrates that at least part of the localization element 930 can be curved in alignment with the curvature plane 1600 and another part of the localization element 930 can be curved or otherwise oriented out of the curvature plane 1600.

For example, the locator proximal end 1100 can be curved in alignment with the curvature plane 1600 and the locator distal end 1102 can be curved out of the curvature plane 1600. As shown in FIG. 16, the localization element 930 can have a full or partial helical shape when in the deployed configuration 942. A part of the localization element 930 can curve out of the curvature plane 1600 to localize or demarcate a suspect tissue mass in the patient's body in three-dimensions.

Figure 17:
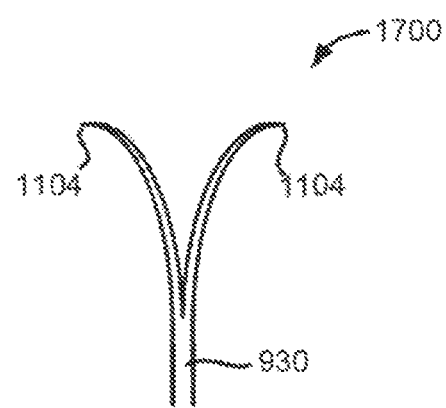
FIG. 17 illustrates a locator distal end of a variation of a localization element with branched locator tips.

FIG. 17 illustrates that the localization element 930 can have a branched distal segment 1700. As shown in FIG. 17, the branched distal segment 1700 can be an instance of the locator distal end 1102 having two or more sharpened locator tips 1104. For example, when the branched distal segment 1700 has two sharpened locator tips 1104, the two sharpened locator tips 1104 can diverge at an angle away from one another. The branched distal segment 1700 of the localization element 930 can allow the localization element 930 to more securely anchor into the tissue of the patient, and also can more fully delineate the tissue site in three dimensions.

Figure 18A:
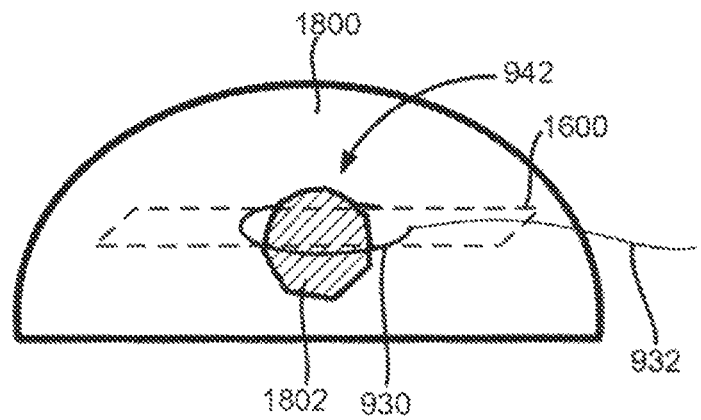
FIG. 18A illustrates a deployment of a localization element around a suspect tissue mass.

FIG. 18A illustrates that the localization element 930 deployed into the tissue 1800 of a patient can encircle or radially surround at least part of a suspect tissue mass 1802. For example, the tissue 1800 can include breast tissue or lung tissue. The suspect tissue mass 1802 can include a tumor or other cancerous cells, necrotic tissue, lymph nodes, scar-tissue, target tissue, fibro adenoma, calcifications, otherwise diseased tissue, or combinations thereof.

FIG. 18A illustrates that the localization element 930 in the deployed configuration 942 can be curved or curled in alignment with a curvature plane 1600. The localization element 930 can encircle or radially surround at least part of the suspect tissue mass 1802 when the curvature plane 1600 intersects at least part of the suspect tissue mass 1802. The deployed localization element 930 can serve as a boundary or guide for identifying and demarcating the location or boundary (e.g. the posterior margin) of the suspect tissue mass 1802 for further analysis or excision.

FIGS. 18B-18E illustrate that the localization element 930 can be deployed adjacent to or abutting the suspect tissue mass 1802. For example, the localization element 930 can be deployed above or proximal to the suspect tissue mass 1802 such that the localization element 930 forms a type of halo adjacent the suspect tissue mass 1802. This deployment can be referred to as a halo deployment. The localization element 930 can be deployed at one or more locations adjacent to or abutting the suspect tissue mass 1802 such that the curvature plane 1600 formed by the localization element 930 does not intersect at least a portion of the suspect tissue mass 1802. By deploying the localization element 930 above or away from the suspect tissue mass 1802, the user can ensure that the localization element 930 does not puncture, pierce, or otherwise disturb the suspect tissue mass 1802 or other tissue structures nearby (e.g., nerves, blood vessels, etc.).

Figure 18B:
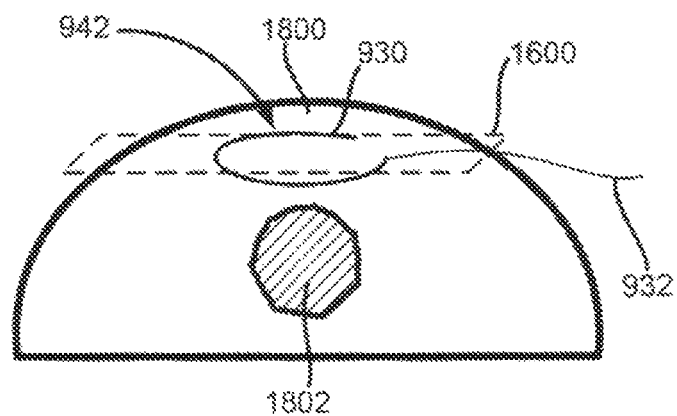
FIG. 18B illustrates a halo deployment of a localization element above a suspect tissue mass.
Figure 18C:
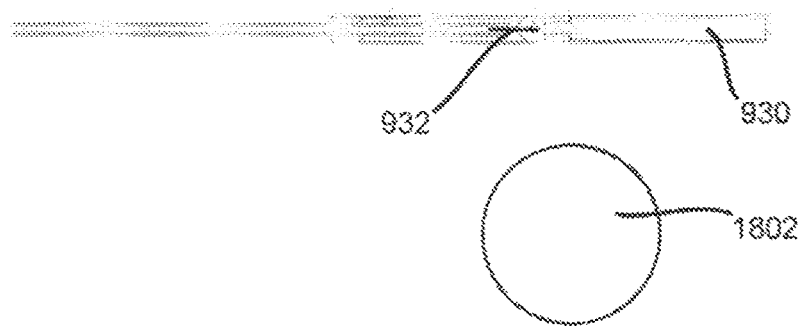
FIG. 18C illustrates a side view of a halo deployment of a localization element above a suspect tissue mass.
Figure 18D:
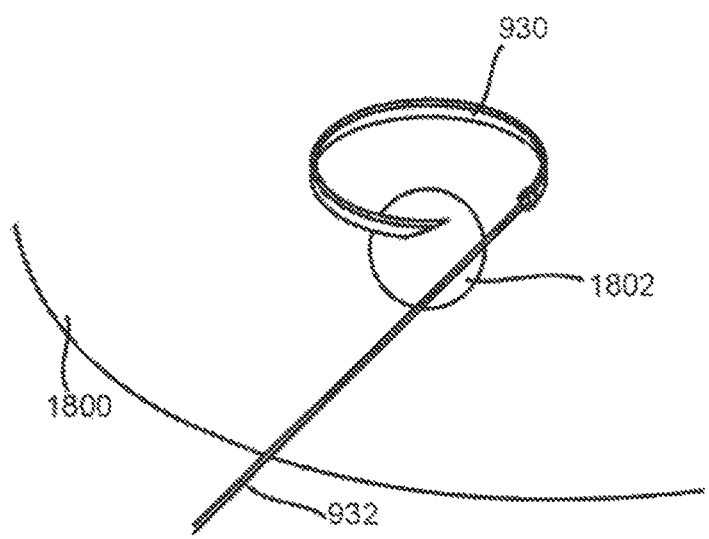
FIG. 18D illustrates a perspective view of the halo deployment of the localization element above a suspect tissue mass.
Figure 18E:
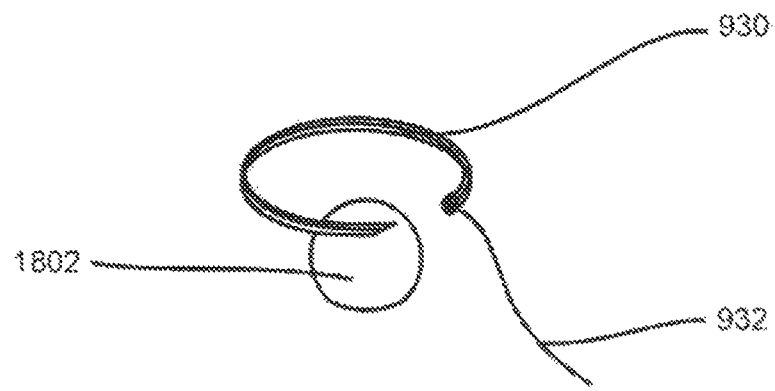
FIG. 18E is another perspective view of a halo deployment of a localization element above a suspect tissue mass.

FIGS. 18A, 18B, and 18D illustrate that at least a segment of the tracking wire 932 can extend out of the tissue 1800 of the patient while the wire distal end 936 coupled to the localization element 930 is deployed within the tissue 1800 of the patient. The tracking wire 932 can serve as a path or trail informing a surgeon of the path taken by the delivery needle 906 into the patient's tissue 1800. The tracking wire 932 may also serve as an intraoperative guide to the location of the localization element 930.

A method of locating the suspect tissue mass 1802 using the deployed localization element 930 and the tracking wire 932 can involve periodically pulling on the segment of the tracking wire 932 extending outside of the tissue 1800 of the patient. For example, a surgeon responsible for excising a suspect tissue mass 1802 can pull or tug on the segment of the tracking wire extending outside the tissue 1800 of the patient. The method can further involve palpating or feeling, with at least one finger of a user, an outer tissue layer (e.g., a skin or dermis) above or proximal to a target tissue site while pulling on the segment of the tracking wire 932 extending outside the tissue 1800 of the patient. The method can also involve locating the suspect tissue mass 1802 within the tissue 1800 of the patient based on a tension exhibited by the tracking wire 932 being pulled and the movement felt by the finger of the user on the outside tissue layer.

If electrocautery is used during surgical dissection, several attributes of the localization element 930 can reduce the risk of damage to the localization element 930 and tracking wire 932 from inadvertent arcing of electrocautery during surgical dissection. Inadvertent passage of current to the tracking wire 932 can be reduced because the polymer jacketing 1132 of the tracking wire serves as an electrical insulator. Also, because of the ribbon-like and hence relatively large surface area the localization element 930, it may be less prone to inadvertent electrocautery damage than a localization wire with a smaller surface area, as the larger surface area is inherently more electrically dissipative.

FIGS. 19A-19C illustrate that the tracking wire 932 can be flexible enough to be easily wound into a coiled segment 1900. The tracking wire 932 is extremely flexible, having a flexibility comparable to surgical suture or household sewing thread. For example, the segment of the tracking wire 932 extending outside the tissue 1800 of the patient (see FIG. 19B) can be easily wound into the coiled segment 1900 and can be taped (e.g., with Tegaderm™ or other biocompatible adhesives, bandages, or dressings) to the skin of the patient (see FIG. 19C). Coiling the tracking wire 932 can reduce the length of the excess segment of the tracking wire 932 extending out of the patient's tissue and can ensure that the excess segment of the tracking wire 932 will not interfere with the patient while wearing normal clothing or dressing or will not prevent the patient from sleeping normally.

The secure retention properties of the localization element 932 within the tissue site, combined with the suture-like flexibility of the tracking wire can enable a breast patient to go home after placement of the localization element. Prior to this device, current localization wires are too prone to movement and are too stiff to allow the patient to return to home with localization wire in place. This attribute is important because this enables the localization procedure to be de-coupled from the surgical tissue removal procedure (e.g. lumpectomy). This has valuable clinical scheduling implications because with the use of this device, the surgeon no longer has to rely on the localization element to be placed the day of the scheduled surgical excision (e.g. lumpectomy), eliminating delays and operating room scheduling uncertainties, which can be costly to the healthcare system.

Figure 20A:
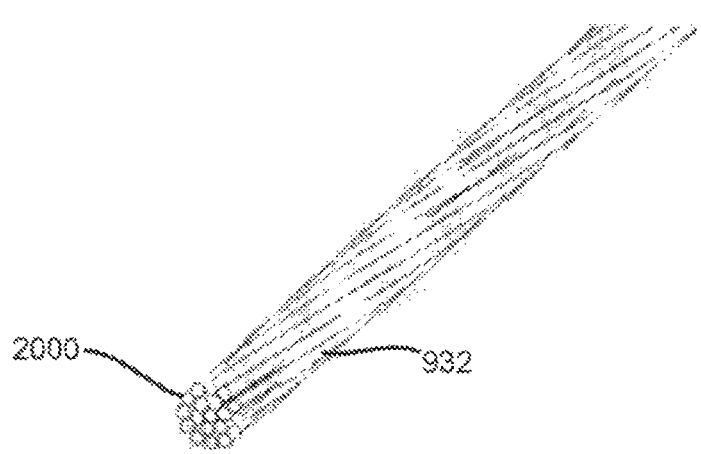
FIG. 20A illustrates a distal end of a multi-filament tracking wire.

FIG. 20A illustrates that the tracking wire 932 can be fabricated from a cable that is composed of a number of filaments 2000. For example, the cable of the tracking wire 932 can comprise or be composed of a multi-filament (e.g., 19-filament) wire, where each filament is composed of stainless steel, tungsten, or other material. In other variations, the tracking wire 932 can comprise or be composed of between seven and 31 filaments 2000. Each of the filaments 2000 can have a filament diameter. In some variations, the filament diameter can be between approximately 0.025 mm and 0.035 mm. For example, the filament diameter can be approximately 0.030 mm. The tracking wire 932 can also have a wire diameter, the wire diameter can be between approximately 0.150 mm and 0.155 mm. For example, the wire diameter can be approximately 0.152 mm. The cable can alternatively be comprised of polymer fibers which can have an even greater strand count (e.g., up to 100 polymer strands), and can have a different diameter. For example, the wire diameter can alternatively be between approximately 0.125 mm and 0.255 mm.

Figure 20B:
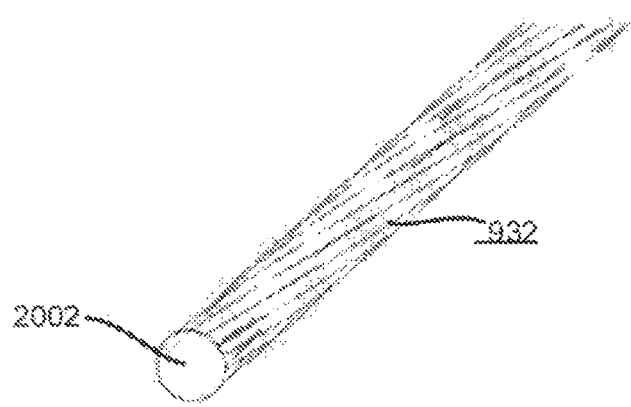
FIG. 20B illustrates a distal end of a multi-filament tracking wire having a welded end.
Figure 20C:
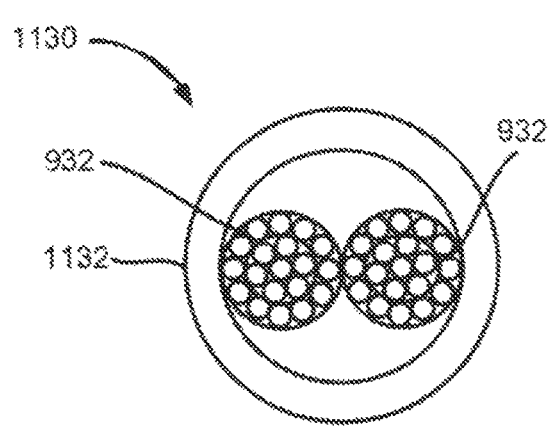
FIGS. 20C-D illustrate an example cross-section of an attachment site of a multi-filament tracking wire covered by a polymer jacketing.
Figure 20D:
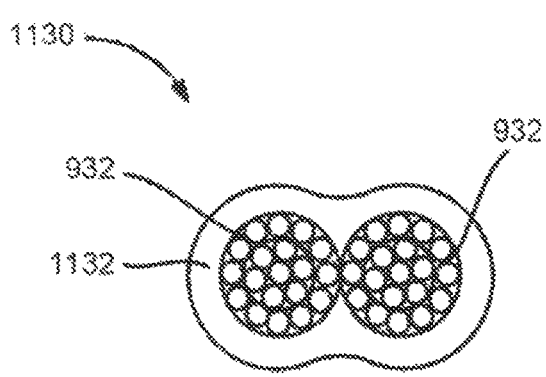

FIG. 20B illustrates that a distal end of the tracking wire 932 can have a welded tip 2002 to capture and join together the plurality of filament ends. FIG. 20C illustrates that a polymer jacketing 1132 can ensheath or otherwise surround the attachment site 1130 of the tracking wire 932. The polymer jacketing 1132 can be made of heat-shrinkable material and can thus conform more closely to the underlying cables of the tracking wire 932. FIG. 20C illustrates a cross-section of the tracking wire 932 prior to the polymer jacketing 1132 undergoing the heat-shrinking process, and FIG. 20D is a cross-section illustrating the polymer jacketing 1132 conforming to the tracking wire 932 after undergoing heat-shrinking. The attachment site 1130 can be a site or segment along the tracking wire 923 where one segment of the tracking wire 932 is attached to another segment of the tracking wire 932. For example, the wire distal end 936 can be threaded through the aperture 1108 within the eyelet frame 1106 and looped back to align with a more proximal segment of the tracking wire 932. The wire distal end 936 can then be welded to the more proximal segment of the tracking wire 932 and the weld site can be referred to as the attachment site 1130.

The polymer jacketing 1132 may surround a portion of the tracking wire 932 in proximity to the attachment site 1130 between the tracking wire 932 and the localization element 930, or the polymer jacketing 1132 may extend a length of the tracking wire 932. The polymer jacketing 1132 can also be used to identify lengths of the tracking wire 932. For example, an additional layer of the polymer jacketing 1132 can be disposed around an approximately 3 cm long portion of the tracking wire 932 at a distal end of the wire 932. The additional layer of jacketing 1132 can change the feel of the wire 932 to a surgeon using the tracking wire 932 to locate a target tissue site, identifying to the surgeon when he/she is approaching the distal end of the tracking wire 932. Additional layers of the jacketing 1132 may alternatively be disposed at other locations along the tracking wire 932, such as every 2 cm along its length. Alternatively, one or more metallic ferrules (e.g. stainless steel, tantalum) may be placed at one or more locations along the length of the tracking wire 932 (e.g. beneath the polymer jacketing) to signify various levels of proximity to the localization element 930. Other depth marking methods may include printing or the use of different colored polymer segments.

The polymer jacketing 1132 can be composed of one or more polymers, such as polyolefin, polyvinyl chloride (PVC), or a thermoplastic elastomer (e.g., PEBAX™). By enclosing at least a portion of the tracking wire 932 in a polymer jacketing 1132, wear and risk of damage to the tracking wire 932 may be reduced. In addition, the polymer jacketing 1132 may also reduce snagging or fraying of the tracking wire 932.

Figure 21:
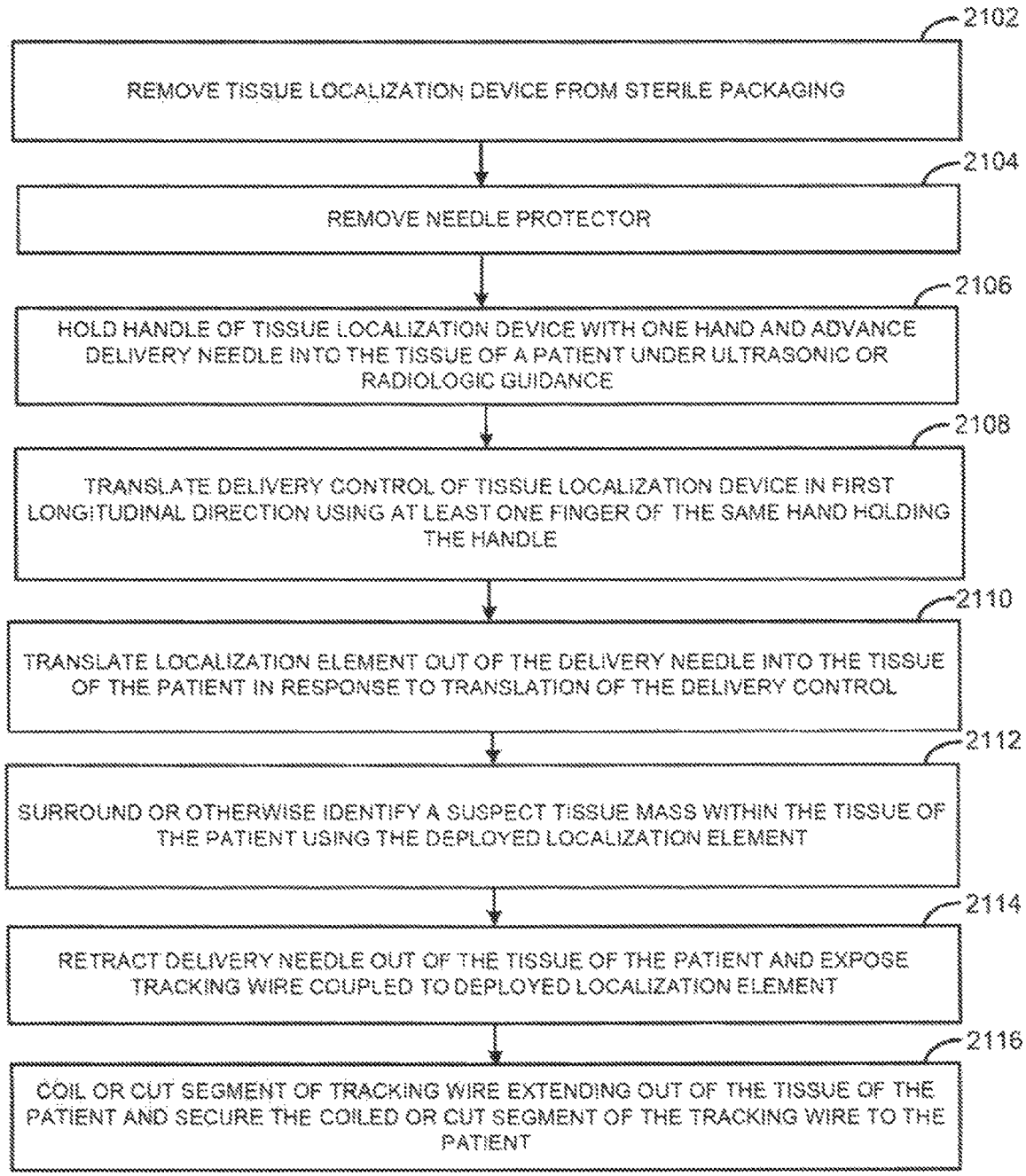
FIG. 21 illustrates a variation of a method of operating the tissue localization device.

FIG. 21 illustrates a method 2100 of operating the tissue localization device 900. The method 2100 can involve removing the tissue localization device 900 from a sterile package in operation 2102. The method 2100 can also involve removing a needle protector covering the delivery needle 906 in operation 2104. The method 2100 can further involve holding the handle 902 of the tissue localization device 900 with one hand and advancing the delivery needle 906, under ultrasonic or radiologic guidance, into the tissue of the patient until the distal end 1400 of the delivery needle 906 is adjacent to a suspect tissue mass (or other target tissue site) 1802 in operation 2106. The method 2100 can further involve translating or pushing the delivery control 904 of the tissue localization device 900 in a first longitudinal direction 1004 using at least one finger of the same hand holding the handle 902 in operation 2108.

The method 2100 can further involve translating the localization element 930 of the tissue localization device 900 out of the delivery needle 906 in response to the translation of the delivery control 904 in operation 2110. The localization element 930 can be deployed out of the distal end 1400 of the delivery needle 906 when a delivery port 1118 of a pusher element 920 holding the localization element 930 is advanced out of the needle lumen 918. If the localization element 930 is not deployed in a desired path, the localization element 930 can be retracted into the needle lumen after at least part of the localization element 930 is deployed out of the delivery needle 906. The delivery needle 906 can subsequently be repositioned. For example, the delivery needle 906 can be rotated about a longitudinal axis of the delivery needle 906 (e.g., to achieve a desired deployment path for the localization element 930), and the localization element 930 can be redeployed out of the delivery needle 906 into the tissue.

The method 2100 can further involve surrounding, encircling, or otherwise identifying the suspect tissue mass 1802 using the deployed localization element 930 in operation 2112. The localization element 930 can form into the deployed configuration 942 around the suspect tissue mass 1802 or above the suspect tissue mass 1802. The localization element 930 can automatically disengage or detach from the pusher element 920 when the delivery port 1118 of the pusher element 920 is advanced out of the needle lumen 918.

The method 2100 can further involve retracting the beveled distal end 1400 of the delivery needle 906 away from the suspect tissue mass 1802 and exposing the tracking wire 932 coupled to the localization element 930 in operation 2114. The method 2100 can also involve coiling and/or cutting the segment of the tracking wire 932 extending out of the tissue of the patient and securing (e.g., using Tegaderm™ or another biocompatible adhesive or dressing) the coiled or cut segment of the tracking wire 932 directly or indirectly to the skin or patient dressing of the patient in operation 2116. By doing so, the tracking wire 932 extending out of the body of the patient can be secured closer to the body of the patient (e.g., flush with the skin surface) such that the tracking wire 932 is not inadvertently pulled or displaced. At this point, the patient can be sent home from the procedure and asked to return the following day to surgically excise the localized tissue mass 1802 from the patient, or the suspect tissue mass 1802 can be excised the same day. The same facility which placed the localization element 930 into the body of the patient can perform the excision procedure such as the lumpectomy.

Figure 22:
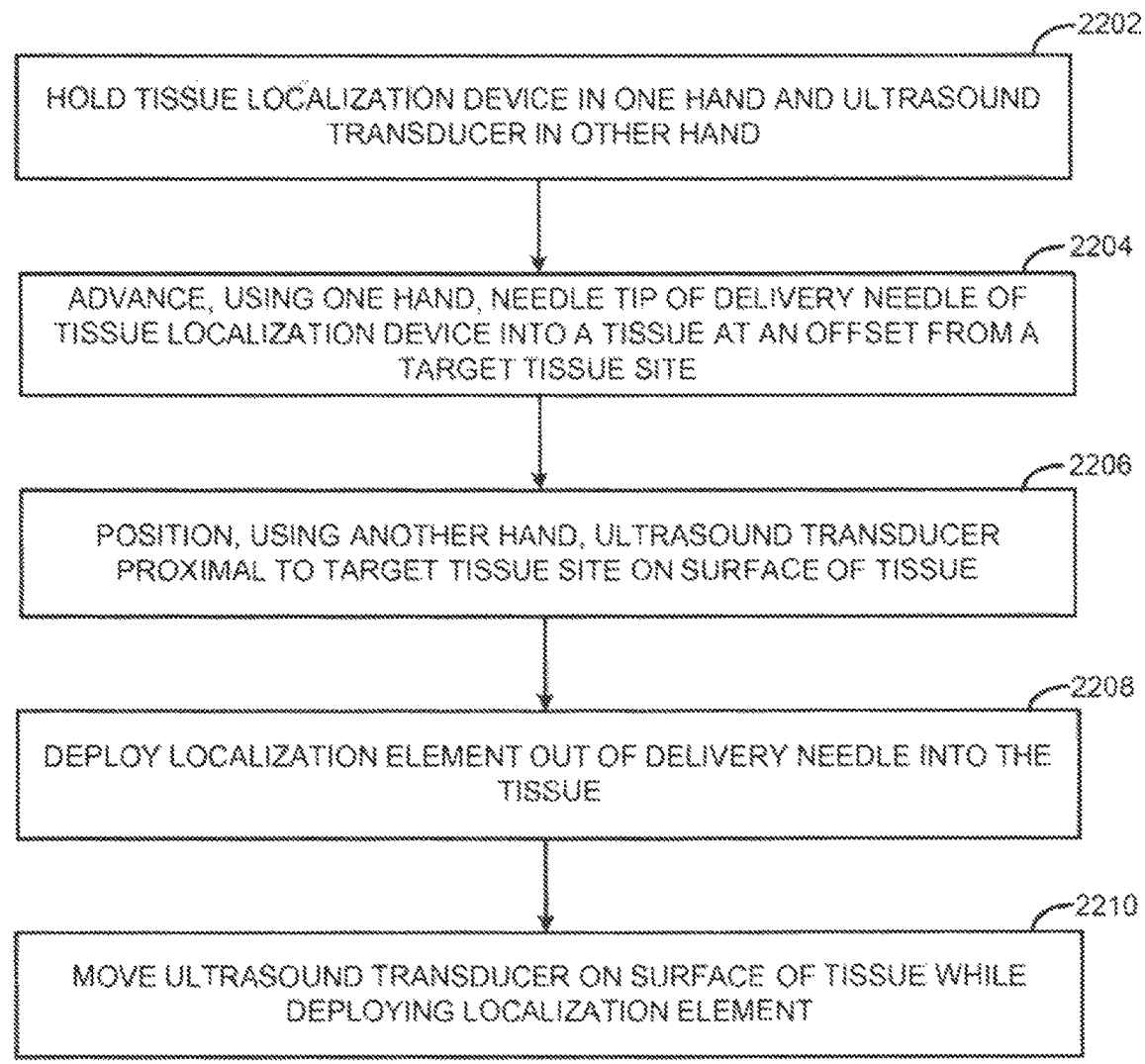
FIG. 22 illustrates another variation of a method of operating the tissue localization device.

FIG. 22 illustrates a method 2200 for using a tissue localization device to localize tissue. The method 2200 is described with respect to FIGS. 23A-G.

Figure 23A:
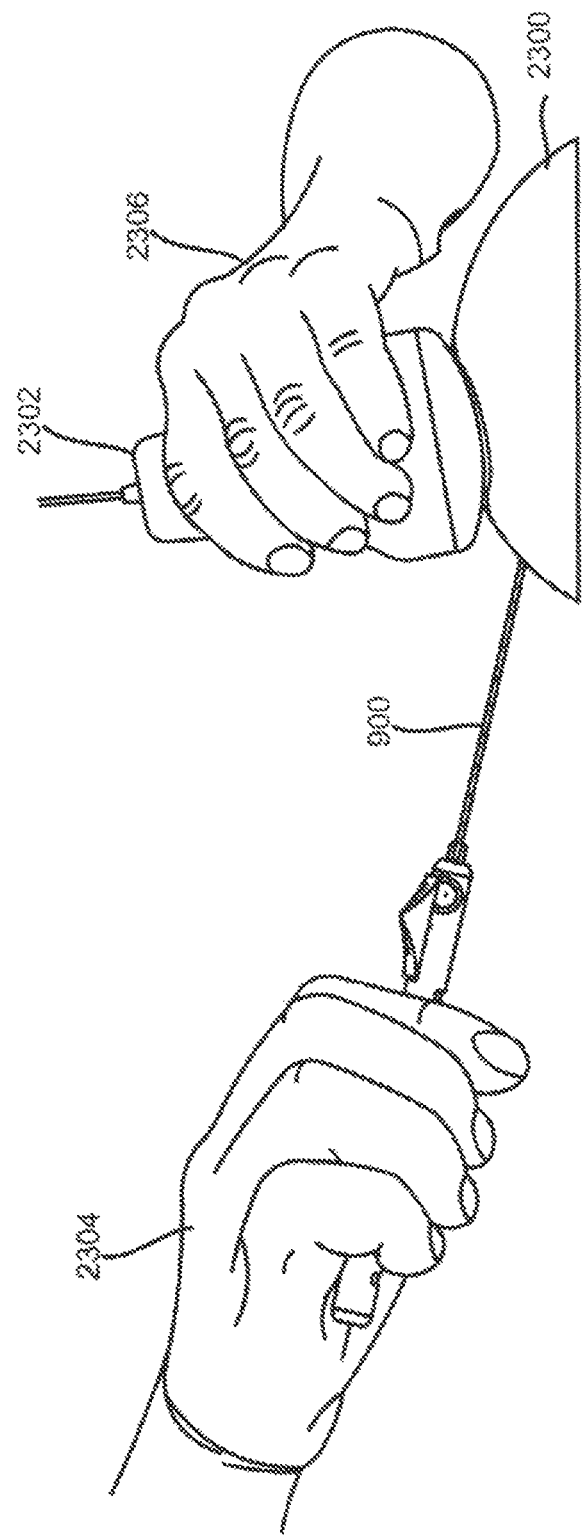
FIGS. 23A-G illustrate a variation of a method of operating the tissue localization device.
Figure 23B:
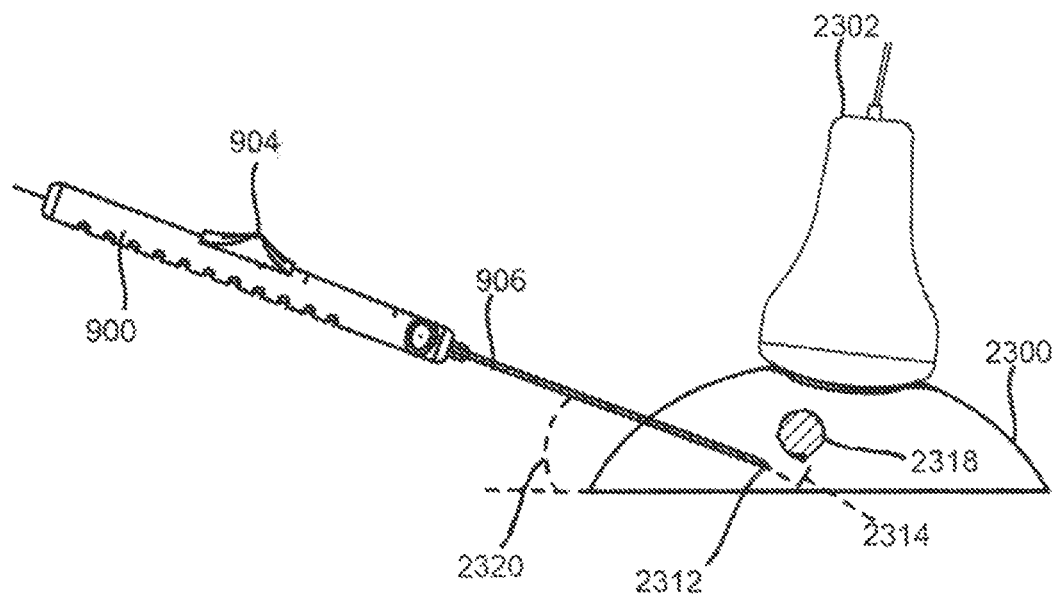
Figure 23C:
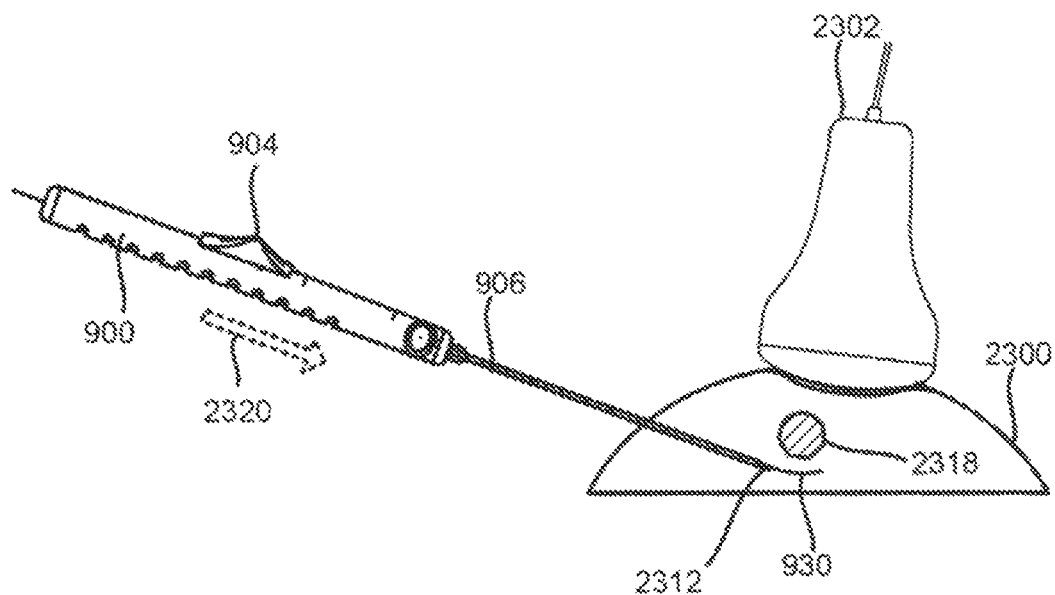

The method 2200 can include holding the tissue localization device in one hand while holding an ultrasound transducer in another hand (2202). For example, FIG. 23A shows a user holding the tissue localization device 900 in a first (e.g., right) hand 2304 while holding an ultrasound transducer 2302 in a second (e.g., left) hand 2306. The method 2200 is described with respect to use of the tissue localization device 900, the user may alternatively hold the tissue localization device 100 in the first hand 2304. The tissue localization device 900 and ultrasound transducer 2302 can each be operable with a single hand of the user, and sized to fit within a single hand of the user. Thus, the user can concurrently operate both the tissue localization device 900 and the ultrasound transducer 2302.

The method 2200 can include advancing, using one hand, a needle tip 2312 of the delivery needle 906 into a tissue 2300 at an offset from a target tissue site 2318 in step 2204. The target tissue site can include a suspect tissue mass such as a tumor or lesion, a volume of tissue immediately surrounding a suspect tissue mass, or any other volume of the tissue 2300. To reduce a distance the needle 906 travels through the tissue 2300, the needle 906 can be advanced at an angle 2320 from a base of the tissue 2300. For example, if the tissue 2300 is breast tissue of a patient, the needle 906 can be advanced at an angle 2320 from a chest plane of the patient. The angle 2320 may depend on a size of the tissue 2300, a size of the localization element 930, a size of the target tissue site 2318, orientation of the tissue localization device 900 with respect to the tissue, or other factors. For example, the angle 2320 is small enough that the localization element 930 when deployed will not pass through a surface of the tissue 2300, but large enough to reduce, where possible, the distance the needle 906 travels through the tissue 2300.

The needle tip 2312 can be advanced into the tissue 2300 until positioned in a plane intersecting the target tissue site, a plane proximal to the target tissue site, or a plane distal to the target tissue site, while offset from the target tissue site 2318. The offset can be a threshold distance from an edge of the target tissue site such that the localization element 930 when deployed does not intersect the target tissue site. As shown for example in FIG. 23B, the needle tip 2312 is offset from the target tissue site 2318 by a distance 2314. The offset can be toward a side of the target tissue site 2318 distal to the user of the tissue localization device 900. For example, if the patient is lying on her back while the method 2200 is performed, the needle tip 2312 can be offset toward the patient's dorsal side relative to the target tissue site 2318.

The offset from the target tissue site can be limited based on a diameter of the localization element 930 when deployed and a size of the target tissue site 2318. For example, the distance 2314 is less than a difference between a diameter of the localization element and a diameter of the target tissue site, enabling the localization element 930 when deployed to radially surround at least part of the target tissue site without intersecting the target tissue site. Alternatively, the needle tip 2312 may be offset from the target tissue site 2318 in a plane proximal or distal to the target tissue site 2318. For example, the needle tip 2312 may be offset proximal to the target tissue site 2318 such that the localization element is deployed as illustrated in FIG. 18B, in which a curvature plane formed by the deployed localization device 930 does not intersect the target tissue site 2318. The user can use the slidable delivery control 904 to determine an expected direction of curvature of the localization element 930. For example, the localization element 930 may curve toward a side of the tissue localization device 900 on which the slidable delivery control 904 is disposed. The slidable delivery control 904 can alternatively identify the expected direction of curvature of the localization element 930 in other ways.

The method 2200 can further include positioning, using another hand, the ultrasound transducer 2302 proximal to the target tissue site on a surface of the tissue (2206). For example, referring again to FIG. 23B, the ultrasound transducer 2302 is positioned on a surface 2316 of the tissue 2300, proximal to the target tissue site 2318. The ultrasound transducer 2302 can be positioned on the tissue surface 2316 while the tissue localization device 900 is inserted into the tissue 2300.

The method 2200 can further include deploying the localization element 930 out of the delivery needle 906 into the tissue (2208). The localization element 930 can be deployed by pushing a slidable delivery control 904 in a first longitudinal direction along the tissue localization device 900. For example, in FIG. 23C, the slidable delivery control 904 is pushed in a first longitudinal direction 2320 along the tissue localization device 900 (e.g., toward a distal end of the tissue localization device 900) to deploy the localization element 930 from the delivery needle 906. In other variations, the localization element 930 can be deployed in other ways, such as by turning a knob in a first rotational direction. While the localization element 930 is being deployed, the ultrasound transducer 2302 can be used to view a position of the localization device 930 in the tissue and verify that the localization device 930 is deployed to surround or otherwise identify the target tissue site 2318 without intersecting the target tissue site.

Figure 23D:
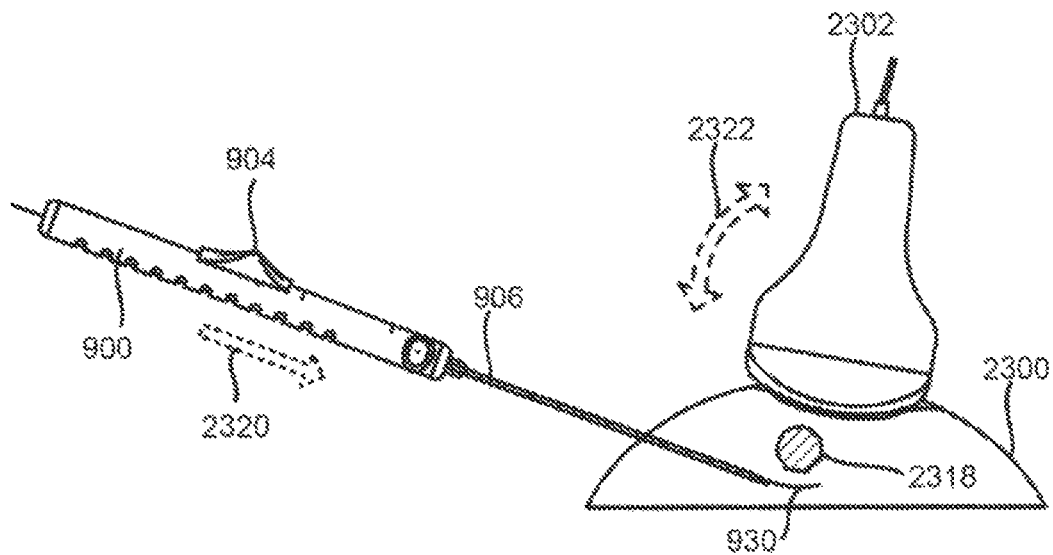
Figure 23E:
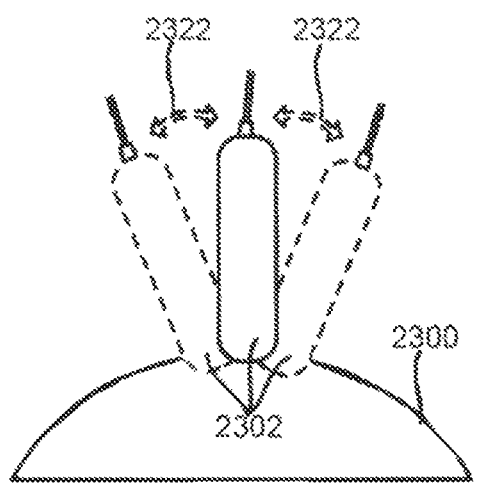

The method 2200 can further include moving the ultrasound transducer 2302 on the tissue surface while deploying the localization element 930 in step 2210. The ultrasound transducer 2302 can be moved on the tissue surface 2316 in a number of different ways, including translation across the surface (e.g., while remaining perpendicular to the surface) and rotation around axes of the ultrasound transducer (e.g., yaw, pitch, or roll rotation). FIG. 23D illustrates an example of the ultrasound transducer 2302 moved on the surface 2316 of the tissue 2300 in a pitch rotation 2322 around a transverse axis of the ultrasound transducer 2302, concurrently with the deployment of the localization element 930. FIG. 23E is a schematic illustrating a side view of the pitch rotation 2322 shown in FIG. 23D. By moving the ultrasound transducer 2302 in the pitch rotation 2322, the position of the localization element 930 can be better visualized, for example if the localization element 930 passes out of an image window detectable by the ultrasound transducer 2302, or if the target tissue site 2318 partially or fully obscures the localization element 930 from detection by the original position of the ultrasound transducer 2302. Other movements of the ultrasound transducer 2302 may similarly improve visualization of the localization element 930 as the element is deployed.

Figure 23F:
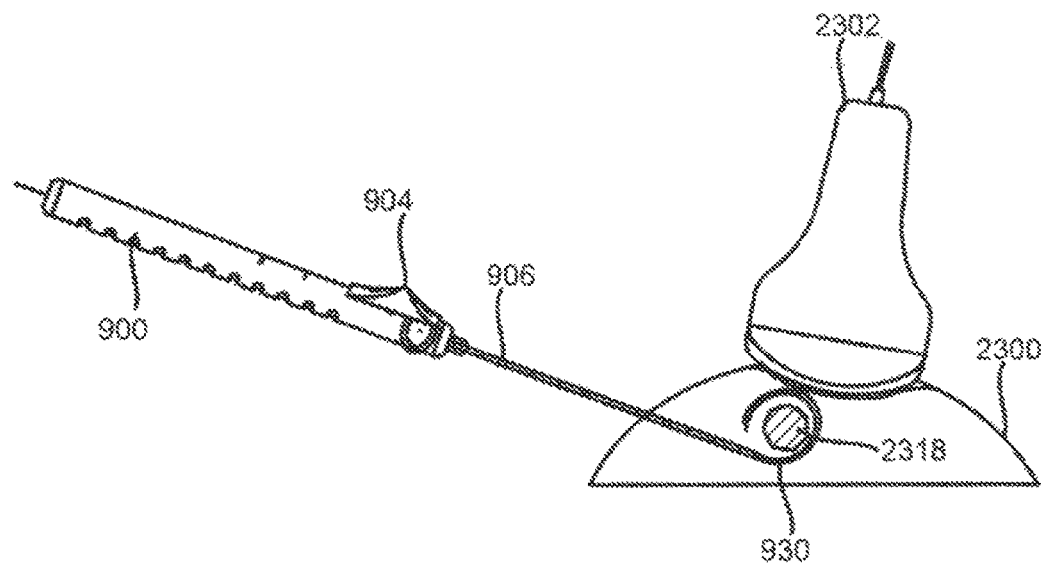

The localization element 930 can continue to be deployed out of the delivery needle 906, while the ultrasound transducer 2302 is moved as desired, until the localization element 930 has been completely deployed from the delivery needle 906. FIG. 23F illustrates an example of the localization element 930 deployed to at least partially surround the target tissue site 2318. During deployment of the localization element 930, the localization element 930 can be retracted into the delivery needle 906 if, for example, the user desires to change the position of the localization element 930 in the tissue. The localization element 930 can be retracted by moving the slidable delivery control 904 in a second longitudinal direction opposite the first longitudinal direction 2320 (e.g., toward a proximal end of the tissue localization device 900). The localization element 930 may in other variations be retracted by other mechanisms, such as by turning a knob in a second rotational direction opposite the first rotational direction. Retracting the localization element 930 can allow the user to adjust a starting position or direction of curvature of the localization element 930 in the tissue 2300. For example, if the user determines the localization element 930 is deploying along a curvature path different from a desired path, the user can retract the localization element 930 into the delivery needle 906, rotate the tissue localization device 900 around a longitudinal axis, and begin redeploying the localization element 930. The user can alternatively change a position of the needle tip in the tissue 2300. When fully deployed from the delivery needle 906, the localization element 930 may automatically disengage or detach from the tissue localization device 900.

Figure 23G:
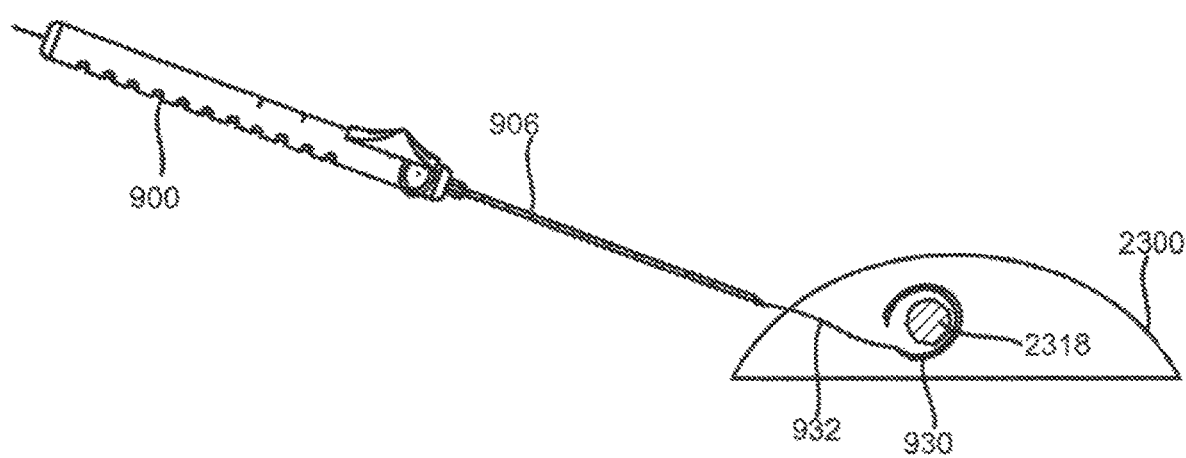

The method 2200 can further include, in step 2212, removing the delivery needle 906 from the tissue 2300 and exposing the tracking wire 932 coupled to the localization element 930. FIG. 23G illustrates the tracking wire 932 extending out of the tissue 2300 after the delivery needle 906 is removed from the tissue 2300. The tracking wire 932 can be coiled or cut and secured to the body of the patient.

Figure 24A:
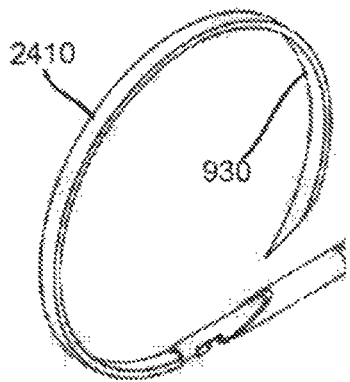
FIGS. 24A-G illustrate examples of a localization element surface.
Figure 24B:
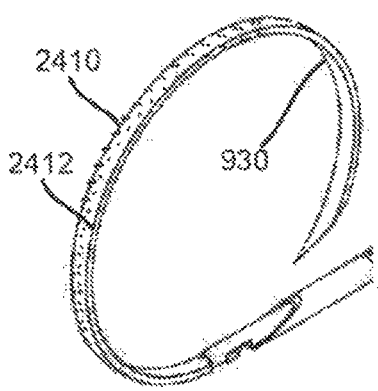
Figure 24C:
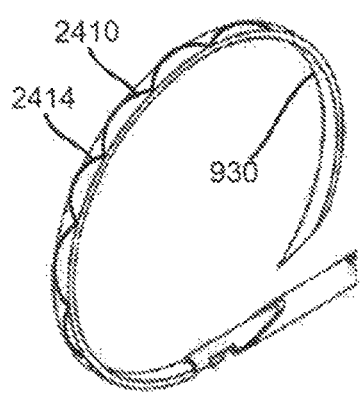
Figure 24D:
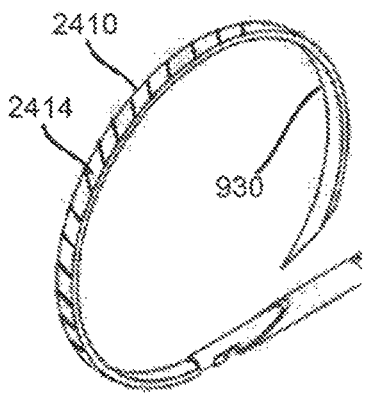
Figure 24E:
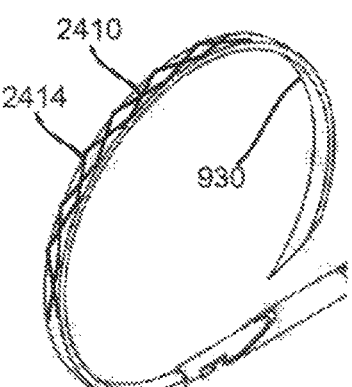
Figure 24F:
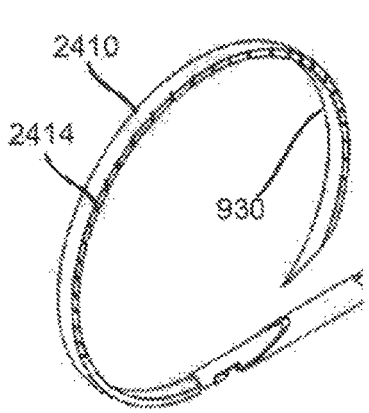

FIGS. 24A-G illustrate several variations of the localization element 930. As illustrated in FIG. 24A, the localization element 930 may have a surface 2410 that is substantially smooth. For example, the surface 2410 may be polished by electrochemical, electrolytic, or mechanical polishing. In other variations, the localization element surface 2410 may include an echogenic surface treatment, or a surface roughness to increase the echogenicity of the localization element 930 for improved visualization under ultrasound. FIG. 24B illustrates a surface roughness 2412 achieved by abrasive blasting of the localization element 930, such as sandblasting or bead blasting. FIGS. 24C-F illustrate various example patterns 2414 cut into the localization element surface 2410 by laser cutting, laser etching, or other surface cutting mechanism. FIGS. 24C-E illustrate that the patterns 2414 can be cut into an exterior surface of the localization element 930, while FIG. 24F illustrates that a pattern can be cut into a side of the localization element 930. Patterns or other echogenic surface treatments may alternatively be applied to an interior surface of the localization element 930, or can be applied to a combination of the exterior, side edge, and interior surfaces of the localization element 930.

Other patterns than those shown in FIGS. 24C-E may alternatively be cut into the localization element surface 2410, and random lines, dots, or other shapes can be used instead of patterned cuts. For example, a grid of dots may alternatively be cut into the localization element surface 2410. The patterns or shapes may be cut to a depth between 0% and approximately 25% of a thickness of the localization element 930. Each cut into the localization element surface 2410 can be at least as deep into the surface 2410 as it is wide, or can have a depth that is greater than its width. The width of each cut can be, for example, approximately 0.001 to 0.006 inches. The patterns 2414 or random lines, dots, or other structures may alternatively protrude from the localization element surface 2410.

Figure 24G:
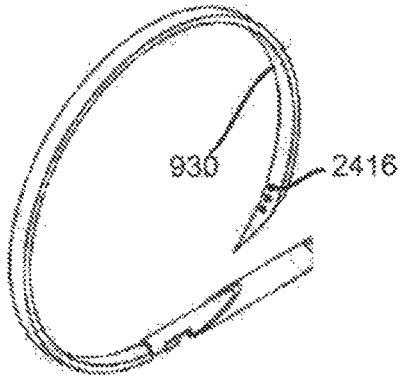

As illustrated for example in FIG. 24G, one or more holes 2416 can be created through the localization element 930 (e.g., radially from the interior surface to the exterior surface of the localization element 930). The one or more holes 2416 can be created (e.g. drilled or laser cut) near a distal tip of the localization element 930, as illustrated in the example of FIG. 24G, or can be created at other locations along the localization element 930.

Figure 25A:
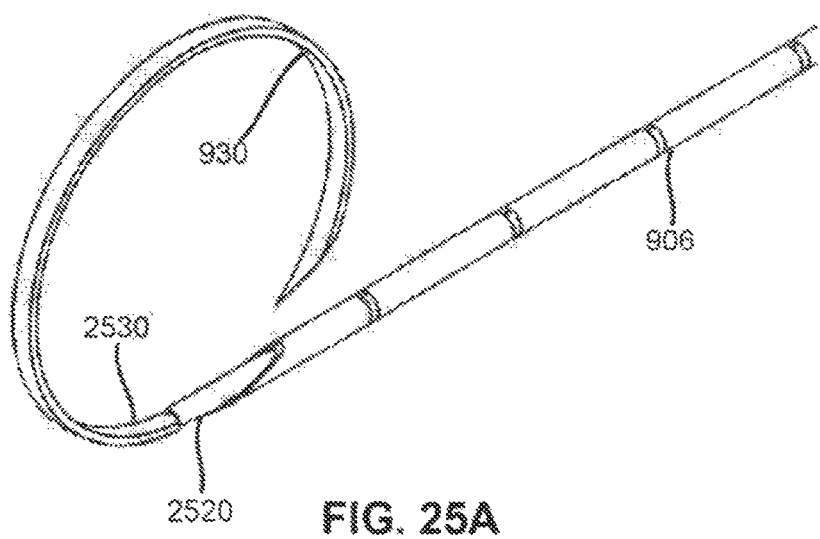
FIGS. 25A-C illustrate a variation of a pusher element.
Figure 25B:
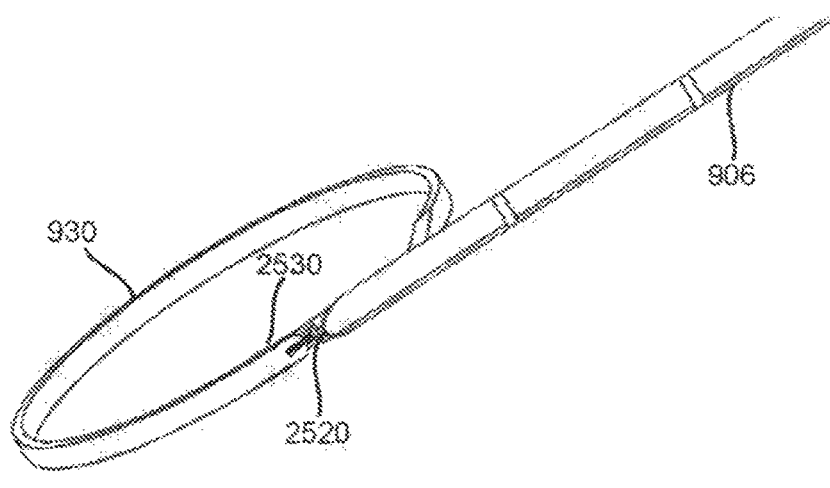
Figure 25C:
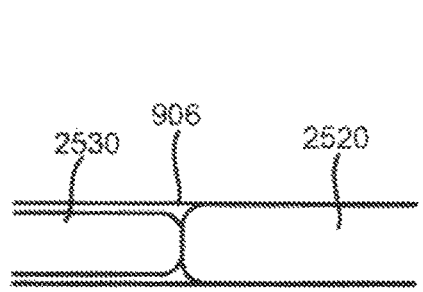

As described above with respect to FIGS. 11A-B, the tissue localization device 900 can include a pusher element 920 that, in addition to deploying the localization element 930 from the tissue localization device 900, can retract the localization element 930 into the tissue localization device 900. FIGS. 25A-B illustrate that the tissue localization device 900 can include a pusher element 2520 configured to deploy the localization element 930 from the tissue localization device 900 but not retract the localization element 930. FIG. 25C illustrates a cross-section of a non-retractable pusher element 2520 shown in FIGS. 25A and 25B while inside the delivery needle 906. As shown in FIG. 25C, the distal terminal end of the pusher element 2520 can abut, contact and push against a proximal terminal end 2530 of the localization element 930. Sliding the slidable delivery control 904 toward a distal end of the tissue localization device 900 (e.g., toward the left side of FIG. 25C) can cause the pusher element 2520 to push on the proximal end 2530 of the localization element 930, thereby deploying the localization element 930 from the delivery needle 906. However, sliding the slidable delivery control 904 toward a proximal end of the tissue localization device 900 (e.g., toward the right side of FIG. 25C) can retract the pusher element 2520 away from the proximal end 2530 of the localization element 930 until the pusher element 2520 is no longer in contact with the localization element 930, without applying force to the localization element 930 sufficient to retract the localization element 930 into the tissue localization device 900. The shape of the face of the distal terminal end of the pusher element 2520 can be the inverse of the shape of the face of the proximal terminal end 2530 of the localization element 930. For example, the respective faces can be perpendicular to the respective longitudinal axes, as shown in FIG. 25C.

Figure 26:
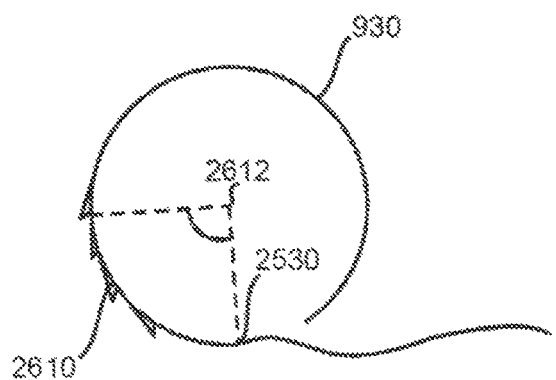
FIG. 26 illustrates a variation of a localization element including one or more barbs.

FIG. 26 illustrates that the localization element 930 can include one or more barbs 2610 protruding from the localization element 930. The barbs 2610 can limit retractibility of the localization element 930, or can help secure the localization element 930 in tissue. The barbs 2610 can protrude from some portion or an entire length of the localization element 930. For example, the localization element 930 can include barbs 2610 near a proximal end 2530 of the localization element 930, within an angle 2612 of the proximal end 2530. The angle 2612 may be any percentage of the deployed configuration of the localization element 930. The angle 2612 can be between approximately 10% and 25% of the circumference of the deployed configuration of the localization element 930. Alternatively, the angle 2612 can be up to 100% of the deployed configuration of the localization element 930. Although FIG. 26 illustrates the barbs 2610 protruding from an exterior surface of the localization element 930, the barbs can additionally or alternatively protrude from a side edge or interior surface of the localization element 930.

The barbs 2610 shown in FIG. 26 can provide resistance against retraction of the localization element 930 after one or more of the barbs 2610 have entered the tissue of a patient. For example, the localization element 930 may be retractable while a distal portion is deployed into the tissue of a patient and the proximal end remains inside the delivery needle 906 of the tissue localization device 900. However, the localization element 930 may not be retractable, or may have limited retractability, after a portion of the localization element 930 including a barb 2610 has been deployed into the tissue.

Figure 27:
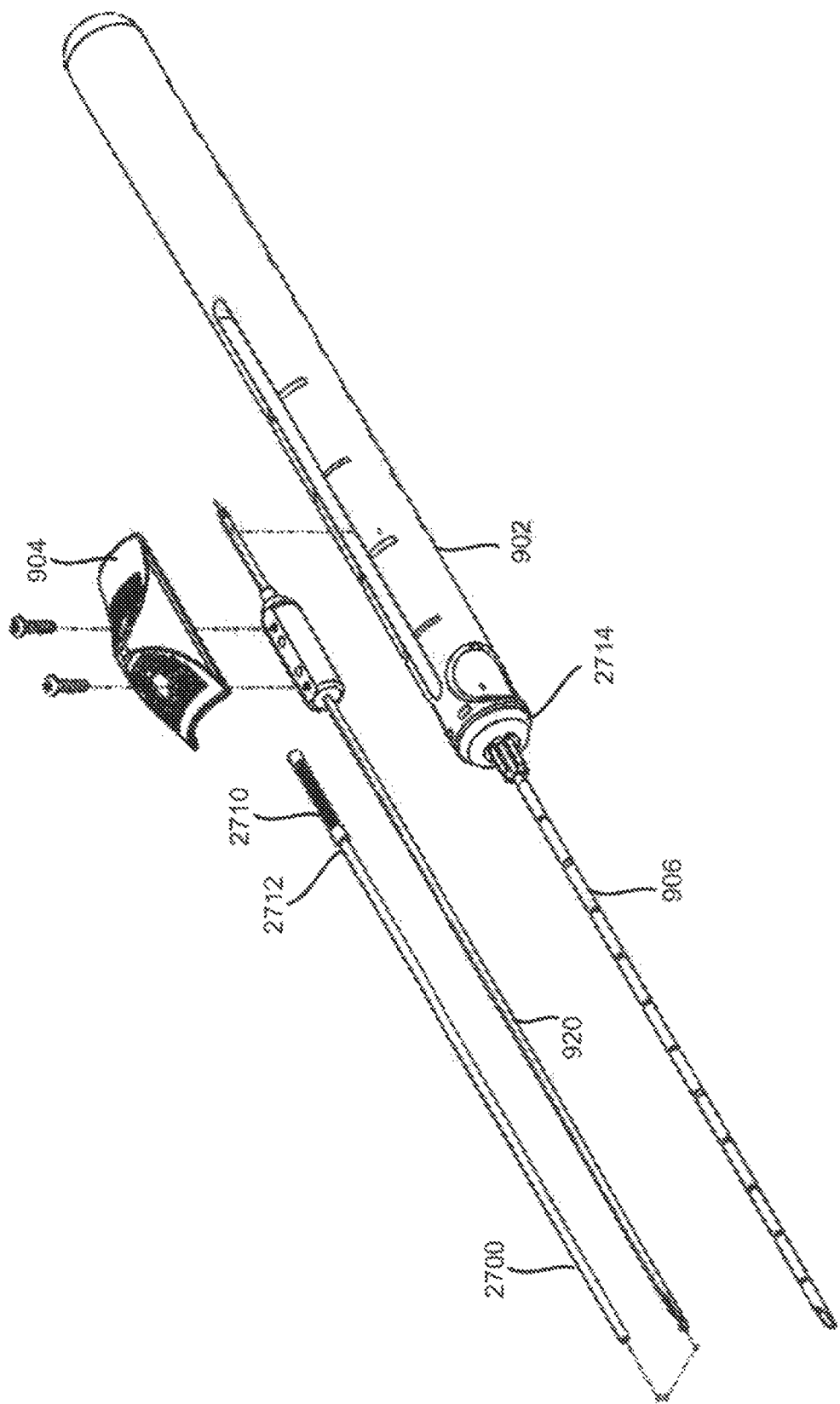
FIG. 27 illustrates a variation of the tissue localization device including a stainless steel liner.

As shown in FIG. 12, the tissue localization device 900 can include a polymer liner 1200 encasing or surrounding at least a portion of the pusher element 920. FIG. 27 illustrates that the tissue localization device 900 can include a stainless steel liner 2700. Other aspects of the tissue localization device 900 can be similar to aspects described with respect to FIGS. 9 and 12. The stainless steel liner 2700 can be radially between at least part of the localization element 930 and a needle lumen of the delivery needle 906. For example, the stainless steel liner 2700 can be a substantially cylindrical tube having a hollow lumen, and can radially surround at least a portion of the localization element 930. The stainless steel liner 2700 optionally can also radially surround at least a portion of the pusher element 920. The delivery needle 906 of the tissue localization device 900 in turn can radially at least part of the stainless steel liner 2700 and the pusher element 920.

The stainless steel liner 2700 can completely encircle or radially surround the pusher element 920 such that no contact is made between the external surface of the pusher element 920 and the delivery needle 906 as the pusher element 920 is translated longitudinally through the delivery needle 906. In another variation, the liner 2700 can cover a dorsal side of the pusher element 920 or localization element 930 to limit the pusher dorsal side or localization element dorsal side from contacting an inner dorsal surface of the delivery needle 906 as the pusher element 920 and localization element 930 are translated longitudinally. The liner 2700 can cover a ventral side of the pusher element 920 or localization element 930 to limit the pusher ventral side or localization element ventral side from contacting an inner ventral surface of the delivery needle 906 as the pusher element 920 and localization element 930 are translated longitudinally.

The stainless steel liner 2700 can be slidably translatable within the delivery needle 906. The stainless steel liner 2700 and pusher element 920 can be coupled to the slidable delivery control 904, such that translation of the slidable delivery control 904 in a first longitudinal direction (e.g., toward a distal end of the delivery needle 906) causes the stainless steel liner 2700 and localization element 930 to translate toward the distal end of the delivery needle 906. The liner 2700 can accommodate release of the localization element 930 from the pusher element 920. For example, the localization element 930 can be releasable from the liner when a distal end of the pusher element 920 is translated longitudinally beyond the liner. The liner 2700 can have a wall thickness of approximately 0.002 to 0.004 inches.

The tissue localization device 900 can further include a spring 2710. The spring 2710 can be coupled to a proximal end of the stainless steel liner 2700, and a distal end 2712 of the spring 2710 can push or pull the liner 2700 to slide longitudinally through the delivery needle 906 in response to longitudinal translation of the slidable delivery control 904. The spring 2710 is configured to compress in response to distal translation of the slidable delivery control 904 when a distal end 2712 of the spring 2710 contacts a distal end 2714 of the tissue localization device handle 902. While the spring 2710 compresses, the spring 2710 stops translation of the stainless steel liner 2700 and enables the pusher element 906 to translate relative to the liner 2700. Thus, while the spring 2710 is uncompressed, the pusher element 920 and stainless steel liner 2700 can be configured to translate together toward a distal end of the delivery needle 906 in response to a distal translation of the slidable delivery control 904. However, while the spring 2710 is at least partially compressed, the pusher element 920 can be configured to translate toward the distal end of the delivery needle 906, relative to the liner 2700, in response to the distal translation of the slidable delivery control 904.

Figure 28A:
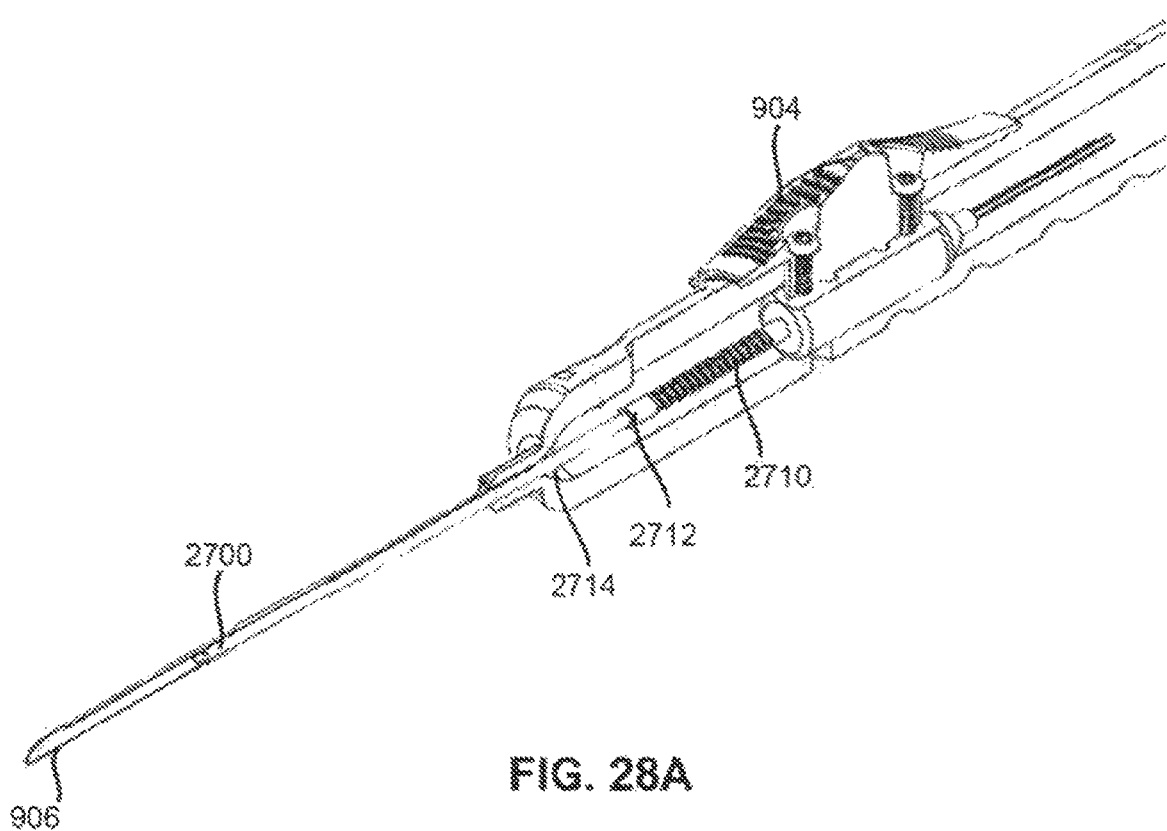
FIGS. 28A-B illustrate an example of a spring coupled to the stainless steel liner.
Figure 28B:
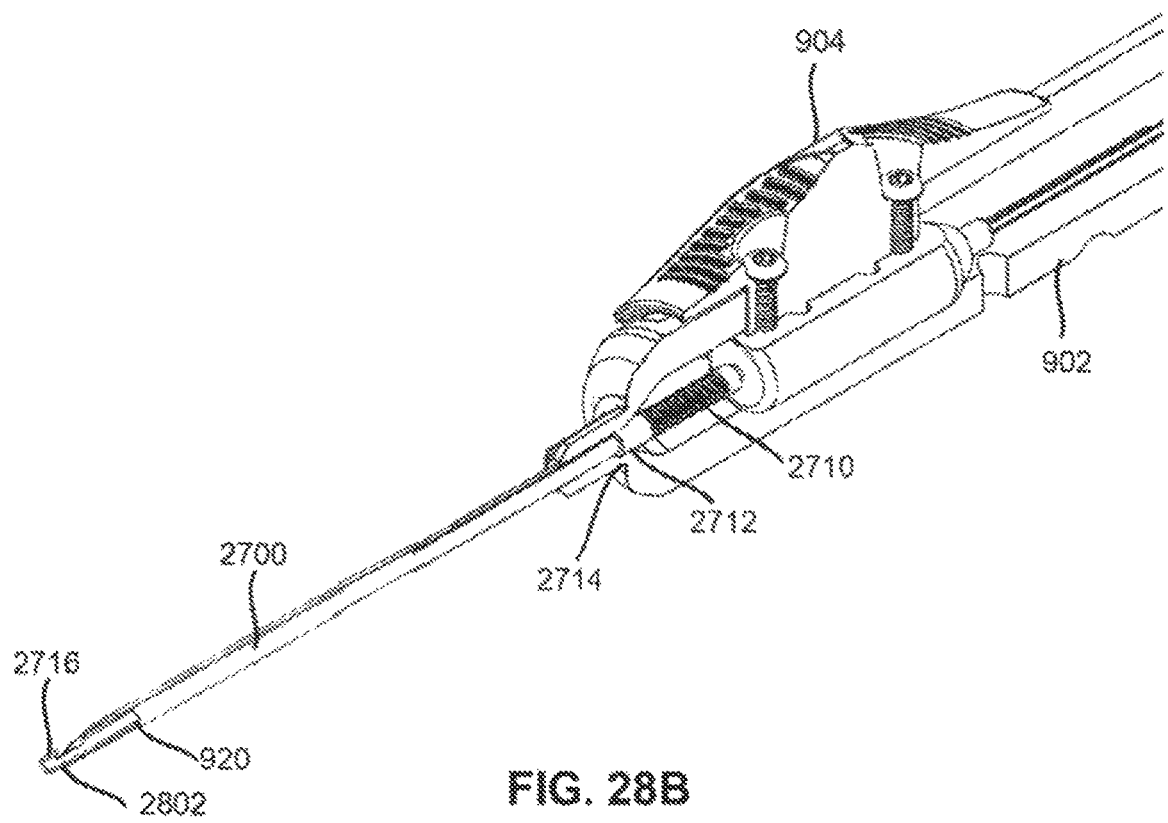

FIG. 28A illustrates an example of the stainless steel liner 2700 and spring 2710 prior to compression of the spring 2710, while FIG. 28B illustrates partial compression of the spring 2710 allowing translation of the pusher element 920 relative to the liner 2700. As shown in FIG. 28A, the spring 2710 may be short enough to not contact the handle distal end 2714 through a portion of a range of motion of the slidable delivery control 904. Sliding the slidable delivery control 904 during that portion of the range of motion may therefore also move the spring 2710 and liner 2700 through the handle 902 and needle 906. FIG. 28B illustrates the distal end 2712 of the spring 2710 in contact with the distal end 2714 of the tissue localization device handle 902. The handle distal end 2714 can have a smaller diameter than the spring 2710 to stop translation of the spring distal end 2712. Alternatively, the handle 902 may include a block or other mechanism at the handle distal end 2714 to prevent translation of the spring distal end 2712 toward a distal end of the tissue localization device 900. When the spring distal end 2712 contacts the handle distal end 2714, further distal translation of the slidable delivery control 904 can compress the spring 2710.

Because the stainless steel liner 2700 is coupled to the spring 2710, the liner 2700 may not translate through the delivery needle 906 while the spring 2710 is at least partially compressed. However, distal translation of the slidable delivery control 904 may continue to push the pusher element 920 toward the distal end of the delivery needle 906, even after the spring 2710 has started to compress. Accordingly, the pusher element 920 can be translated relative to the liner 2700 while the spring 2710 is at least partially compressed. As shown in FIG. 28B, a portion of the pusher element 920 is pushed out of the liner 2700, exposing a distal end 2716 of the pusher element 920. For example, the relative translation of the pusher element 920 with respect to the liner 2700 can expose a connection point 2802 at which the localization element 930 (not shown in FIG. 28B) can connect to the pusher element 920. Exposing the connection point 2802 enables the localization element 930 to release from the pusher element 920.

The liner 2700 can enclose at least a connection point 2802 between the pusher element 920 and the localization element 930. Enclosing the connection point 2802 and at least part of the localization element 930 within the liner 2700 can reduce friction between the connection point 2802, localization element 930, and delivery needle 906. In particular, spring force in the localization element 930, which can be configured to deploy from the delivery needle 906 in a curved configuration, can push the proximal end of the localization element 930 against an inner surface of the delivery needle 906. The connection point 2802 may have irregularly shaped surfaces that can further increase friction against the delivery needle 906. By enclosing at least the proximal end of the localization element 930 and the connection point 2802 within the stainless steel liner 2700, the spring force can push the proximal end against the liner 2700 rather than the inner surface of the delivery needle 906. Accordingly, the inner surface of the delivery needle 906 can be protected from potential damage from the localization element 930 and pusher element 920 sliding against the inner surface of the delivery needle 906, and friction resisting the deployment of the localization element 930 can be reduced. The liner 2700 may enclose more of the localization element 930 than the proximal end; for example, the liner 2700 may enclose up to the entire localization element 930 before deployment.

A length of the spring 2710 is based on an amount of the localization element 930 enclosed in the stainless steel liner 2700. In particular, the difference between the compressed and uncompressed lengths of the spring 2710 can be at least the length of the localization element 930 and connection point 2802 with the pusher element 920 that are enclosed within the liner 2700. Alternatively, in variations using the pusher element 2520 described with respect to FIGS. 25A-C instead of the pusher element 920, the difference between the compressed and uncompressed lengths of the spring may be more or less than the length of the localization element 930 enclosed in the liner 2700.

The tissue localization device 900 can include a retraction lock that prevents or limits retraction of the pusher element 920 into the stainless steel liner 2700 after the localization element 930 has been fully deployed. Limiting retraction of the pusher element 920 can improve the safety of the tissue localization device 900 after deployment of the localization element 930. For example, tissue of the patient may be pinched between the pusher element 920 and the liner 2700 or delivery needle 906 as the pusher element 920 is retracted; preventing or limiting the retraction can reduce the likelihood of pinching the tissue of the patient. Furthermore, since the pusher element 920 may extend beyond an end of the delivery needle 906 after complete deployment of the localization element 930, as shown for example in FIG. 28B, the pusher element 920 can additionally or alternatively shield the tip of the delivery needle 906 to reduce a likelihood of the user of the tissue localization device 900 injuring themselves or others with the exposed sharp needle tip after the tip is withdrawn from the tissue.

Figure 29A:
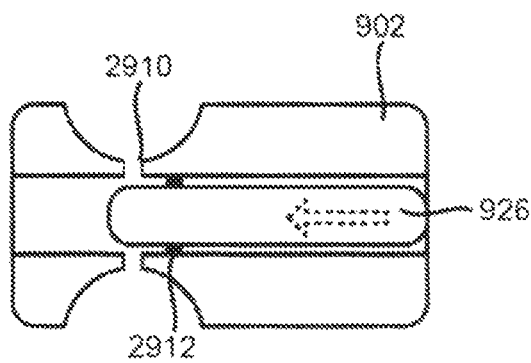
FIGS. 29A-J illustrate example retraction locks.
Figure 29B:
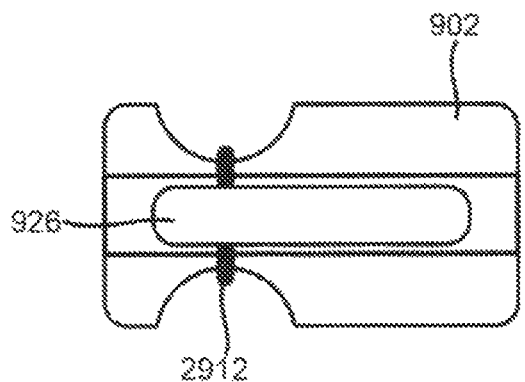
Figure 29C:
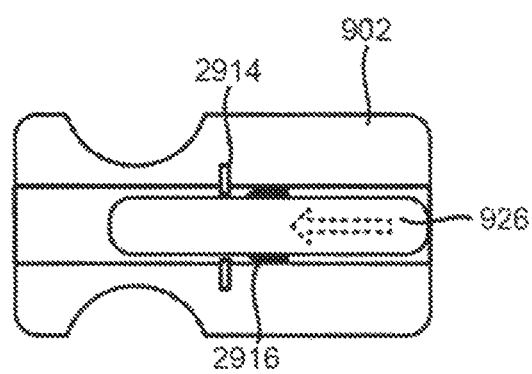

FIGS. 29A-J illustrate that the retraction lock can limit retraction of the pusher element 920. FIGS. 29A and 29B are top-view cross-sections of the tissue localization device handle 902 and the pusher plug 926. As described above with respect to FIG. 9, the pusher plug 926 can be coupled to the slidable delivery control 904 and pusher element 920, and can transfer longitudinal motion of the slidable delivery control 904 to the pusher element 920. Referring to the example of FIGS. 29A-B, the pusher plug 926 can include one or more spring-loaded pins 2912 that can be compressed inside the lumen of the handle 902 (as shown in FIG. 29A) and, as shown in FIG. 29B, can translate or pop into holes 2910 when the pusher plug 926 reaches a designated position in the handle 902. For example, the holes 2910 can be placed such that the pins 2912 can pop into the holes 2910 when the localization element 930 is fully deployed and has separated from the pusher element 920. The holes 2910 can be placed such that the pins 2912 pop into the holes when the slidable delivery control 904 is pushed beyond the point at which the localization element 930 separates from the pusher element 920. The spring-loaded pins 2912 may have limited lateral movement, limiting a longitudinal distance the slidable delivery control 904 can be moved after the pins 2912 have locked into the holes 2910. The spring-loaded pins 2912 may be compressible to slide back into the handle 902 lumen after locking into the holes 2910, permitting translation of the slidable delivery control and retraction of the pusher element 920.

Figure 29D:
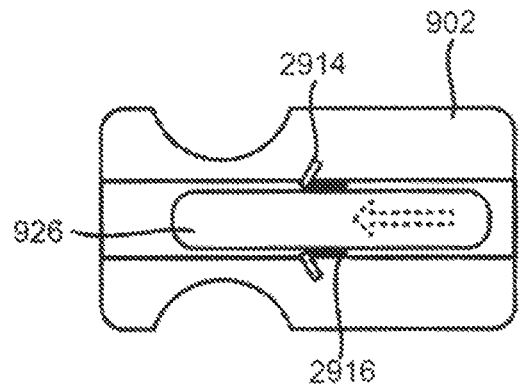
Figure 29E:
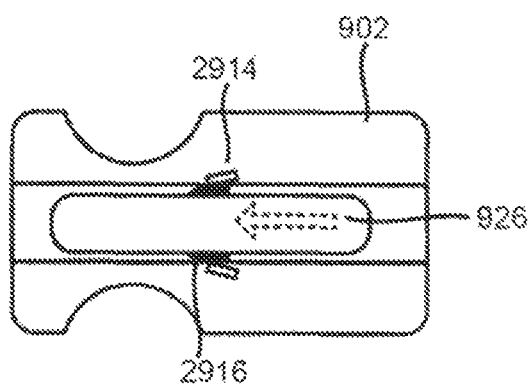
Figure 29F:
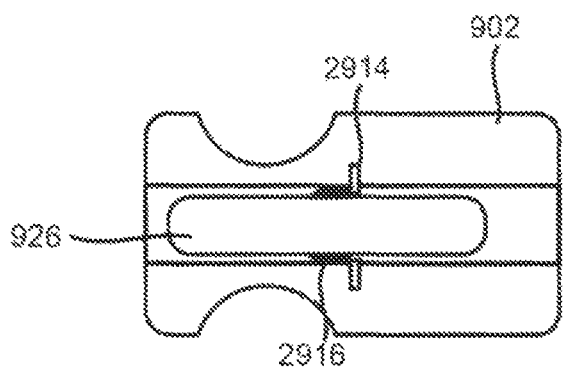

FIGS. 29C-F are top-view cross-sections of another example of a retraction lock. In the example of FIGS. 29C-F, one or more teeth 2916 can be coupled to the pusher plug 926 and one or more locks 2914 can be disposed on an inner surface of the lumen of the handle 902. The locks 2914 can be spring-loaded or hinged to permit free movement of the teeth 2916 and pusher plug 926 in a distal direction (e.g., toward the left of FIG. 29C). FIGS. 29D and E illustrate progressive rotation of the locks 2914 to permit movement of the teeth 2916 in the distal direction. After the teeth 2916 have moved to a distal side of the teeth 2916, as shown in FIG. 29F, the locks 2914 may rotate back to an initial position to prevent or limit movement of the pusher plug 926 toward the proximal end of the tissue localization device 900 (e.g., toward the right of FIG. 29D). The locks 2914 may be positioned in the handle 902 such that the teeth 2916 are distal to the locks 2914 at or beyond the point the localization element 930 is fully deployed. Alternative variations of the teeth 2916 can lock into holes when the pusher plug 926 is translated forward to a designated position in the tissue localization device handle 902. The one or more teeth 2916 when locked in the holes can limit proximal translation of the slidable delivery control 904.

Figure 29G:
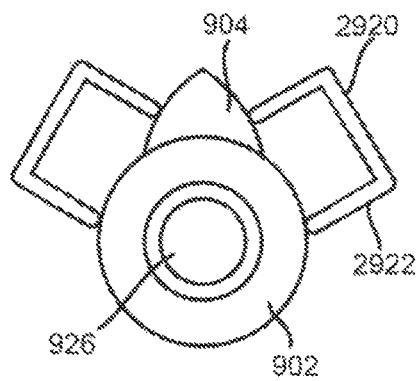
Figure 29H:
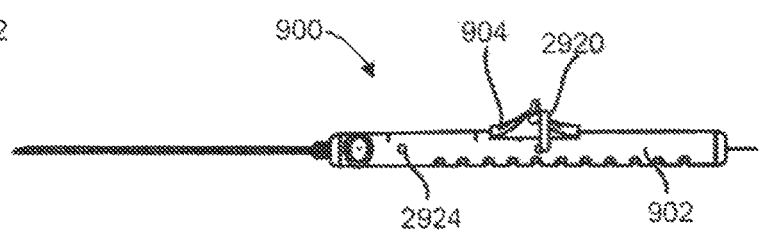
Figure 29I:
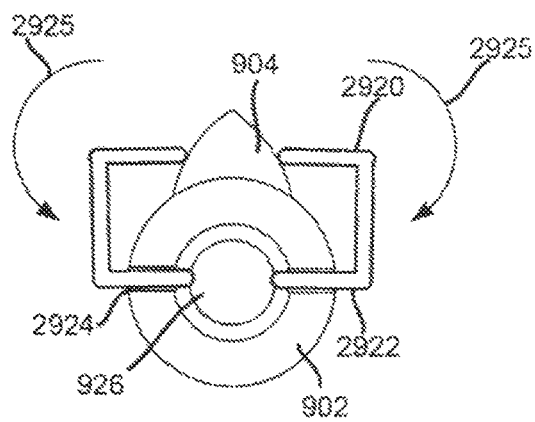
Figure 29J:
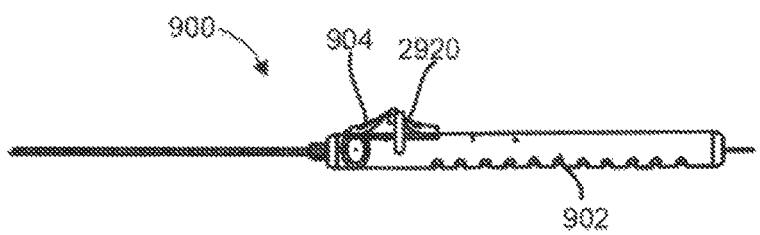

FIGS. 29G-J illustrate a method for using a retraction lock 2920. FIG. 29G is a transverse cross-section of the tissue localization device handle 902 including the retraction lock 2920, and FIG. 29H is a side view of the tissue localization device 900 including the retraction lock 2920. The retraction lock 2920 can be a structure external to the handle 902 and coupled to the handle 902 or the slidable delivery control 904. The retraction lock 2920 can be fabricated from metal (e.g., as a wireform) or fabricated as a polymer (e.g., via molding). The retraction lock 2920 can have one or more arms 2922 configured to lock a position of the slidable delivery control 904 when or after the localization element 930 has been deployed into tissue. The retraction lock 2920 can be rotatably coupled to the slidable delivery control 904 and/or the arms 2922 can be elastically deformable from a biased unlocked configuration shown in FIGS. 29G and 29H to a relaxed or unbiased locked configuration shown in FIGS. 29I and 29J. The arms 2922 can elastically pop and/or rotate into a locked configuration, as shown by arrows 2925. The arms 2922 can slide along an exterior of the handle 902 during longitudinal motion of the slidable delivery control 904, and rotate to lock into the handle 902 or pusher plug 926 through holes 2924 in the handle 902. FIG. 29I is a transverse cross-section illustrating the arms 2922 that can be locked into the holes 2924 to lock motion of the slidable delivery control 904, while FIG. 29J is a side view of the tissue localization device 900 with the arms 2922 that can be locked into the holes 2924. The retraction lock 2920 can be spring loaded such that the arms 2922 can automatically pop into the holes 2924, or the retraction lock 2920 can be configured to be manually clamped into the holes 2924 by a user of the device 900.

As described above, the tissue localization device 900 can be used with an ultrasound transducer. The user can operate the tissue localization device 900 with one hand and the ultrasound transducer with the other hand, using the ultrasound transducer to monitor deployment of the localization element 930 into tissue.

Figure 30A:
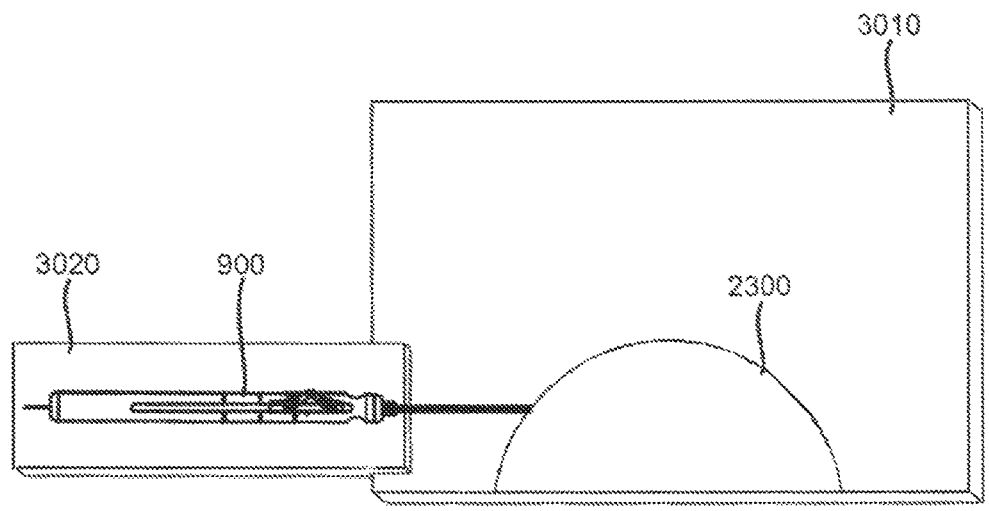
FIGS. 30A-B illustrate an example setup for using the tissue localization device during imaging.
Figure 30B:
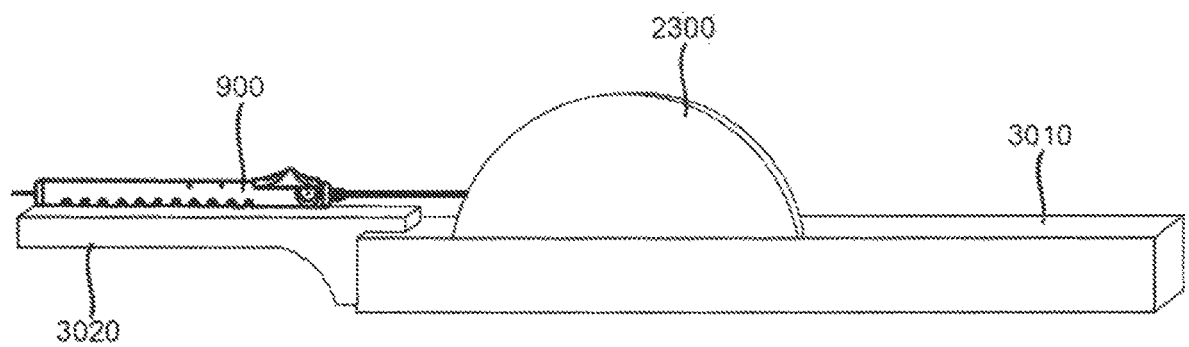

A user may use X-ray to confirm the desired deployment of the localization element 930. An example use of the tissue localization device 900 under X-ray monitoring is shown in FIGS. 30A-B. FIG. 30A illustrates a top view of a mammographic X-ray setup, which include a bucky 3010 and a support platform 3020. FIG. 30B illustrates a side view of the setup shown in FIG. 30A.

Referring to FIGS. 30A-B, the bucky 3010 can support tissue 2300 for X-ray imaging. The bucky 3010 can be placed on an opposite side of the tissue 2300 from an X-ray tube delivering X-rays to the tissue 2300. For example, in FIG. 30A, the bucky 3010 is below the tissue 2300, which can be placed below an X-ray tube (not shown). The bucky 3010 may alternatively be aligned in a vertical direction, such that the tissue 2300 is placed horizontally between an X-ray tube and the bucky 3010 for imaging.

The support platform 3020 can couple to the bucky 3010 and support the tissue localization device 900. The support platform 3020 can clamp to the bucky 3010, adhere to an adhesive on the bucky 3010, lock into brackets in the bucky 3010, or otherwise removably coupled to the bucky 3010. Alternatively, the support platform 3020 can be integrated with the bucky 3010. In some variations, the support platform 3020 may be adjustable to accommodate different tissue sizes or different angles of entry into the tissue. For example, the support platform 3020 may be hinged to tilt the tissue localization device 900 at an angle from a horizontal plane of the bucky 3010 or to swivel within the horizontal plane. The support platform 3020 may additionally or alternatively have an adjustable height to adjust a distance between the needle of the tissue localization device 900 and the bucky 3010. The platform 3020 may further include supports to maintain a position of the tissue localization device 900. For example, the platform 3020 may include straps to strap the tissue localization device 900 to the platform 3020 or protruding structures placed at sides and ends of the tissue localization device 900 to reduce a likelihood of the device 900 rolling or sliding on the platform 3020.

As shown in FIGS. 30A-B, a user (e.g., a radiologist) may guide a patient until the patient is positioned with tissue of interest 2300 placed between the bucky 3010 and an X-ray tube. After initial X-ray imaging of the tissue 2300 to identify a target tissue site in the tissue 2300, the user may guide the needle of the tissue localization device 900 into the tissue 2300 and deploy the localization element 930 into the tissue. To ensure correct positioning of the localization element 930 in the tissue, the user may repeat X-ray imaging of the tissue 2300 before, during, or after deployment of the localization element 930. The user may leave the patient's side during imaging to reduce the user's exposure to the X-rays. The support platform 3020 can therefore support the tissue localization device 900 in the user's absence, maintaining the positioning of the device and localization element 930 during imaging and improving comfort for the patient. After the localization element 930 has been deployed to the user's satisfaction, the user can withdraw the tissue localization device 900 from the tissue 2300 and expose the tracking wire 932, as described above.

Figure 31A:
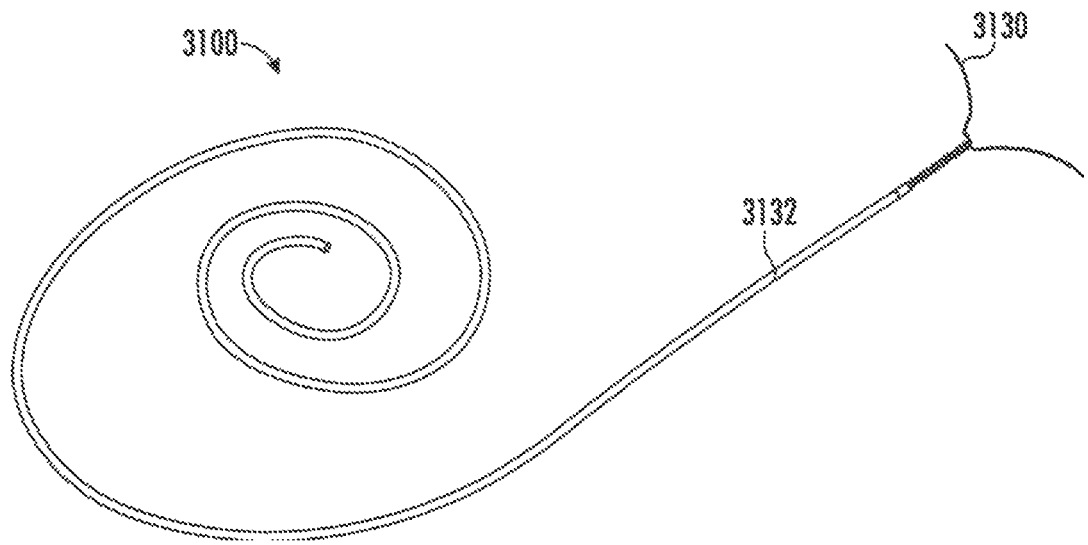
FIGS. 31A-B illustrate variations of a tissue localization wire.
Figure 31B:
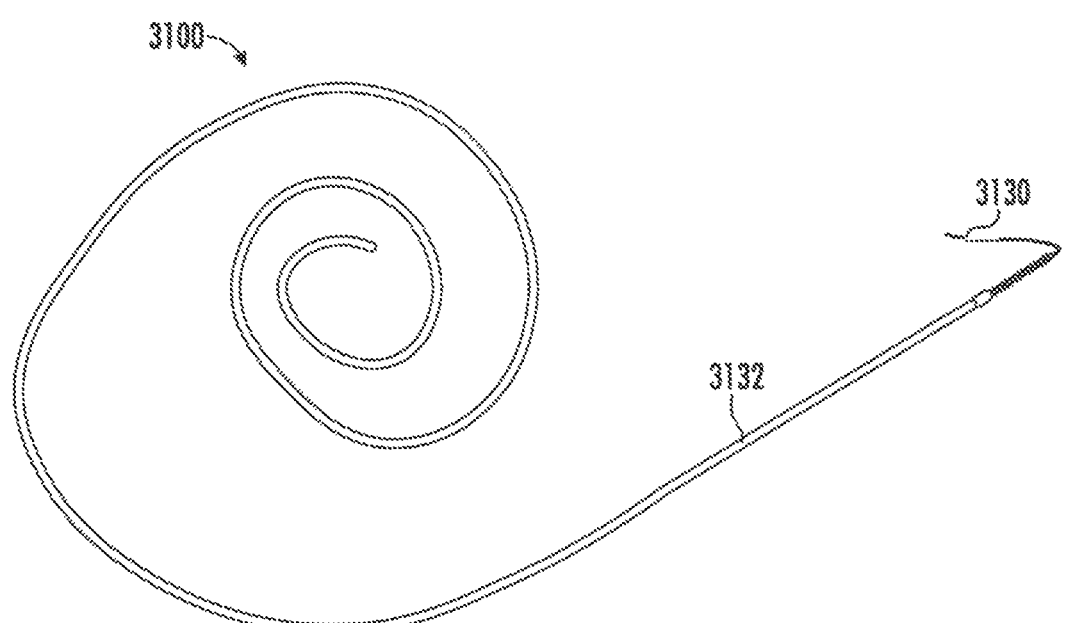

FIGS. 31A-B illustrate that a tissue localization wire 3100 can be used to localize tissue without (as shown) or with the localization element 930 and tracking wire 932. The tissue localization wire 3100 can be deployed from a handle/pusher/slidable delivery control based needle system similar to that described by the tissue localization device 100 or 900, or can be configured to be advanced manually directly through a delivery needle (e.g., without use of the pusher element 920 and/or slidable delivery control 904).

The tissue localization wire 3100 can include a localization element 3130 and a tracking wire 3132. The localization element 3130 can be a flexible wire or length of metal, polymer, or combinations thereof. The localization element 3130 can be configured to take on an arcuate or curvilinear configuration when deployed into tissue, an example of which is shown in FIG. 31A. Alternatively, the localization element 3130 can be configured to take on a linear or bent configuration when deployed, as shown for example in FIG. 31B. The localization element 3130 can alternatively take on different shapes. The localization element 3130 is stiff enough to pierce into tissue of a patient and maintain a relative position in the tissue as the patient moves, but flexible enough to collapse, prior to deployment, into a delivery needle (e.g., the delivery needle 906 of the tissue localization device 900).

The highly flexible suture-like tracking wire 3132 can be coupled to the localization element 3130 and configured to aid deployment of the tracking wire 3132 from a delivery needle. For example, if the tissue localization wire 3100 is configured for manual deployment from a delivery needle, the tracking wire 3132 can be configured to push the localization element 3130 out of the delivery needle when the tracking wire 3132 is pushed. After the localization element 3130 has been deployed into tissue of a patient, at least a portion of the tracking wire 3132 may extend from the tissue to serve as a path or trail guiding a surgeon to the target tissue site. The exposed portion of the tracking wire 3132 is flexible enough to be able to be configured to be wrapped or tied and secured to the surface of the skin by, for example, adhesive dressing. For example, the exposed portion of the tracking wire 3132 may be wrapped into a circle approximately 1-5 cm in diameter and taped by surgical tape to the patient.

The tracking wire 3132 can be a flexible wire including one or more multi-strand filaments encased in a polymer jacketing, such as the polymer jacketing 1132. However, the tracking wire 3132 can alternatively include any metal, metal alloy, polymer, or combinations thereof, and can be a single-stranded wire, a multi-stranded wire, a coil spring similar to flexible guidewires used in cardiovascular applications, encased in a jacketing, or not encased in a jacketing, or polymer (e.g. fluoropolymer) coated. The tracking wire 3132 can have a substantially circular cross-section, or can have cross-sections of other shapes (e.g., square). The tracking wire 3132 can have sufficient column strength to facilitate deployment (e.g., by pushing) of the localization element 3130 out the end of a delivery needle, but possess sufficient flexibility to be easily coiled without yielding so that it may be comfortably secured to tissue surface of a patient. The tracking wire 3132 may be between approximately 0.010 and 0.025 inches in diameter. When the tracking wire 3132 is configured to be pushed by hand through a delivery needle, the tracking wire 3132 may have a sufficiently large diameter and/or be sufficiently column strength to prevent buckling or "S"ing within the needle lumen. The tracking wire may be longer or shorter than shown in FIGS. 31A-B.

It can be difficult to perform wire localization procedures or other ultrasound guided breast procedures because the tissue is particularly mobile or unstable, as in the instance of a fatty-replaced breast. The instability and mobility of the fatty tissue can make it challenging for even a skilled clinician to place an ultrasound-guided needle to the desired location. The mere act of mildly pressing an ultrasound on the skin near the target tissue can cause the target tissue to move out of the field of view of the ultrasound transducer. The forces involved in placing and advancing a needle through this tissue can cause additional unwanted mobility of the tissue, further compromising ultrasound visualization.

Figure 32A:
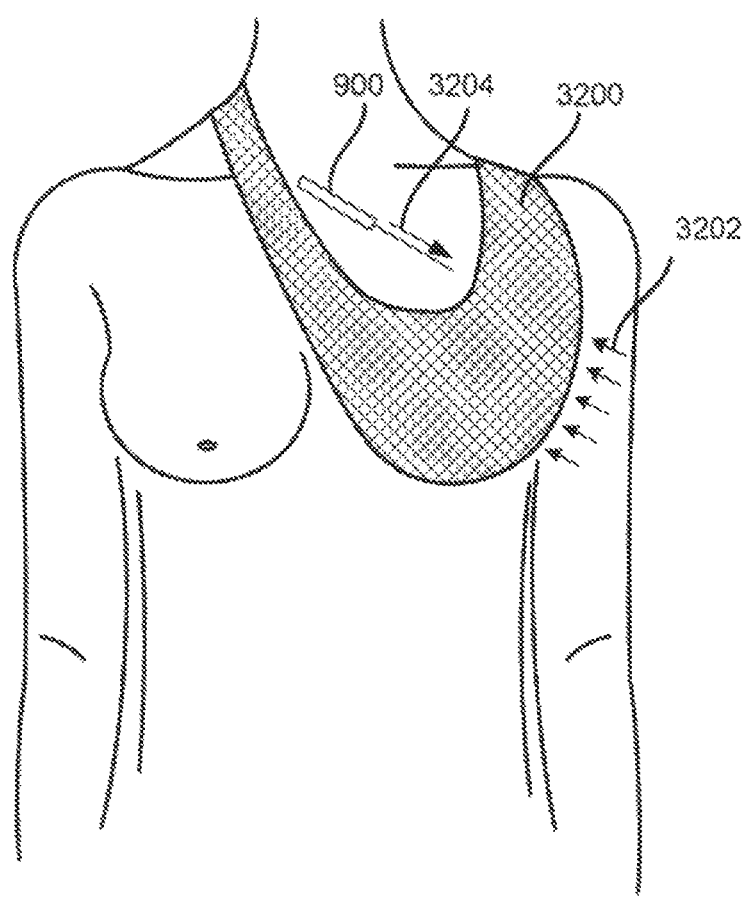
FIG. 32A-B illustrate variations of using a stabilization sling.

FIG. 32A illustrates a tissue stabilization device, such as a securement or stabilization sling 3200 for stabilizing tissue to be penetrated by the tissue localization device 900 or 100 and imaged by an ultrasound probe. The sling 3200 can stabilize breast tissue and provide support for such tissue as the delivery needle 906 of the tissue localization device 900 or 100 or other ultrasound-guided devices (e.g., percutaneous biopsy, fine needle aspiration, and percutaneous marker devices) The sling 3200 can stabilize the mobile tissue and allow for needle penetration as well as positioning of the ultrasound probe for realtime ultrasound guidance.

The sling 3200 can comprise a polymeric material, a fabric, or combinations thereof. The sling 3200 can comprise an iodophor-impregnated layer or coating (e.g., 3M™ Ioban™ incise drapes or coverings), for example to cover the skin and minimize the risk of surgical site infection. The sling 3200 can comprise an anti-microbial layer that does not contain iodine, for example, for patients who have an iodine allergy. The anti-microbial layer can comprise silver nanoparticles. The sling 3200 (or other stabilization devices herein described) can be used to support mobile tissue such as, but not limited to, breast tissue (as stated above), abdominal tissue, leg tissue, upper arm tissue, buttock tissue, or scrotal tissue. The sling 3200 can comprise one or more biocompatible adhesive-backed layers that adhere to the skin to provide an appropriate ultrasound interface and a grip on the skin to maintain traction on the tissue to decrease tissue mobility.

The sling 3200 can deliver a support pressure 3202 against the breast surface. The support pressure 3200 can have a directional component toward the medial direction of the wearer of the sling. The tissue localization device 900 or 100 can be inserted, as shown by arrow 3204, into the breast not through and medial to the sling (as shown) or through the sling. The insertion direction of the tissue localization device can have a directional component toward the lateral side of the wearer of the sling. The support pressure 3200 can prevent or minimize breast motion or deformation during the insertion and other use of the tissue localization device 900 or 100 in the breast.

Figure 32B:
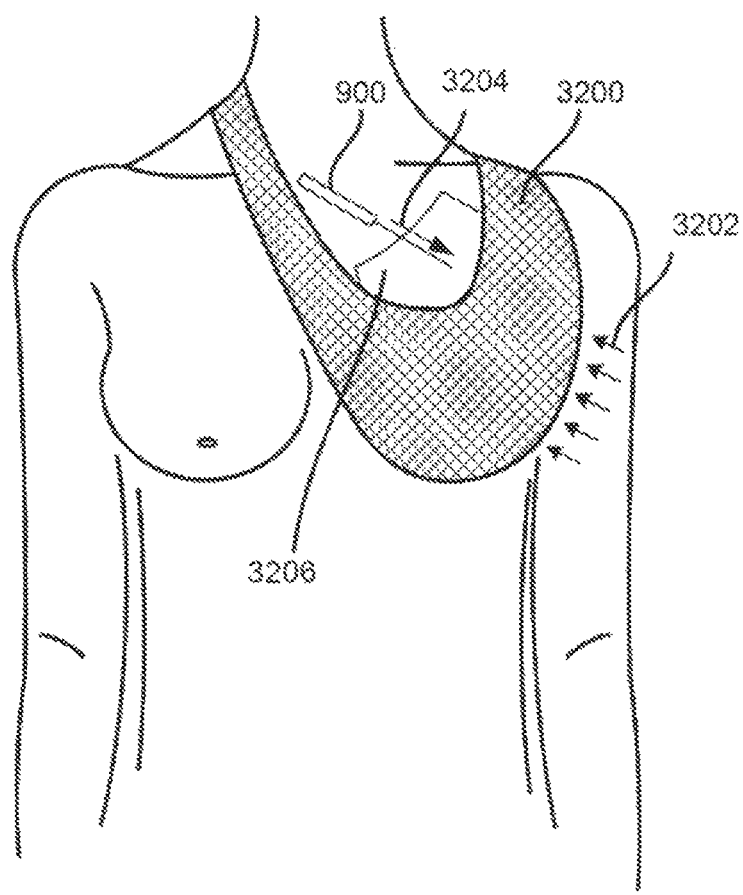

FIG. 32B illustrates that a patch 3206 can be placed on the breast, for example at the site of insertion of the tissue localization device 900 or 100 through the skin. The patch 3206 can be placed on the breast before insertion of the tissue localization device 900 through the patch 3206 and the breast skin. The patch 3206 can be above or below the sling 3200. The patch 3206 can be attached to the sling 3200. The patch 3206 can be made from the same or different material as the sling 3200. The patch 3206 can have one or more iodophor-impregnated layers or coating (e.g., 3M™ Ioban™ incise drapes or coverings), for example to cover the skin and minimize the risk of surgical site infection.

The tissue stabilization devices can be comprised of a clamshell type device, with one side of the clamshell having a rigid surface and the other side of the clamshell comprised of a yoke (e.g. two prongs) that suspend a segment of flexible adhesive polymer sheeting such as Ioban™ between the two prongs. The hinge of the clamshell may be spring loaded to "close" the clamshell and/or may have a releaseable ratcheting mechanism to hold the clamshell closed around the breast tissue at an adjustable (e.g., by further ratcheting or release of the ratchet) level of compression. The clamshell can be closed around the breast. The interior surface of the rigid side of the clamshell can contact the patient's breast and form a stable platform against which the breast can be further stabilized by the opposing side of the clamshell. The opposing surface of the clamshell may be comprised of an adhesive-backed polymer sheeting whose inner surface is pressed against the breast so that the breast tissue can be mildly compressed between the clamshell device. The clamshell can be applied to the breast in a number of directions (e.g. cranio-caudal, medial-lateral, etc.) as desired by the clinician. The rigid clamshell can be configured to have a pad (e.g. foam) to aid in comfort during compression. After the clamshell has been applied to the breast, an ultrasound probe and needle may be placed into or onto either the exposed skin or the adhesive film region of the stabilization device.

The two opposing sides can be not hinged as in the clamshell configuration described above. For example, the two roughly parallel surfaces can be advanced towards each via one or more ratchet or screw-feed mechanisms until the desired level of compression around the breast is achieved. As with the previously described clamshell device, one compression surface can be relatively rigid while the opposing compression surface can be comprised of flexible film suspended by the prongs of a yoke. The rigid side need not be a flat plane but can also be curved (e.g. slightly concave) to provide additional comfort and stabilization. In use, the two opposing sides can be brought together around the breast in the desired orientation and the breast tissue is thus stabilized for use in an ultrasound guided percutaneous procedure. At the end of the procedure the stabilization device can be released and the film removed.

The film region need not comprise the entire compression surface. Both sides can be rigid and there can be window regions within the compression surfaces. The window regions may or may not contain film sheeting depending on the size of the window. In some instances windows in the compression surfaces will not be needed (e.g., in some large breasted patients) and the skin can be sufficiently accessed in areas where there are not compression surfaces. Both compression sides can be comprised of the film yoke to optimize accessibility of the breast to the needle or ultrasound probe.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the disclosure.

Methods recited herein may be carried out in any order of the recited events that is logically possible, as well as the recited order of events. Moreover, additional elements of the method or operations may be provided or elements of the method or operations may be eliminated to achieve the desired result.

Furthermore, where a range of values is provided, every intervening value between the upper and lower limit of that range and any other stated or intervening value in that stated range is encompassed within the disclosure. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present disclosure (in which case what is present herein shall prevail). The referenced items are provided solely for their disclosure prior to the filing date of the present application. Nothing herein is to be construed as an admission that the disclosure is not entitled to antedate such material by virtue of prior disclosure.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this disclosure belongs.

This disclosure is not intended to be limited to the scope of the particular forms set forth, but is intended to cover alternatives, modifications, and equivalents of the variations or variations described herein. Further, the scope of the disclosure fully encompasses other variations that may become obvious to those skilled in the art in view of this disclosure.

We claim:

1. A tissue localization device, comprising:
   a handle configured to be held using one hand;
   a delivery needle extending from the handle, wherein the delivery needle comprises a needle lumen;
   a pusher configured to slidably translate within the needle lumen; and
   a localization marker detachably coupled to the pusher and configured to form into a partial-loop configuration when deployed out of the delivery needle,
      wherein the localization marker is slidably translatable within the needle lumen by translating a slidable delivery control in a first longitudinal direction along a surface of the handle,
      wherein the localization marker is translatable before release of the localization marker from the tissue localization device, and
      wherein the pusher includes one or more spring-loaded pins moveable between a compressed position and an extended position,
      wherein:
         when in the compressed position, the pusher is arranged and configured to slidably translate within the needle lumen; and
         when in the extended position, the one or more spring-loaded pins are received within one or more holes formed in the handle to prevent the pusher from slidably translating within the needle lumen.

2. The device of claim 1, wherein the pusher is slidably translatable within the needle lumen in response to the translation of the slidable delivery control.

3. The device of claim 1, wherein the localization marker comprises a proximal frame portion and the proximal frame portion is configured to detachably interlock with a recess defined along the pusher.

4. The device of claim 1, wherein the localization marker is retractable back into the needle lumen before release from the tissue localization device needle by translating the slidable delivery control in a second longitudinal direction opposite the first longitudinal direction along the surface of the handle, wherein the localization marker is retractable before release of the localization marker from the tissue localization device.

5. The device of claim 1, where the pusher is coupled to the slidable delivery control via a connector extending through a slot defined along a dorsal side of the handle.

6. The device of claim 1, wherein the localization marker is coupled to a tracking wire and the tracking wire is configured to align secant to the partial-loop configuration of the localization marker upon release of the localization marker from the tissue localization device.

7. The device of claim 1, wherein the one or more spring-loaded pins are received within the one or more holes when the pusher has reached a designated position relative to the handle corresponding to the localization marker being fully deployed and having separated from the pusher.

* * * * *